(12) United States Patent
Nain et al.

(10) Patent No.: US 9,753,023 B2
(45) Date of Patent: Sep. 5, 2017

(54) NANOFIBER GRID AND RELATED METHODS

(71) Applicant: Carnegie Mellon University, Pittsburgh, PA (US)

(72) Inventors: Amrinder Singh Nain, Christiansburg, VA (US); Bahareh Behkam, Christiansburg, VA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 14/990,206

(22) Filed: Jan. 7, 2016

(65) Prior Publication Data
US 2016/0202289 A1    Jul. 14, 2016

Related U.S. Application Data

(60) Provisional application No. 62/100,500, filed on Jan. 7, 2015.

(51) Int. Cl.
*G01N 33/483* (2006.01)

(52) U.S. Cl.
CPC .............................. *G01N 33/4833* (2013.01)

(58) Field of Classification Search
CPC .................................................. G01N 33/4833
See application file for complete search history.

(56) References Cited

U.S. PATENT DOCUMENTS 9,029,149 B2    5/2015 Nain

OTHER PUBLICATIONS

Handbook of Imaging in Biol. Mechanics, Eds. C. P. Neu & G. M. Genin, Ch. 23, Cell Interactions in Wire (Fiber)-Based Structures & Scaffolds, Sheets et al., pp. 299-311, CRC Press, Boca Raton, Oct. 24, 2014, cover pp. & table of contents, https://www.crcpress.com/Handbook-of-Imaging-in-Biological-Mechanics/Neu-Genin/p/book/9781466588134#googlepreview.*
Alberts, et al., "Cell Junctions, Cell Adhesion, and the Extracellular Matrix," Molecular Biology of the Cell, Garland Science, (2002), Chapter 19, pp. 1131-1204.
Amano, et al., Rho-Kinase/ROCK: A Key Regulator of the Cytoskeleton and Cell Polarity, Cytoskeleton, (Sep. 2010), vol. 67, pp. 545-554.
Balint, et al., "Conductive polymers: Towards a smart biomaterial for tissue engineering," Acta Biomaterialia, (2014), vol. 10, pp. 2341-2353.
Bergert, et al., "Cell mechanics control rapid transitions between blebs and lamellipodia during migration," PNAS, (Sep. 4, 2012), vol. 109, No. 36, pp. 14434-14439.

(Continued)

*Primary Examiner* — Rosanne Kosson
(74) *Attorney, Agent, or Firm* — The Webb Law Firm

(57) ABSTRACT

Methods and systems are provided for measuring single and multi-cell inside-out and/or outside-in forces on a nanofiber grid. Single and multi-cells are deposited on, or migrate onto the nanofiber grid where the cell or cells are in contact with at least one fiber of the nanofiber grid and forces generated by the cells are observed and measured using deflection sensing methods. Furthermore, analyte-testing platforms using the nanofiber grid are described herein. Also provided are methods and apparatus including automated analyte-testing platforms using the nanofiber grid.

31 Claims, 42 Drawing Sheets
(6 of 42 Drawing Sheet(s) Filed in Color)

(56) References Cited

OTHER PUBLICATIONS

Brevier, et al., "The asymmetric self-assembly mechanism of adherent junctions: a cellular push-pull unit," Physical Biology (Feb. 2008), vol. 5, pp. 1-10.
Carlisle, et al., "The mechanical stress-strain properties of single electrospun collagen type 1 nanofibers," Acta Biomaterialia, (2010), vol. 6, pp. 2997-3003.
Cavey, et al., "Molecular Bases of Cell-Cell Junctions Stability and Dynamics," Cold Spring Harbor Perspectives in Biology, (2009), vol. 1, pp. 1-18.
Chen, C.S., "Mechanotransduction—a field pulling together?", Journal of Cell Science, (Aug. 19, 2008), vol. 121, pp. 3285-3292.
Chiu, et al., "Effects of Disturbed Flow on Vascular Endothelium: Pathophysiological Basis and Clinical Perspectives," Physical Rev., (Jan. 2011), vol. 91, No. 1, pp. 1-106.
Christ, et al., "Measurement of single-cell adhesion strength using a microfluidic assay," Biomed Microdevices, (2010), vol. 12, No. 3, pp. 443-455.
Chu, et al., "Force measurements in E-cadherin-mediated cell doublets reveal rapid adhesion strengthened by actin cytoskeleton remodeling through Rac and Cdc42," The Journal of Cell Biology, (Dec. 20, 2004), vol. 167, No. 6, pp. 1183-1194.
Chun, et al., "Antibody against the actin-binding protein depactin attenuates Ca2+ signaling in starfish eggs," Biochemical and Biophysical Research Communications, (2013), vol. 441, pp. 301-307.
Darling, et al., "A Thin-Layer Model for Viscoelastic, Stress-Relaxation Testing of Cells Using Atomic Force Microscopy: Do Cell Properties Reflect Metastatic Potential?", Biophysical Journal, (Mar. 2007), vol. 92, pp. 1784-1791.
Das, et al., "Traction force microscopy on-chip: shear deformation of fibroblast cells," The Royal Society of Chemistry, Lab Chip, (2008), vol. 8, pp. 1308-1318.
Dolatshahi-Pirouz, et al., "Synthesis of Functional Nanomaterials via Colloidal Mask Templating and Glancing Angle Deposition (GLAD)," Advanced Engineering Materials, (2010), vol. 12, No. 9, pp. 899-905.
Doyle, et al., "One-dimensional topography underlies three-dimensional fibrillar cell migration", Journal of Cell Biology, (Feb. 16, 2009), vol. 184, No. 4, pp. 481-490.
Elson, et al., "The role of mechanics in actin stress fiber kinetics," Exp. Cell Res., (Oct. 1, 2013), vol. 319, No. 16, pp. 2490-2500.
Engler, et al., "Matrix Elasticity Directs Stem Cell Lineage Specification," Cell, (Aug. 24, 2006), vol. 126, pp. 677-689.
Eyckmans, et al., "A Hitchhiker's Guide to Mechanobiology," Dev. Cell., (Jul. 19, 2011), vol. 21, No. 1, pp. 35-47.
Ezratty, et al., "Microtubule-induced focal adhesion disassembly is mediated by dynamin and focal adhesion kinase," Nature Cell Biology, (Jun. 2006), vol. 7, No. 6, pp. 581-590, (with Supplementary Information pp. 1-3).
Ferrell, et al., "Measurement of cell forces using a microfabricated polymer cantilever sensor," Sensors and Actuators A: Physical, (2011), vol. 170, pp. 84-89.
Fournier et al., "Force transmission in migrating cells," Journal of Cell Biology, (2010), vol. 188, No. 2, pp. 287-297.
Fu, et al., "Mechanical regulation of cell function with geometrically modulated elastomeric substrates," Nature Methods, (Sep. 2010), vol. 7, No. 9, pp. 733-736.
Gautrot, et al., "The Nanoscale Geometrical Maturation of Focal Adhesions Controls Stem Cell Differentiation and Mechanotransduction," American Chemical Society, Nano Lett., (2014), vol. 14, pp. 3945-3952.
Gestos, et al., "Tensile testing of individual glassy, rubbery and hydrogel electrospun polymer nanofibres to high strain using the atomic force microscope," Polymer Testing, (2013), vol. 32, pp. 655-664.
Guilak, et al., "Control of stem cell fate by physical interactions with the extracellular matrix," Cell Stem Cell., (Jul. 2, 2009), vol. 5, No. 1, pp. 17-26.
Han et al., "Decoupling Substrate Stiffness, Spread Area, and Micropost Density: A Close Spatial Relationship between Traction Forces and Focal Adhesions," Biophysical Journal, (Aug. 2012), vol. 103, pp. 640-648.
Hanahan, et al., "Hallmarks of Cancer: The Next Generation," Cell, (Mar. 4, 2011), vol. 144, pp. 646-674.
Hoelzle, et al., "The cytoskeletal mechanisms of cell-cell junction formation in endothelial cells," Molecular Biology of the Cell, (Jan. 15, 2012), vol. 23, pp. 310-323.
Hoffman, et al., "Stretch-induced actin remodeling requires targeting of zyxin to stress fibers and recruitment of actin regulators," Molecular Biology of the Cell, (May 15, 2012), vol. 23, pp. 1846-1859.
Holle, et al., "More Than a Feeling: Discovering, Understanding, and Influencing Mechanosensing Pathways," Curr. Opin. Biotechnol., (Oct. 2011), vol. 22, No. 5, pp. 648-654.
Huang, et al., "A Stretching Device for High Resolution Live-Cell Imaging," Ann. Biomed. Eng., (May 2010), vol. 38, No. 5, pp. 1728-1740.
Ingber, D., "Opposing views on tensegrity as a structural framework for understanding cell mechanics," J. Appl. Physiol., (2000), vol. 89, pp. 1663-1678.
Ingber et al., "Tensegrity, cellular biophysics, and the mechanics of living systems," Rep. Prog. Phys., (Apr. 2014), vol. 77, No. 4, pp. 1-42.
Ishizaki, et al., "Pharmacological Properties of Y-27632, a Specific Inhibitor of Rho-Associated Kinases," Molecular Pharmacology, (2000), vol. 57, pp. 976-983.
Jaalouk, et al., "Mechanotransduction gone awry," Nat. Rev. Mol. Cell Biol., (Jan. 2009), vol. 10, No. 1, pp. 63-73.
Janmey et al., "The Mechanical Properties of Actin Gels," The Journal of Biological Chemistry, (Dec. 23, 1994), vol. 269, No. 51, pp. 32503-32513.
Kamm et al., "Part D—Bio-/Nanotribology and Bio-/Nanomechanics," 35. Cellular Nanomechanics, Springer Handbook of Nanotechnology, (2010), pp. 1171-1200.
Keely et al., "Capturing relevant extracellular matrices for investigating cell migration," F1000 Research, (2015), pp. 1-14.
Kim, et al., RhoG Protein Regulates Glycoprotein VI-Fc Receptor γ-Chain Complex-mediated Platelet Activation and Thrombus Formation, The Journal of Biological Chemistry, (Nov. 22, 2013), vol. 288, No. 47, pp. 34230-34238.
Lam et al., "Live-cell subcellular measurement of cell stiffness using a microengineered stretchable micropost array membrane," Integr. Biol. (Camb.), (Oct. 2012), vol. 4, No. 10, pp. 1289-1298.
Leerberg et al., "Vinculin, cadherin mechanotransduction and homeostasis of cell-cell junctions," Protoplasma, (2013), vol. 250, pp. 817-829.
Leipzig et al., "Unconfined creep compression of chondrocytes," Journal of Biomechanics, (2005), vol. 38, pp. 77-85.
Liu et al., "Mechanical tugging force regulates the size of cell-cell junctions," PNAS, (Jun. 1, 2010), vol. 107, No. 22, pp. 9944-9949.
Lock et al., "Cell-matrix adhesion complexes: master control machinery of cell migration," Seminars in Cancer Biology, (Mar. 2008), vol. 18, No. 1, pp. 65-76.
Matthews et al., "Cellular adaptation to mechanical stress: role of integrins, Rho, cytoskeletal tension and mechanosensitve ion channels," Journal of Cell Science, (Oct. 24, 2005), vol. 119, pp. 508-518.
McGraw et al., "Erythropoietin Receptor Signaling is Membrane Raft Dependent," PLoS One, (Apr. 3, 2012), vol. 7, Issue 4, pp. 1-9.
Meehan et al., "Role of Suspended Fiber Structural Stiffness and Curvature on Single-Cell Migration, Nucleus Shape, and Focal-Adhesion-Cluster Length," Biophysical Journal, (Dec. 2014), vol. 107, pp. 2604-2611.
Miyazaki et al., "A newly designed tensile tester for cells and its application to fibroblasts," Journal of Biomechanics, (2000), vol. 33, pp. 97-104.
Mofrad, M.R.K., "Rheology of the Cytoskeleton," Annu. Rev. Fluid Mech., (2009), vol. 41, pp. 433-453.
Moreo et al., "Modeling mechanosensing and its effect on the migration and proliferation of adherent cells," Acta Biomaterialia, (2008), vol. 4, pp. 613-621.

(56) References Cited

OTHER PUBLICATIONS

Murphy et al., "Materials as stem cell regulators," Nat. Mater., (Jun. 2014), vol. 13, No. 6, pp. 547-557.
Nagayama et al., "A novel micro tensile tester with feed-back control for viscoelastic analysis of single isolated smooth muscle cells," Medical Engineering & Physics, (2007), vol. 29, pp. 620-628.
Nain et al., "Proximal Probes Based Nanorobotic Drawing of Polymer Micro/Nanofibers," IEEE Transactions on Nanotechnology (Sep. 2006), vol. 5, No. 5, pp. 499-510.
Nain et al., "Dry Spinning Based Spinneret Based Tunable Engineered Parameters (STEP) Technique for Controlled and Aligned Deposition of Polymeric Nanofibers," Macromolecular Rapid Communications, (2009), vol. 30, pp. 1406-1412.
Nain et al., "Polymeric nanofibers: isodiametric design space and methodology for depositing aligned nanofiber arrays in single and multiple layers," Polymer Journal, (2013), vol. 45, pp. 695-700.
Puech et al., "A new technical approach to quantify cell-cell adhesion forces by AFM," Ultramicroscopy, (Jun. 2006), vol. 106, pp. 637-644.
Raman et al., "Probing cell traction forces in confined microenvironments," Lab Chip, (2013), vol. 13, No. 23, pp. 4599-4607.
Rape et al., "The Regulation of Traction Force in Relation to Cell Shape and Focal Adhesions," Biomaterials, (Mar. 2011), vol. 32, No. 8, pp. 2043-2051.
Ratheesh et al., "A bigger picture: classical cadherins and the dynamic actin cytoskeleton," Nature Reviews, Molecular Cell Biology, (Oct. 2012), vol. 13, pp. 673-679.
Ricart et al., "Measuring Traction Forces of Motile Dendritic Cells on Micropost Arrays," Biophysical Journal, Dec. 2011), vol. 101, No. 11, pp. 2620-2628.
Ridley, A.J., "Life at the Leading Edge," Cell, (Jun. 24, 2011), vol. 145, pp. 1012-1022.
Sabass et al., "High Resolution Traction Force Microscopy Based on Experimental and Computational Advances," Biophysical Journal, (Jan. 2008), vol. 94, No. 1, pp. 207-220.
Schliwa, M., "Action of Cytochalasin D on Cytoskeletal Networks," The Journal of Cell Biology, (Jan. 1982), vol. 92, pp. 79-91.
Sharma et al., "The mechanistic influence of aligned nanofibers on cell shape, migration and blebbing dynamics of glioma cells," Integrative Biology, (Aug. 2013), vol. 5, No. 8, pp. 1036-1044.
Sheets et al., "Cell Interactions in Wire (Fiber)-Based Structures and Scaffolds," Handbook of Imaging in Biological Mechanics, pp. 300-311.
Shen et al., "Single cell adhesion force measurement for cell viability identification using an AFM cantilever-based mirco putter," Measurement Science and Technology, (2011), vol. 22, 115802, pp. 1-9.
Shen et al., "Study of the time effect on the strength of cell-cell adhesion force by a novel nano-picker," Biochemical and Biophysical Research Communications, (2011), vol. 409, pp. 160-165.
Simon et al., "Strategies and results of atomic force microscopy in the study of cellular adhesion," Micron, (2006), vol. 37, pp. 1-13.
Timoshenko, S., "Strength of Materials," Part II, Advanced Theory and Problems, D. Van Nostrand Co., Inc., (1930-1940), pp. 1-78.
Wang et al., "Suspended Micro/Nanofiber Hierarchical Biological Scaffolds Fabricated Using Non-Electrospinning STEP Technique," Langmuir, (2014), vol. 30, pp. 13641-13649.
Wen et al., "Polymer physics of the cytoskeleton", Current Opinion in Solid State and Materials Science, (2011), vol. 15, pp. 177-182.
Yang et al., "Geometric Considerations of Micro-to Nanoscale Elastomeric Post Arrays to Study Cellular Traction Forces," Advanced Materials, (2007), vol. 19, pp. 3119-3123.
Yoshinaga et al., "Contraction of cross-linked actomyosin bundles," Phys. Biol., (Jun. 8, 2012). vol. 9, No. 4, pp. 1-20.
Ku et al., "Synergic effects of nanofiber alignment and electroactivity on myoblast differentiation," Biomaterials, (2012), vol. 33, pp. 6098-6104.
Sheets et al., "Shape-dependent cell migration and focal adhesion organization on suspended and aligned nanofiber scaffolds," Acta Biomaterialia, (2013), vol. 9, pp. 7169-7177.
Dolatshahi-Pirouz et al., "Fibronectin Adsorption, Cell Adhesion, and Proliferation on Nanostructured Tantalum Surfaces," ACS NANO, (2010), vol. 4, No. 5, pp. 2874-2882.
Goldfinger et al., Integrin Signaling, 2nd ed., (2013), Elsevier, Inc., vol. 2, pp. 890-895.
Santella et al., "Calcium Signaling by Cyclic ADP-Ribose and NAADP," Bioenergetics, Intracellular Calcium Waves, 2nd ed., (2013), pp. 331-336.
Harma et al. "Aligned and suspended fiber force probes for drug testing at single cell resolution," Biofabrication, (2014), vol. 6, No. 4, 045006.

* cited by examiner

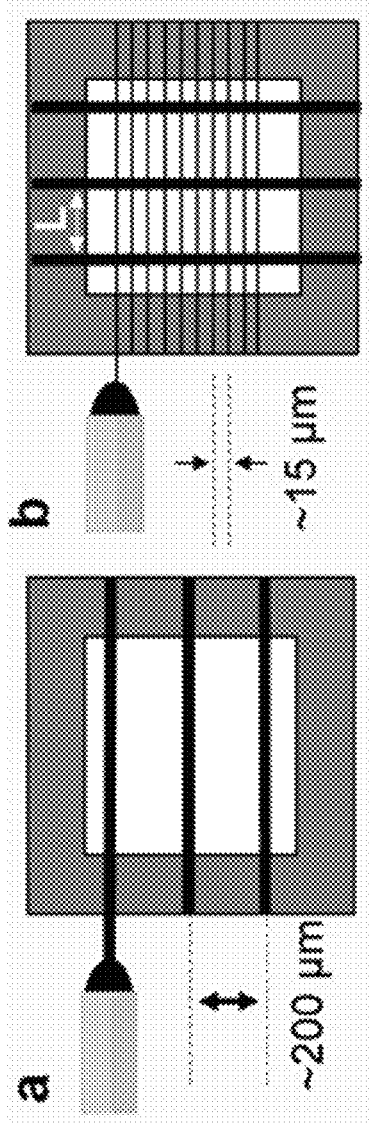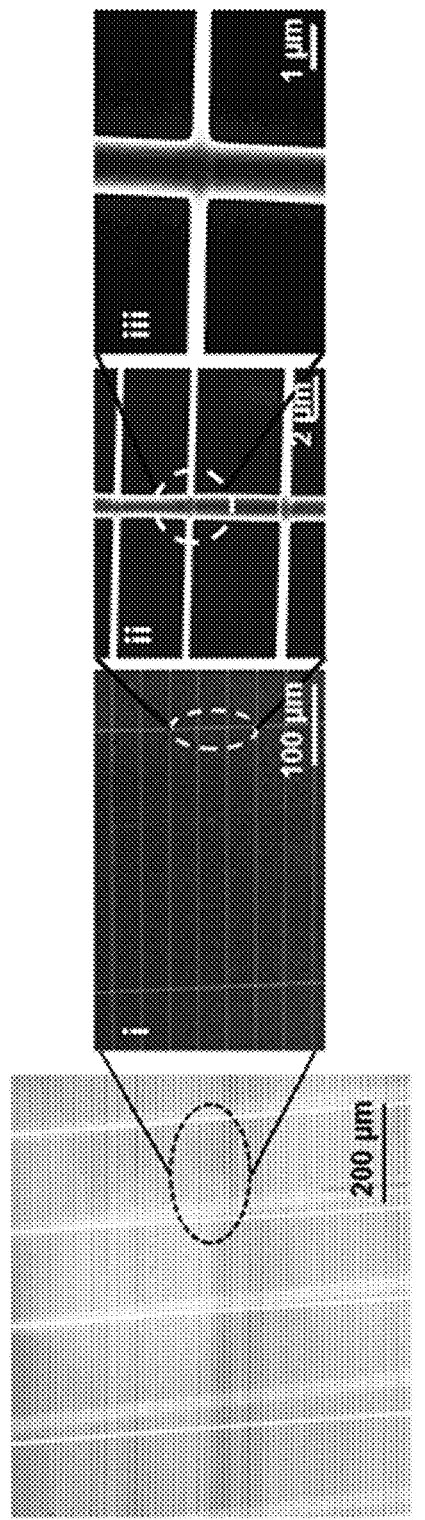
Fig. 1
Fig. 2

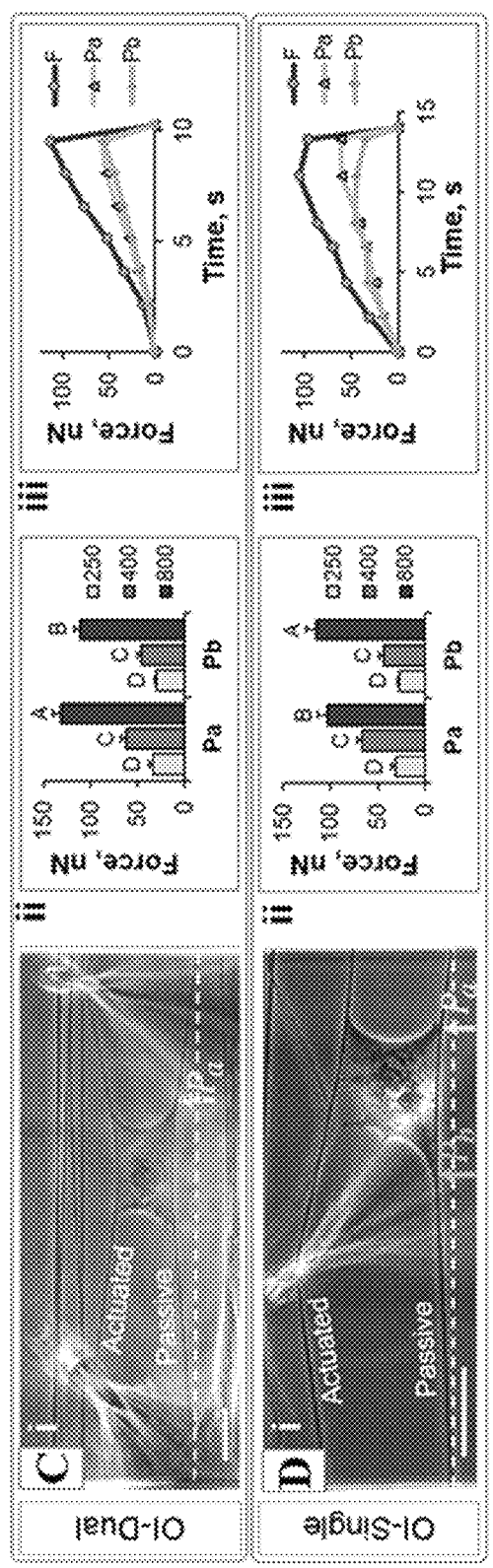
Fig. 9C-D

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: facilitates cellular adhesion

<400> SEQUENCE: 1

Tyr Ile Gly Ser Arg
1               5

NANOFIBER GRID AND RELATED METHODS

CROSS-REFERENCE TO RELATED APPLICATIONS

This application claims the benefit under 35 U.S.C. §119 (e) to U.S. Provisional Patent Application No. 62/100,500, filed on Jan. 7, 2015, which is incorporated herein by reference in its entirety.

The Sequence Listing associated with this application is filed in electronic format via EFS-Web and is hereby incorporated by reference into the specification in its entirety. The name of the text file containing the Sequence Listing is 1511243_ST25.txt. The size of the text file is 408 bytes, and the text file was created on Jan. 5, 2016.

Methods are provided herein for measuring single and multi-cell forces on a fused net of polymeric nano- and micro-fibers. Methods and systems are provided where single and multi-cells are attached to a net of polymeric nano- and micro-fibers and forces generated by the cells are observed and measured. Additionally, methods and systems for measuring cellular forces in response to external perturbations at high magnifications and in real time are described herein. Furthermore, diagnostic and drug testing platforms using the fused net of polymeric nano- and micro-fibers are described herein. Also provided herein are methods and apparatus including automated diagnostic and drug testing platforms using the fused net of polymeric nano- and micro-fibers.

Cells receive physical and chemical cues from their surrounding microenvironment known as the extracellular matrix (ECM), which consists of protein fibrils (30-70 nm in diameter), which can bundle into 200 nm-1 μm fibers, with composition and structure that varies temporally and spatially in the body [Alberts, B., et al., The Extracellular Matrix of Animals, Molec. Biol. of the Cell; Garland Science: New York, N.Y., 2002; Guilak, F., et al., Cell Stem Cell 2009; 5(1):17-26; Lock, J. G., et al., Semin. Cancer Biol. 2008; 18(1):65-76]. Mechanical communication between a cell and its substrate may occurs bi-directionally through integrin-mediated focal adhesions. Cells generate forces via actomyosin contractions which act on their surroundings (inside-out, IO) but also respond to forces originating outside the cell which are transmitted through adhesion sites to the cytoskeletal network (outside-in, OI) [Goldfinger, L. E. Integrin Signaling; 2nd ed.; Elsevier Inc., 2013; 2; Holle, A. W., et al., Curr. Opin. Biotechnol. 2011; 22(5):648-54; Eyckmans, J., et al., Dev. Cell 2011; 21(1):35-47; Chen, C. S., J. Cell Sci. 2008; 121(Pt20):3285-92]. Both directions are physiologically relevant, as seen in the example case of arteries where smooth muscle cells generate IO contractile forces which control vessel constriction to modulate blood pressure, but also experience OI forces from vessel expansion with each heartbeat that cause the cell to reorient actin stress fibers [Elson, E. L., et al., Exp. Cell Res. 2013; 319:2490-500; Chiu, J.-J., et al., Physiol. Rev. 2011; 91:327-87].

The influence of physical forces exerted or felt by cells on cell shape, cytoskeletal organization, and migration speed as well as disease onset is acknowledged and hypothesized to occur due to modulation of cellular IO forces in response to changes in the external fibrous environment or OI forces. Various force measurement techniques have been developed to probe single and multi-cell behavior. For example, IO forces can be measured by measuring the deformation using such as traction force gels or micropillar arrays [Ricart, B. G., et al., Biophys. J. 2011; 101(11):2620-28; Fu, J., et al, Nat. Methods 2010; 7:733-36; Sabass, B., et al., Biophys. J. 2008; 94(1):207-20; Rape, A. D., et al., Biomaterials 2011; 32(8):2043-51; Fukuda, Y. S., et al., Meas. Sci. Technol. 2011; 22(11):115802; Yang, M. T., et al., Adv. Mater. 2007; 19(20):3119-23; Raman, P. S., et al., Lab Chip 2013; 13(23): 4599-607]. Cells pull on the underlying substrate as they migrate, resulting in deflections which can be measured and converted to forces [Kamm, R., et al., Springer Handbook of Nanotechnology; Bhushan, B., Ed.; Springer Berlin Heidelberg, 2010; 1171-200]. Conversely, OI platforms require an active component that applies forces to the cell or its substrate. Such approaches include active stretching of traction force gels or micropillar arrays, AFM cantilevers, microfluidic devices that incorporate fluid shear, and other Conversely, OI platforms require an active component that applies forces to the cell or its substrate. Such approaches include use of AFM cantilevers, microfluidic devices that incorporate fluid shear, active stretching of traction force gels or micropillar arrays substrates, and a variety of MEMS devices [Nagayama, K., et al., Med. Eng. Phys. 2007; 29(5):620-28; Miyazaki, H., et al., J. Biomech. 2000; 33(1): 97-104; Lam, R. H. W., et al., Integr. Biol. (Camb). 2012; 4(10):1289-98; Christ, K. V. et al., Biomed. Microdevices 2010; 12(3):443-55; Das, T., et al., Lab Chip 2008; 8(8): 1308-18]. However, these methods are unable to capture the fibrous extra-cellular matrix (ECM) biophysical interactions, involving parameters of curvature, structural stiffness (N/m), alignment and hierarchy, which have been shown to play key roles in disease and developmental biology.

Force measurement platforms able to capture both IO and OI forces can distinguish forces that cells exert from forces that they can withstand, with applications in the investigation of disease models, such as, for example, disease states where progression from normal function to failure either occurs rapidly or without warning or detection, e.g., bone fracture, muscle or ligament tears, blood vessel aneurysms. In addition, force measurement platforms using scaffolds having characteristics similar to those of the ECM are particularly useful to probe single and multi-cell behavior.

Accordingly, there is a need for improved methods, apparatuses, and systems for the measurement of both IO and OI single and multi-cell forces using fibrous scaffolds having characteristics similar to those of the ECM. Also, there is a need for measurement platforms, which may be automated, that are capable of providing force measurements of single and multi-cells in various environments and configurations. Those and other advantages of the methods, apparatuses, and systems described herein will be described in more detail below.

SUMMARY

Methods and systems are provided for measuring single and multi-cell inside-out forces on a fused net of polymeric nano- and micro-fibers. Inside-out cell forces, or forces that cells can exert, that can be measured on a fused net of polymeric nano- and micro-fibers include attachment, migration, protrusion, division, apoptosis, differentiation, migration of leader cells, cell aspiration, debris forces, and drug response forces. These platforms may use automated processes for any step of the methods described herein, including analyzing cells. Optionally, the methods are computer-implemented methods for calculating inside-out forces of cells according to the methods described herein.

Methods and systems are provided for measuring single and multi-cell outside-in forces on a fused net of polymeric nano- and micro-fibers. Outside-in cell forces, or forces that cells can withstand upon an external perturbation, which may be symmetric or asymmetric, that can be measured on a fused net of polymeric nano- and micro-fibers include forces in response to single or multi-probe perturbation, force relaxation upon strain, cell-cell junctions, and drug response. The probes can be moved at prescribed strain rates and amplitudes with independent control. These platforms may use automated processes for any step of the methods described herein, including analyzing cells. Optionally, the methods are computer-implemented methods for calculating outside-in forces of cells according to the methods described herein.

In the methods of measuring single and multi-cell forces on a fused net of nano- and micro-fibers, a nanofiber grid comprising a plurality of high aspect ratio polymeric fibers is prepared, wherein the fibers are formed into a crossed pattern (at least one fiber crosses another fiber) and the fibers are fused where they intersect in the crossed pattern. The nanofiber grid is optionally coated with an adhesive coating. A single cell or cell type, or multiple cells or cell types are deposited on, or migrate onto the nanofiber grid where the cell or cells are in contact with at least one fiber of the nanofiber grid. The extent of deflection of the fiber in contact with the cell is measured using deflection sensing strategy including but not limited to optical microscopy, electron microscopy, or capacitive sensing leading to calculation of the corresponding forces acting on the displaced fiber.

Also provided are diagnostic and drug testing platforms using the methods of measuring single and multi-cell forces on a fused nanonet. These diagnostic and drug testing platforms may use automated processes for any step of the methods described herein, including analyzing cells. Optionally, the methods are computer-implemented methods for calculating inside-out and outside-in forces of cells according to the methods described herein.

The polymeric fibers can be formed from any useful polymer. Non-limiting examples of polymers include one or more of a polystyrene, a polyester, a polyurethane, a polyacrylamide, a poly(methyl methacrylate), a polylactic acid, a poly(lactic-co-glycolic acid), fibrinogen, collagen, and mixtures and copolymers thereof. Optionally, the method further comprises depositing adhesive proteins such as fibronectin, laminin, or collagen onto the fibers. The cells can be normal cells, diseased, or cancerous cells, the cells can be totipotent, pluripotent, or multipotent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a schematic representation of the preparation of a fused nanonet of polymeric nano- and micro-fibers using the non-electrospinning Spinneret based Tunable Engineered Parameters (STEP) technique with large diameter fibers (~1200 nm) spun with inter-fiber spacing (~200 μm) over a hollowed-out substrate, resulting in suspended fibers (a) and small diameter fibers (~400 nm) spun with spacing (~15 μm) perpendicular to the first layer (b).

FIG. 2 shows an optical image and SEM images of an assembled nanonet, in which fiber intersections are fused together, resulting in fixed boundary conditions.

FIGS. 9A-9E show (A) IO force measurement, showing i) representative parallel cell, ii) forces $P_a$ and $P_b$ for different fiber diameters ($F=P_a+P_b$), (B) schematic of IO and OI modes showing use of two point-load model and selection of locations for a and b, (C) OI-Dual platform, with i) representative optical image, ii) force distribution, and iii) representative force-time plot of abrupt breaking failure, (D) OI-Single platform, with i) representative optical image, ii) force distribution, and iii) representative force-time plot of peeling failure. Letters represent groups of statistical significance. N=242. (E) Schematic representations of i) probes, single or double, on either side of the cell, ii) probes, single or double, on either side of the cell offset by different distances, and iii) probes, single or double, on either side of the cell applying out of plane deflections.

DETAILED DESCRIPTION

Figure 3:
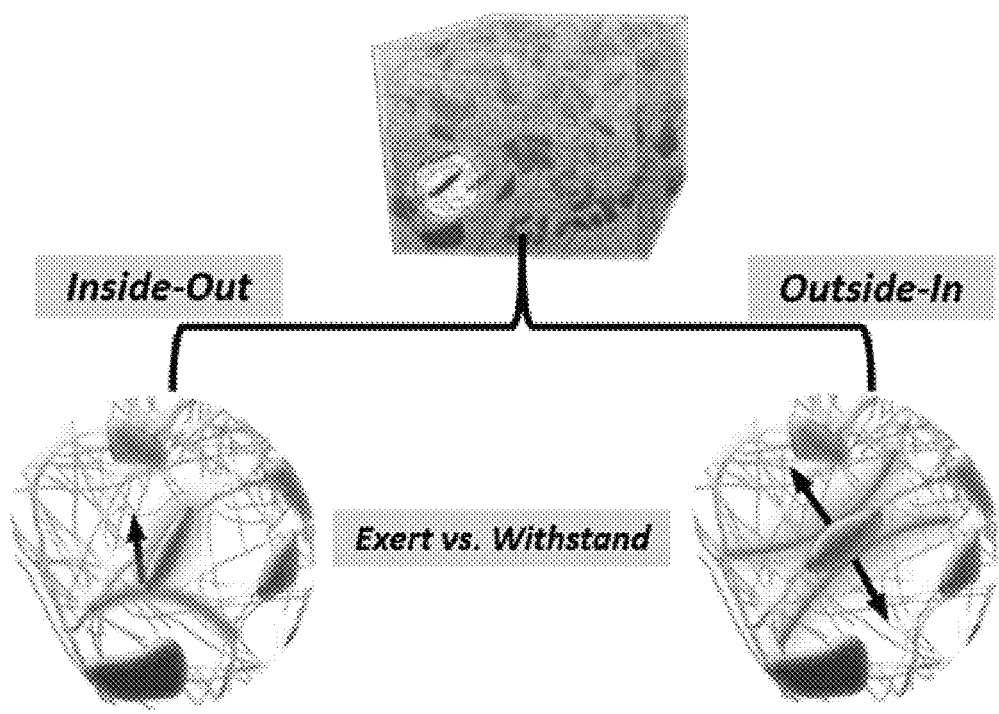
FIG. 3 shows a schematic representation of the IO and OI cell forces.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases As used herein, the terms "comprising," "comprise" or "comprised," and variations thereof, are meant to be open ended. The terms "a" and "an" are intended to refer to one or more. For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. Unless indicated otherwise, spatial orientation is used in relation to depictions of the embodiment only for ease of description and the described embodiments are not intended to have any specific spatial orientation, other than the respective position of elements of the embodiment in relation to each-other. It is to be understood that many alternative variations and embodiments may be assumed except where expressly specified to the contrary. It is also to be understood that the specific devices and embodiments illustrated in the accompanying drawings and described herein are non-limiting exemplary embodiments of the invention.

Described herein are methods for measuring single and multi-cell forces on a fused net of nano- and micro-fibers, e.g., polymeric fibers. Apparatus and systems are provided where single and multi-cells are attached to a net of nano- and micro-fibers and forces generated by the cells are observed and measured. Additionally, a platform for measuring cellular forces in response to external perturbations at high magnifications and in real time is described herein. Furthermore, diagnostic and drug testing platforms using the fused net of polymeric nano- and micro-fibers are described herein. Also provided herein are methods and apparatus including automated diagnostic and drug testing platforms using the fused net of polymeric nano- and micro-fibers.

In certain aspects of the methods and systems described herein, as shown in FIG. 1, fused scaffolds or nets made of polymeric nano- and micro-fibers may be prepared using the non-electrospinning Spinneret based Tunable Engineered Parameters ("STEP") technique, which was described in U.S. Pat. No. 9,029,149 and which is incorporated herein by reference in its entirety. This technique allows the preparation of polymeric nano- and micro-fibers with controlled diameter and orientation. Using this technique, the polymeric nano- and micro-fibers can be deposited or suspended in highly aligned configurations either in single or multiple layers with variable geometrical spacing between them, the aligned single and multi-layer fibers having diameters ranging from sub-50 nm to microns and several millimeters in length to form nanonets [Wang, J., et al., Langmuir 2014; 30(45):13641-9; Nain, A. S., et al., Polym. J. 2013; (45): 695-700; Nain, A. S., et al., Macromol. Rapid Commun. 2009; 30(16):1406-12].

FIG. 1a depicts deposition of thicker support fibers onto a frame using the STEP method. In that method a spinneret having a droplet of polymer at its tip is contacted with a first side of a frame. The droplet serves as an endless reservoir of polymer solution, and is replenished prior to its depletion. By this method, the droplet is contacted with the frame on its right side as shown in FIG. 1a, and the spinneret is then moved to the left side of the frame. The spinneret and/or the frame is moved using, e.g., a standard xyz stage. Movement of the spinneret and/or the frame relative to each-other results in the pulling of a high aspect ratio, uniform diameter fiber from the droplet. The STEP method permit pulling of extremely thin (50 nm in thickness or less), high quality, uniform fibers that cannot be produced by standard dry or wet spinning methods. Multiple parallel support fibers are deposited by moving the spinneret from one side of the frame to the other. FIG. 1b depicts deposition of multiple, parallel, thinner cross-fibers in the same manner. As indicated in U.S. Pat. No. 9,029,149, the polymer composition and its concentration in the solvent in the polymer solution control fiber diameter.

As used herein, the term "nanofiber grid", or "nanonet" refers to a scaffold that is prepared from nano- and micro-fibers. In one aspect, the fibers are polymeric, as can be produced, e.g., using the STEP technique as described herein. Using this technique, high aspect ratio polymeric fibers with controlled diameters are arranged in criss-cross (crossed) grids and fused at the fiber intersections (see FIG. 2) may be used to create suspended force measurement structures of tunable structural stiffness (in N/m). Fibers are typically circular in cross-section, but can have non-circular cross-sectional profiles, e.g., ribbon-like flat fibers. Reference to a diameter of a fiber is in relation to the fiber's smallest cross-sectional dimension.

In certain features of the methods and systems described herein, these nanonets, which possess characteristics similar to those of the ECM, can be seeded with single and multi-cells, e.g., mouse C2C12 cells, which allow cellular forces to be evaluated via Nanonet Force Microscopy, for example. As used herein, the term "Nanonet Force Microscopy (NFM)" refers to the technique using fiber deflections to calculate the forces exerted or felt by cells attached to nanonets. The properties of nanonets including elastic modulus and structural stiffness can be measured, e.g., as shown herein, using Atomic Force Microscopy (AFM).

Figure 4:
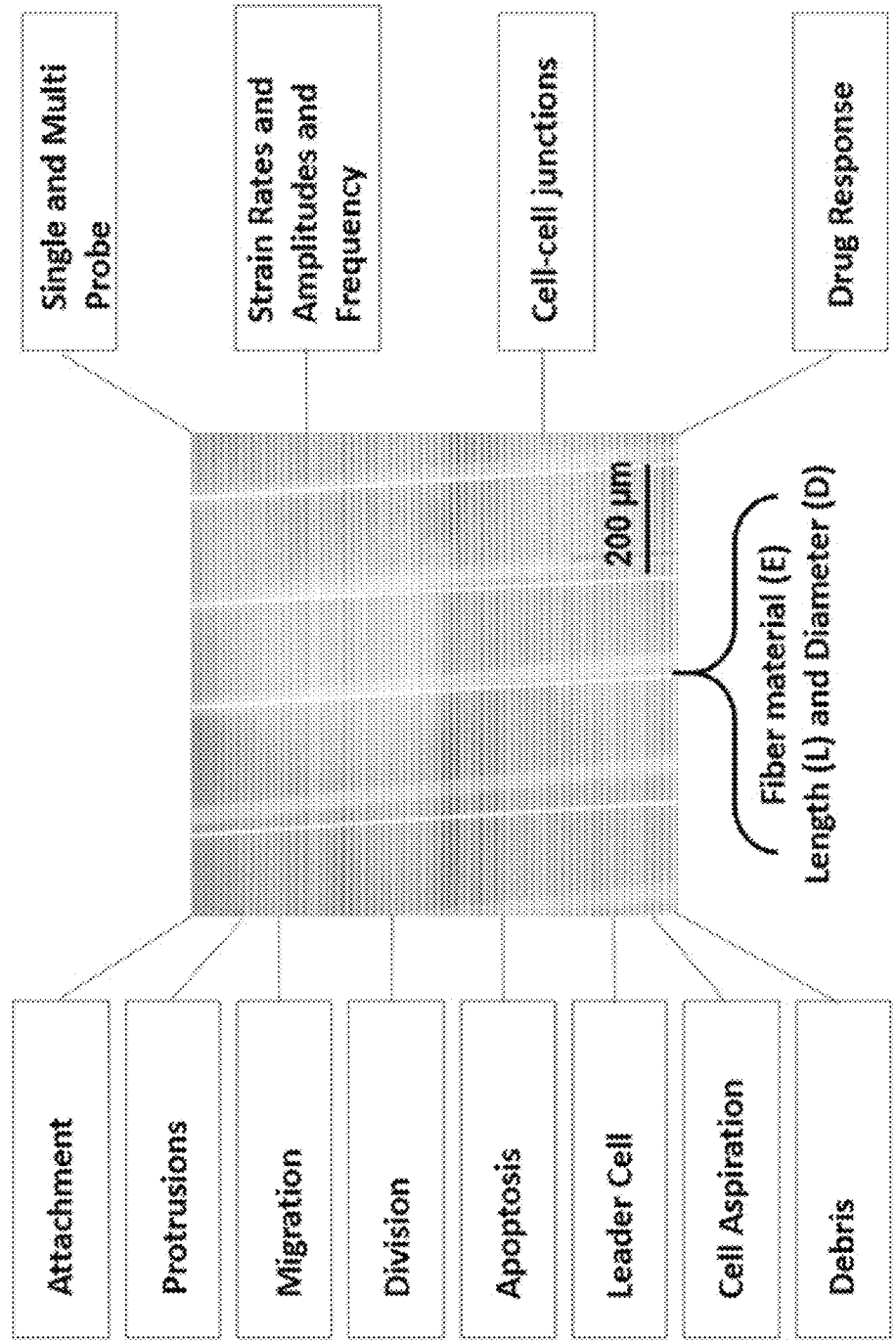
FIG. 4 provides examples of different IO and OI cell forces that can be measured on a nanonet that may have variable fiber material, length, and diameter.

In certain aspects of the methods and systems described herein, as shown in FIG. 3, cells may exert IO forces via actomyosin contractions and they may also withstand OI forces originating outside the cell which are transmitted through adhesion sites to the cytoskeletal network. In addition to observing contractile IO forces generated by cells attached to nanonet fiber segments (attachment, protrusions, migration, division, apoptosis, leader cell, cell aspiration, debris, drug response), external micropipette-based perturbation (symmetric and asymmetric) may be used to measure the cell's mechanical response, load distribution, and/or failure behavior (see FIG. 4). Perturbations of single cells and cell-cell pairs attached to nanonets of different diameters reveal that bias (asymmetric loading) does not affect the maximum adhesion force of the cell, but rather redistributes the forces within the cell in a diameter-dependent manner. These effects may be due to curvature-induced reorientation and redistribution of focal adhesion sites. This platform technology may be extended to measure (i) cell-cell junctional force response to external perturbation, revealing stronger adhesion formation at the cell-fiber interface than the cell-cell junction, (ii) single cell force response from the onset of exposure to drugs in various concentrations, and (iii) reduction in forces for cancerous glioma cells undergoing a blebbing-to-pseudopodial transition caused by physical stretching of the cell in the absence of drugs.

The non-electrospinning STEP technique allows to produce hierarchical assemblies of aligned nanofibers, to which single and multi-cell can be attached. Suspended fibers may provide cells with simultaneous 1, 2, and 3D mechanistic cues and are known to elicit changes in cell behaviors such as adhesion, migration, and cytoskeletal arrangement [Doyle, A. D., et al., J. Cell Biol. 2009; 184(4):481-490; Meehan, S., et al., Biophys. J 2014; 107(11):2604-11; Wang, J., et al., Langmuir 2014; 30(45):13641-9]. Nanofiber curvature induces cell elongation with associated focal adhesion clustering at the periphery of the cell, a phenomenon which is responsible for altered cell nucleus aspect ratio and migration speed on such substrates [Sheets, K., et al., Handbook of Imaging in Biological Mechanics 2014; 299-312; Sheets, K., et al., Acta Biomater. 2013; 9(7):7169-77]. Thus, cells attached to suspended fibers are able to sense and respond to changes in fiber curvature and structural stiffness as evidenced by alterations to focal adhesion cluster lengths.

The use of a suspended nanonet platform for measuring C2C12 mouse myoblast forces attached to fibers of three diameters (250, 400, and 800 nm) representing a wide range of structural stiffness (3-50 nN/μm) in connection with the NFM is developed to allow investigations in cell adhesion forces in response to symmetric and asymmetric external perturbation in single and cyclic modes at high magnifications in real time. The combined findings are two-fold: (i) contractility-based inside-out forces are evenly distributed at the edges of the cell, and that overall force magnitudes are dependent on fiber structural stiffness, and (ii) external perturbation in symmetric and asymmetric modes biases cell-fiber failure location, without affecting the outside-in forces of cell-fiber adhesion (FIG. 5). Further measured are forces of (i) cell-cell junctions, (ii) cyclic perturbation of single cells in presence of drugs, and (iii) cancerous single-cells transitioning from a blebbing to pseudopodial morphology.

According to one aspect of the methods described herein, using a highly aggressive glioma model (DBTRG-05MG), the platform technology using nanonets fused in crossed patterns manufactured using the non-electrospinning STEP technique serves to quantify single cell force modulation (both inside-out and outside-in) with and without the presence of a cytoskeleton altering drug (cytochalasin D) using suspended and aligned fiber networks (nanonets) beginning to represent the aligned glioma environment. This platform technology allows to measure contractile single cell forces exerted by glioma cells attached to and migrating along the fiber axis (inside-out). Further, the force response of glioma cells attached to two parallel fibers using a probe deflecting the leading fiber (outside-in) is measured. The forces are calculated using beam deflection within the elastic limit. It is shown that cytochalasin D compromises the spreading area of single glioma cells, eventually decreasing their 'inside-out' contractile forces, and 'outside-in' force response to external strain. The platform technology also allows for measuring changes in cell morphology, such as shape, area, etc. This technology allows the physiologically relevant aligned fiber networks used as ultra-sensitive force (~nanoNewtons) probes for investigating drug response and efficacy in disease models at the single cell resolution.

As used herein, a "polymer" is a compound formed by the covalent joining of smaller molecules, which are referred to herein as residues, or polymer subunits, when incorporated into a polymer. Unless specifically excluded, "polymers" include copolymers, which are polymers comprising two or more different residues, such as block-copolymers. Prior to incorporation into a polymer, the residues typically are described as monomers. Polymers can may have any topology, including, without limitation, straight-chain, branched-chain, star, dendritic, comb, etc. A non-limiting list of useful polymers in the methods and structures described herein includes: polystyrene (PS), polyester, polyurethane, polyacrylamide, poly(methyl methacrylate) (PMMA), poly(2-hydroxyethylmethacrylate) (polyHEMA), polylactic acid (PLA), poly(glycolic acid) (PGA), poly(lactic-co-glycolic acid) (PLGA), poly(caprolactone), polyaniline (PANI), polypyrrole (PP), etc. Polymers include conductive polymers and include the polymers listed above with conductive fillers such as carbon nanotubes, carbon black, metallic nanoparticles (e.g. gold). A non-limiting list of useful biological polymers include fibrinogen, hyaluronic acid, collagen, gelatin, elastin, and polysaccharides, such as cellulose, amylose, dextran, chitin, chitosan, glycosaminoglycans.

In certain embodiments, the polymers are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, scaffolds, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

In another aspect, the fibers are non-polymeric. Non-polymeric fibers useful in the methods and structures described herein include any metallic nanofiber, such as gold nanowire, platinum nano fiber, $SiO_2$, carbon fiber, etc.

According to one aspect, a nanofiber grid is provided. The nanofiber grid comprises high aspect ratio fibers and methods of preparing nanofiber grids comprising high aspect ratio fibers also are provided. In one non-limiting example, the scaffold comprises high aspect ratio fibers that can find use as a biological scaffold As used herein, the term "aspect ratio" refers to the ratio of the average length of fibers in a scaffold (L) and the average diameter of the fibers within the scaffold (D). The term "high aspect ratio" refers to an aspect ratio of L/D to be more than 200. For example and without limitation, fibers with an average diameter of 500 nm would have an average length more than 100 µm. In another non-limiting example, fibers with an average diameter on the nanometer scale should have an average length on the millimeter scale.

As used herein, "nanofiber grid" refers to a matrix of high aspect ratio fibers. The matrix can be of any useful geometry and orientation. For example and without limitation, the matrix can comprise nanofibers, a single layer of fibers, or multiple layers of fibers. In one non-limiting example, the matrix comprises fibers that are oriented generally parallel to one another. In another non-limiting example, the matrix comprises fibers that are oriented perpendicular to one another or criss-crossed. Depicted in FIGS. 1 and 2 are a non-limiting example of a scaffold, where the scanning electron micrograph shows generally parallel fibers with inset at higher magnification. In addition to scaffold fiber diameter and length, the fiber material properties (molecular weight, concentration) can be varied as described in U.S. Pat. No. 9,029,149 to obtain various control parameters. The control parameters disclosed herein for representative polymers, can be extended to other polymeric systems. In one aspect, the nanofiber grid comprises a plurality of spaced-apart support fibers having a thickness ranging from 1 µm to 100 µm, spanning a frame, and a plurality of crossing fibers, crossing the support fibers, having a thickness of from 50 nm to 1 µm, and spaced-apart at a distance that allows a mammalian cell to contact and attach to at least two adjacent fibers, for example ranging from between 10 µm and 100 µm.

In certain aspects, the support fibers are thicker than the cross fibers, for example in the range of from 1 µm to 100 µm in thickness, and when used, they act as anchors for the cross-fibers fused thereto. The cross fibers are of a thickness and composition such that under a typical force of a cell, or forces generated by the methods disclosed herein, the fiber is displaced a distance sufficient to permit calculation of the forces acting on the fiber. In one aspect, a cross-fiber deflects at least 2 µm and no more than 5% of its segment length between adjacent intersections with an applied force of 50 nano Newtons at a higher structural stiffness and 10 nano Newtons at a lower structural stiffness. In one aspect, polymer solutions mixed with fluorescent dyes form fibers with fluorescent dyes. In such a case, deflections of 20 nm, and possibly lower, can be detected. A fiber deflection of 100 nm corresponds to forces in the tens of pico Newton range ($10^{-12}$).

By "fused", in the context of crossed fibers of the nanofiber grid described herein, it is meant structurally connected, for example by melt-bonding or solvent bonding of crossed fibers of the nanofiber grid. A "grid", in the context of the nanofiber grid, refers to a crossed pattern on non-intersecting fibers, specifically the support fibers and the cross-fibers as described herein. Collectively, the support fibers are preferably parallel, meaning they do not cross in at least one portion of the nanofiber grid, and does not mean that that the fibers are perfectly geometrically parallel over their entire length. Likewise, the cross-fibers are preferably parallel, meaning they do not cross in the same portion of the nanofiber grid, and does not mean that that the fibers are perfectly geometrically parallel over their entire length. The support fibers may be perpendicular to the cross-fibers, meaning that the support fibers form a 90° angle or approximately 90° angle with the cross-fibers, but can form an angle of from 10° to 90°, or 45° to 90° with respect to the cross-fibers, including increments there between, including 10°, 20°, 25°, 30°, 40°, 45°, 50°, 60°, 70°, 75°, 80°, 85° and 90°.

The high aspect ratio fibers of the nanofiber grid can be prepared from any suitable high aspect ratio fibers, such as from metals, carbon fibers, inorganic materials or polymers. To facilitate visualization of certain fibers, for example with polymeric fibers, a label may be added to the polymer. A label can be mixed with a polymer solution prior to preparation of the fibers, or it may be coated onto or otherwise adhered to the fiber. Examples of labels include dyes, fluorescent dyes, and quantum dots. Other nanoparticles, such as radiopaque materials or carbon particles can be added to the fiber. In one aspect, a labeling composition is integrated into the polymer, for example by mixing a fluorescent dye, quantum dot or nanoparticle into a polymer solution prior to preparing the fibers of the nanofiber grid, or by coating the composition onto the fiber, optionally with a cell adhesion-promoting composition, for example by applying the composition to the fibers after they are formed. A label facilitates accurate visualization and measurement of fiber location and displacement.

In one aspect, the methods employ multiple cell types or cultures deposited on a single nanofiber grid. In another aspect, the methods employ a device comprising two or more discrete cell cultures at independently addressable physical locations, such as in a microfluidic device, an array or multi-well dishes, for example as are known in the art and are commercially available. In a multiwall device, cells are cultured on one or more nanofiber grids in a cell culture device with two or more wells, each well independently comprising a nanofiber grid. Where the device is a microfluidic device, the microfiber grid is placed inside the microfluidic device which contains cells, and media or hydrogel. The microfluidic device itself may be any useful configuration and in one aspect is constructed from biocompatible polymers that are liquid impermeable such as Polydimethylsiloxane (PDMS) or liquid permeable hydrogels such as Polyethylene glycol diacrylate (PEG-DA).

Figure 5A:
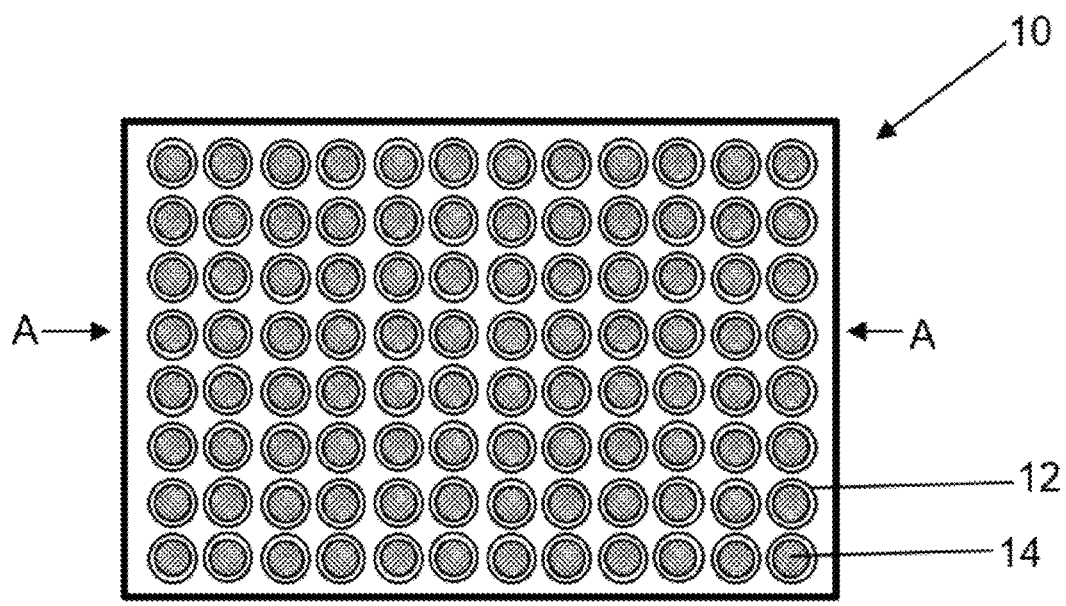
FIGS. 5A-5D provide various schematic views of a multi-well plate with nanofiber grid inserts.
Figure 5B:
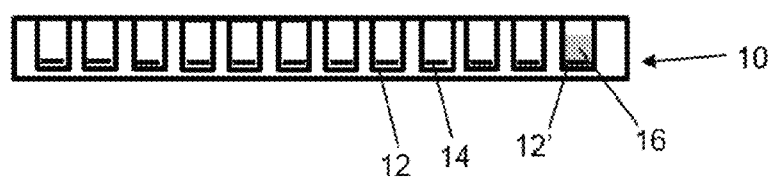
Figure 5C:
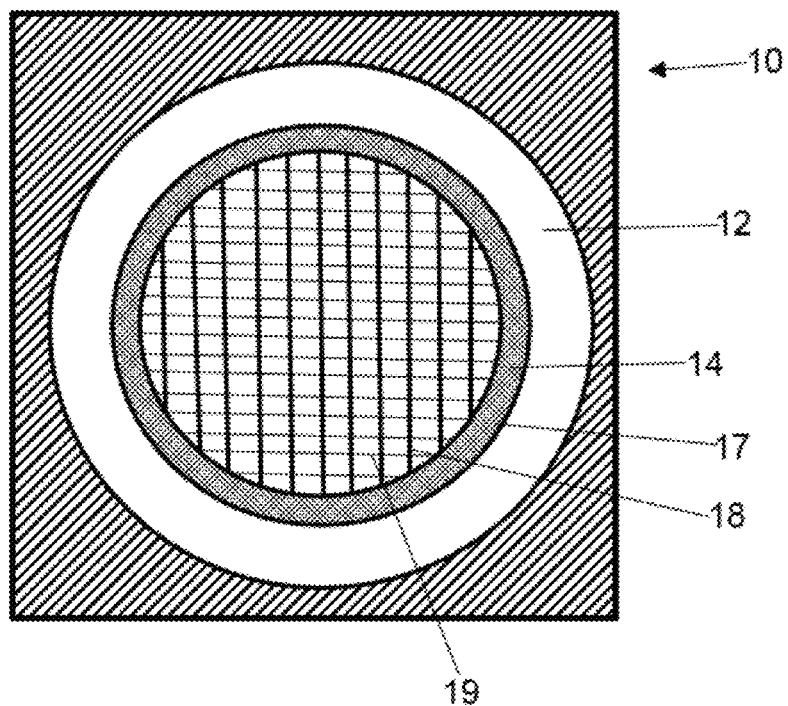
Figure 5D:
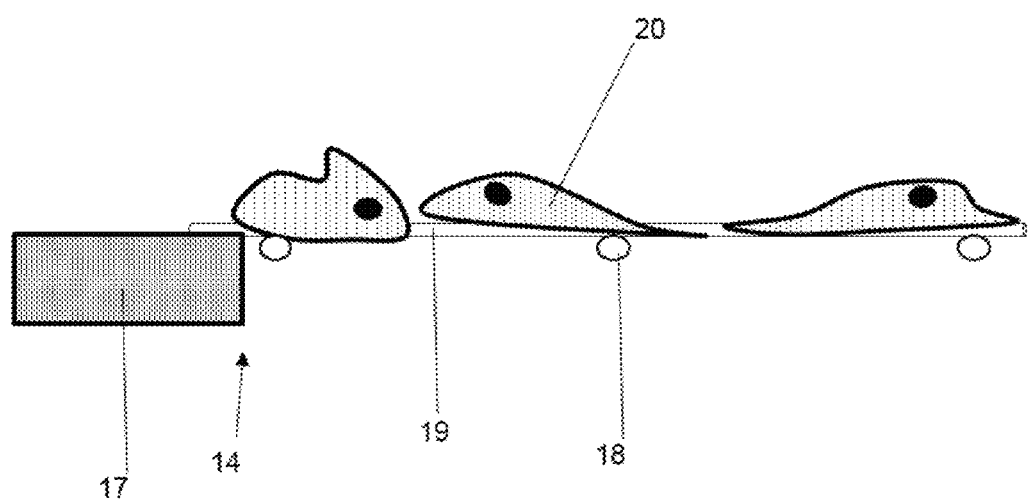

FIG. 5A is a top-view of a 96-well plate 10 having a plurality of wells 12, each containing a nanofiber grid structure 14. FIG. 5B is a cross-section of the 96-well plate 10 of FIG. 5A, showing the location of wells 12, nanofiber grid structures 14, and also depicting an aqueous medium 16 in one well 12'. FIG. 5C is a view of a single well 12 of plate 10, showing frame 17, thicker support fibers 18 and thinner cross-fibers 19 of the nanofiber grid structures 14. FIG. 5D is an elevation view of cells 20 deposited on thicker support fibers 18 and thinner cross-fibers 19 of the nanofiber grid structures 14. Thinner cross fibers 19 are attached to the frame 17.

Cells that are amenable to analysis by the methods include prokaryotic cells, eukaryotic cells, animal cells, fungal cells, plant cells, bacterial cells, protozoa cells, archaea cells, vertebrate cells, invertebrate cells, mammalian cells and human cells—including cell lines, chimera, and genetically modified (e.g., recombinant) versions of any of these cell types. In one aspect, cells useful in the methods described herein are eukaryotic and in many aspects, mammalian, for example human, and can be a cell line, a primary cell culture, or a specimen, such as a biopsy obtained, for example, from a tumor or a suspected tumor. Non-limiting examples of mammalian, for example human cells include myocytes, hepatocytes, neurons, cell precursors, such as cardiac stem cells, myoblasts, neuronal stem cells, mesenchymal stem cells, cancer cells, and recombinantly-modified cells.

In one non-limiting feature, the nanofiber grid is treated with (e.g., coated with, or otherwise combined with) a cell adhesion-promoting composition, to provide a biocompatible surface. For example and without limitation, the scaffold can be treated to provide a sterilized surface for proteins and/or cells. Non-limiting examples of sterilization treatments include: exposure to ultraviolet light; autoclave; exposure to high heat; irradiation, such as gamma irradiation; exposure to aseptic solvents, such as ethanol; and exposure to plasma. In another non-limiting example, the scaffold can be treated with an agent to provide for a biocompatible and/or cytocompatible surface. Non-limiting examples of agents include: proteins, such as collagen, vitronectin, laminin, fibronectin, fibrinogen, gelatin, and alginate; polymers, such as poly(ethylene glycol), poly(lysine), poly(ornithine); cell adhesion peptides, such as those incorporating RGD or YIGSR (SEQ ID NO: 1); and growth factors, such as one or more of: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

According to certain aspects of the methods described herein, cells are placed onto a nanofiber grid, in a suitable aqueous medium or hydrogel medium suitable for conducting the methods. An aqueous medium suitable for the methods described herein may be isotonic, hypertonic or hypotonic. The aqueous medium is a water-containing liquid composition comprising suitable ingredients for conducting the methods. Suitable ingredients include salts, sugars, amino acids, nutrients, buffers, vitamins, antibiotics, cellular extracts, rheology modifiers and/or animal serum, which can be used to maintain a cell, and for purposes herein can be any suitable composition, including normal saline, phosphate-buffered saline (PBS), cell culture medium (e.g., serum-containing or serum-free medium), etc., so long as cells can be deposited onto the nanofiber grid for purposes described herein and is consistent with the particular assay being conducted. A hydrogel is a water-swellable polymeric composition, and can be any composition, natural or synthetic, that does not interfere with the methods described herein. In use, nanofiber grid as described herein, may be used in any suitable vessel, such as a cell culture vessel, including plastic or glass vessels, such as flasks, plated, bottles, multi-well cell culture dishes, or any suitable container for culturing cells or tissue.

According to one aspect of the methods described herein, cells are grown on the nanofiber grid. As used herein, "growing cells" refers to maintaining cells in culture, including but not limited to adhesion, proliferation, migration, differentiation, and/or aggregation of cells.

Cells can be grown in culture media appropriate for growth and differentiation of any given cell type. Growth factors and cytokines, as are known in the art, can be used to induce cellular growth and differentiation. The choice of cells to propagate on the nanofiber grid depends on the intended use.

According to another aspect, the methods and systems as described herein are used in drug discovery and or analyte screening activities such as toxicity or efficacy screenings and titrations, and/or testing the activity of a composition, such as a compound, a biological sample, an environmental sample (e.g. a water or a soil sample), etc. Specifically, the method of measuring a cell force comprising: providing one or more cells on a nanofiber grid suspended in an aqueous medium or a hydrogel in a first vessel, wherein the nanofiber grid comprises a plurality of high aspect ratio fibers having diameters of between about 10 nm and 10 µm, wherein the fibers are formed into a crossed pattern having one or more intersections, and wherein the fibers are fused at the intersections of the crossed pattern, wherein at least one cell is in contact with a first fiber; measuring deflection of the first fiber in contact with the at least one cell; and calculating from the deflection of the first fiber a force applied to the fiber by the at least one cell, may further comprise adding one or more analytes, such as an active agent or a chemical, biological or environmental sample to the aqueous medium or hydrogel and determining deflection of the first fiber either at one or more time points prior to or after addition of the active agent to the aqueous medium or hydrogel, or compared to a control assay, e.g., a cell deposited on a second nanofiber grid in aqueous medium or hydrogel in a second vessel without addition of the analyte, or with the same or different concentrations of the analyte. The multi-well plate device depicted in FIGS. 5A-5D might be used for such a purpose, though other devices and systems, such as microfluidics systems, single-well plates, etc., can be effectively employed for drug discovery or analyte screening purposes, e.g., the screening of chemical compounds and chemical libraries for potential pharmaceutical activity. For example, the multi-well plate device described above can be used to analyze different analyte samples, including suitable control samples, in discrete wells of the multi-well plate device. As indicated herein, any step or steps of the process can be automated by suitable robotics, fluidics, electronics, optics, and computer processes, including the steps of depositing medium or hydrogel materials, cells, analyte(s), or any other ingredient used in the analysis process, as well as probe manipulation of the fibers where relevant, imaging of the microfiber grid.

Figure 6:
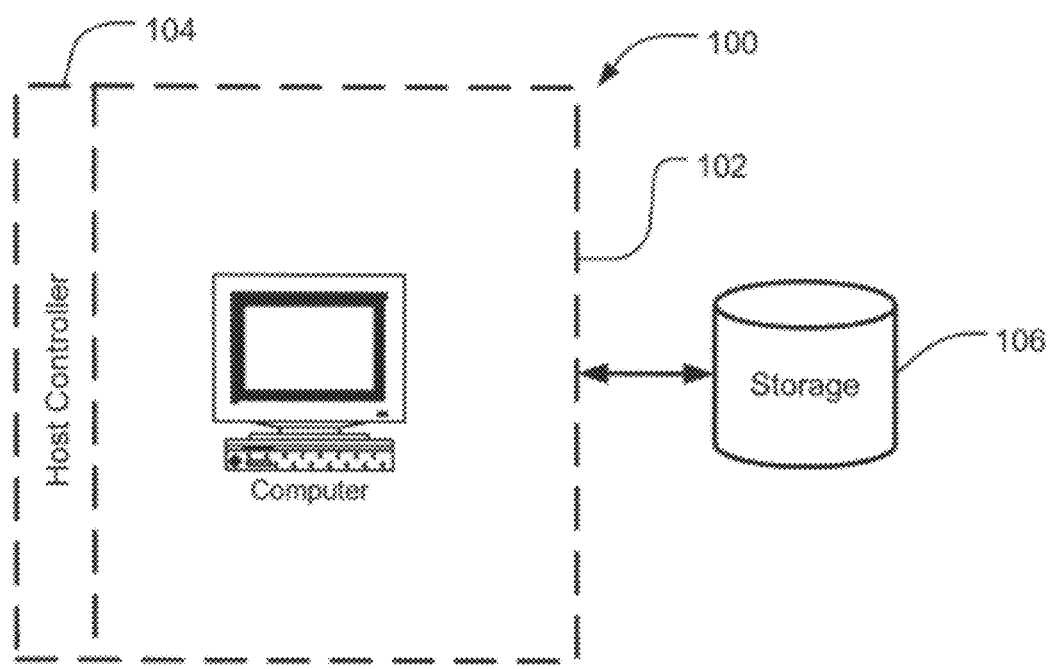
FIG. 6 depicts a computer system.

In one aspect, the methods described herein are implemented on a computing device (computer) as processes. In the context of computing, a process is, broadly speaking any computer-implemented activity that generates an outcome, such as implementation of a mathematical or logical formula or operation, algorithm, etc., for example by software (executable code) processed by a processor. FIG. 6 illustrates one embodiment of a system 100 for implementing a modeling system. The system 100 may include a device 102 operating under the command of a controller 104. Device 102 may be referred to herein, without limitation, as a computer or computing device. The broken lines are intended to indicate that in some implementations, the controller 104, or portions thereof considered collectively, may instruct one or more elements of the device 102 to operate as described. Accordingly, the functions associated with the modeling methods (e.g., processes, software, programs) described herein may be implemented as software executing in the system 100 and controlling one or more elements thereof. An example of a device 102 in accordance with one embodiment of the present invention is a general-purpose computer capable of responding to and executing instructions in a defined manner. Other examples include a special-purpose computer including, for example, a personal computer (PC), a workstation, a server, a laptop computer, a web-enabled telephone, a web-enabled personal digital assistant (PDA), a microprocessor, an integrated circuit, an application-specific integrated circuit, a microprocessor, a microcontroller, a network server, a Java™ virtual machine, a logic array, a programmable logic array, a micro-computer, a mini-computer, or a large frame computer, or any other component, machine, tool, equipment, or some combination thereof capable of responding to and executing instructions.

In one non-limiting embodiment, system 100 is implemented as a PC. Furthermore, the system 100 may include a central processing engine including a baseline processor, memory, and communications capabilities. The system 100 also may include a communications system bus to enable multiple processors to communicate with each other. In addition, the system 100 may include storage 106 in the form of computer readable medium/media, such as a disk drive, optical drive, a tape drive, flash memory (e.g., a non-volatile computer storage chip), cartridge drive, and control elements for loading new software. In embodiments of the invention, one or more reference values may be stored in a memory associated with the device 102. Data, such as images produced by the methods and systems described herein may be organized on computer readable media in a database, which is an organized collection of data for one or more purposes, usually in digital form Embodiments of the controller 104 may include, for example, a program, code, a set of instructions, or some combination thereof, executable by the device 102 for independently or collectively instructing the device 102 to interact and operate as programmed, referred to herein as "programming instructions". One example of a controller 104 is a software application (for example, operating system, browser application, client application, server application, proxy application, on-line service provider application, and/or private network application) installed on the device 102 for directing execution of instructions. In one embodiment, the controller 104 may be a Windows™ based operating system. The controller 104 may be implemented by utilizing any suitable computer language (e.g., C\C++, UNIX SHELL SCRIPT, PERL, JAVA™, JAVASCRIPT, HTML/DHTML/XML, FLASH, WINDOWS NT, UNIX/LINUX, APACHE, RDBMS including ORACLE, INFORMIX, and MySQL) and/or object-oriented techniques.

In one embodiment, the controller 104 may be embodied permanently or temporarily in any type of machine, component, physical or virtual equipment, storage medium, or propagated signal capable of delivering instructions to the device 102. In particular, the controller 104 (e.g., software application, and/or computer program) may be stored on any suitable computer readable media (e.g., disk, device, or propagated signal), readable by the device 102, such that if the device 102 reads the storage medium, the functions described herein are performed. For example, in one embodiment, the controller 104 may be embodied in various computer-readable media for performing the functions associated with processes embodying the modeling methods.

As used herein, and in the context of the described methods and structures, an image is a data structure that depicts, in any useful way, and at any useful wavelength. Images may be obtained, singly, in a continuous stream, as with a video camera, or multiple frames per second. Choice of imaging speed, timing, and the number of images obtained will be a matter of design choice, considering such factors as the number of images needed to, e.g., determine forces acting on a cell or applied by a cell, and as needed to monitor probe position, fiber deflection and any other activity, action, or result of such activities or actions. Images are obtained by any useful method and device, for example by charge coupled devices (CCDs), as are broadly known in the relevant arts. Because the cells are microscopic in nature, suitable microscopic optics (e.g., a microscope) are used to magnify the image to appropriate scale, for example as described below.

In certain aspects, the methods and devices described herein, are automated. Automation provides the ability to rapidly analyze multiple samples with Robotics useful in automating physical actions described herein, such as manipulation of a fiber to apply forces to a cell can be achieved by use of xyz stages or their equivalent under computer control. For example, a cell on a nanofiber grid can be located by imaging and image analysis. A fiber to which the cell is attached likewise can be readily identified by image analysis techniques. Placement of probes along the fiber, and applying force to the fiber, is achieved by use of the xyz stage, controlled by a computer process, and the application of force to the fiber is controlled by a computer process.

The amount of force applied by a probe to a fiber can be determined a number of ways. In one aspect, the force applied to the fiber is used as feedback to limit motion of the probe. In one aspect, the force sensor is included within the robotic device used to control the probe, for example by attaching a force sensor to the probe. In another aspect, the displacement of the fiber by the probe is used to determine the amount of force applied. In this aspect, the displacement of the fiber, and position of the probe is tracked by analyzing images of the fiber and probe. A person of ordinary skill can readily program suitable computer(s) and robotics, such as a xyz stage, to perform such image analysis and actions.

According to one aspect of the invention, a method is provided for measuring a cell force, that is an outside-in and/or an inside-out force as described herein. The method comprises depositing a cell on a nanofiber grid suspended in an aqueous medium in a vessel comprising a plurality of high aspect ratio polymeric fibers having diameters of between about 10 nm and 10 µm, wherein the fibers are formed into a crossed pattern having one or more intersections, and wherein the fibers are fused at the intersections of the crossed pattern, wherein the at least one cell is in contact with a first fiber; measuring deflection of the first fiber in contact with the at least one cell; and calculating from the deflection of the first fiber a force applied to the fiber by the cell. In one aspect, the cell is attached to multiple fibers; and calculating the deflections of multiple fibers to obtain the forces applied to multiple fibers.

Figure 7A:
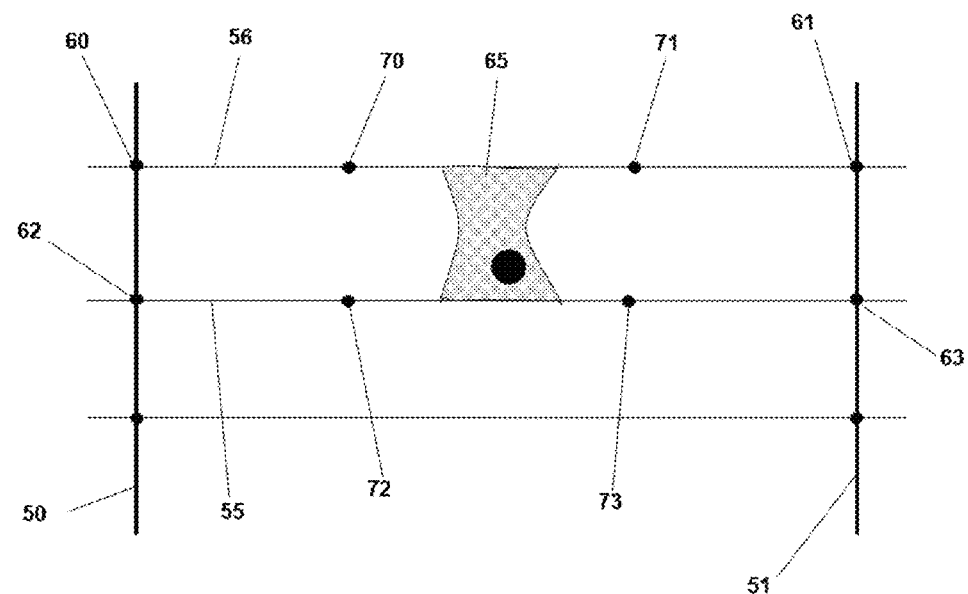
FIGS. 7A and 7B depict schematically a nanofiber grid with a cell and points of action of an external probe to produce OI forces on a cell.
Figure 7B:
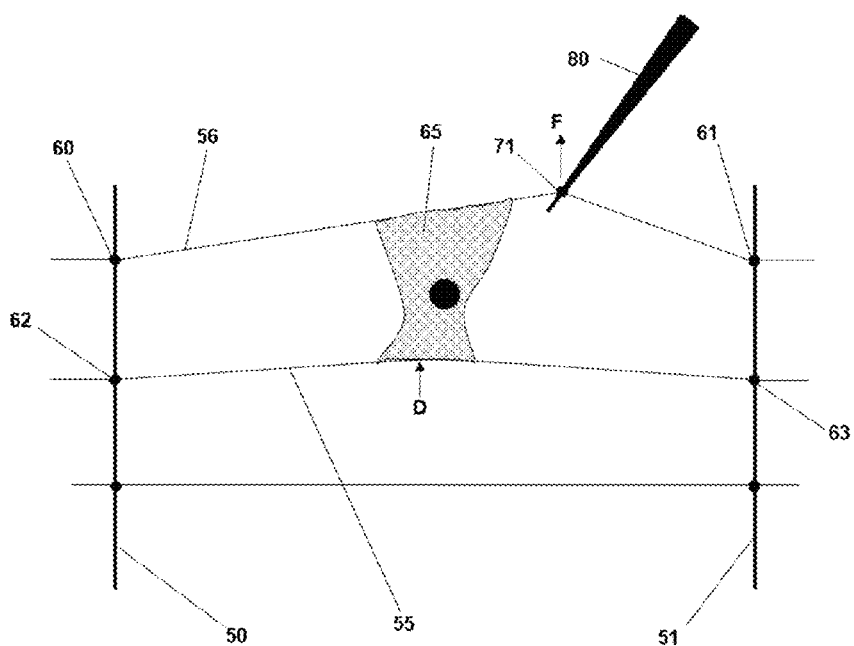

In one aspect, the cell is also attached to a second fiber, and the method further comprises, prior to measuring the deflection of the at least one fiber, moving a second fiber attached to the cell using a first probe placed at a point on the second fiber adjacent to the cell on a first side of the cell between the cell and a first intersection adjacent to the cell. The cell, as well as the points on the first and second fiber are located between two adjacent intersections (the closest intersections). A "probe" in the context of use to move one or more of the described fibers can be any rigid or semi-rigid structure able to move a fiber in a controlled manner, and which does not interfere with the operation of the described methods. A probe can be any material that does not perturb the operation of the described methods, and is therefore preferably non-reactive, and can be glass, ceramic, amorphous, polymeric, metallic, crystalline, carbon fiber, composite, etc. FIGS. 7A and 7B depict this aspect. In FIGS. 7A and 7B, support fibers 50 and 51 are depicted, as well as first cross-fiber 55 and second cross-fiber 56. Support fibers 50 and 51 are fused to cross-fibers 55 and 56 at intersections 60, 61, 62, and 63. A cell 65 is shown attached to cross-fibers 55 and 56. Additional support fibers and cross-fibers in the depicted nanofiber grid are not shown and/or labeled. Intersections 60 and 61 for second cross-fiber 56 are shown, and are indicated as being adjacent to cell 65 because they are the closest intersections to the cell 65. Likewise, intersections 62 and 63 for first cross-fiber 55 are shown, and are indicated as being adjacent to cell 65 because they are the closest intersections to the cell 65. Also depicted is a first point 70 on second cross-fiber 56 between the cell 65 and the adjacent intersection 60 on the second fiber 56. Also shown is a second point 71 on second cross-fiber 56 between the cell 65 and the adjacent intersection 61 on the second fiber 56, on an opposite side of the cell 65 as the first point 70. Also depicted is a first point 72 on first cross-fiber 55 between the cell 65 and the adjacent intersection 62 on the first fiber 55. Also shown is a second point 73 on first cross-fiber 55 between the cell 65 and the adjacent intersection 63 on the first fiber 55, on an opposite side of the cell 65 as the first point 72. In use, a probe is placed at one or both of points 70 or 71, and optionally also on one or both of points 72 and 73.

FIG. 7B shows the same nanofiber grid as in FIG. 7A, depicting movement of the second cross-fiber 55 at point 71, using probe 80. Probe 80 applies force, depicted by arrow F, to point 71, and thereby moves point 71 and displaces second cross-fiber 56 as shown. Because cell 65 is attached to the second cross-fiber 56 and the first cross fiber 55, movement of the second cross-fiber 56 displaces the first cross fiber 56 as shown by arrow D. In various aspects of the invention, the probe 80 can displace first cross-fiber so that cell 65 is not detached, or is wholly or partially detached from one or both of fibers 55 or 56, or the motion of the probe is reciprocating, moving the second cross-fiber 56 away from, and then towards first cross-fiber 55. Motion of the probe 80 and the first and second cross-fibers 55 and 56 is depicted as planar in FIGS. 7A and 7B, however, the fibers can move and be moved in three-dimensions, which is considered within the scope of the present invention.

Also disclosed herein is a computer-implemented method of converting the deflection forces of a high aspect ratio polymeric fiber in a crossed fused scaffold, the fiber being in contact with at least one cell, the method comprising, receiving, with at least one processor, a first image of the cell in contact with the fiber comprising deflection forces data relating to at least one first parameter of a plurality of parameters associated with the fiber; receiving or defining, with at least one processor, deflection forces data relating to the first image comprising at least one of the following: definition data, behavior data, direction data, spatial data, movement data, or any combination thereof; identifying, with at least one processor, at least one first rule from a rules database, the at least one first rule selected based at least in part based on the data relating to the at least one first parameter and/or data relating to the first image; generating, with at least one processor, a conversion of the deflection forces data related to the fiber by executing a calculation applying the at least one first rule to the data relating to the at least one first parameter, the deflection forces data relating to the first image, wherein the conversion generates a transformed image related to the first image and compares the first image and/or the transformed first image to at least one comparative image stored in an image database comprising one or more comparative images relating to the at least one first parameter; generating, using at least one processor, image-based output providing relating to structural stiffness data, based on the simulated progression and at least the first transformed image; and storing the first image, transformed first image, and the image-based output in the image database, such that future iterations of the predictive visual pathology model compare subsequent images to images in the image database, including the first image, and the transformed first image.

Also disclosed herein is a system for converting fiber deflection data into forces of a high aspect ratio polymeric fiber in a crossed fused scaffold, the fiber being in contact with at least one cell, comprising: an imaging device; and a computer connected to the imaging device comprising a processor and executable instructions for converting the fiber deflection data of the fiber to the forces from an image of the fiber and the at least one cell on the crossed fused scaffold, the executable instructions comprising: i. obtaining an image of an entire surface of the scaffold and the at least one cell from the imaging device; ii. producing from the image, using a computer-implemented method, a plurality of profiles of the positions of the fiber in contact with the cell; iii. calculating the deflection of the fiber using the profiles of the positions of the fiber in contact with the cell; iv. converting the deflection of the fiber into the force using a deflection equation for a beam; and v. producing an output from converting step iv. of the force on the fiber.

Example 1

Nanonet Scaffolds Manufacturing and Cell Culture

Polymeric solutions of polystyrene (Scientific Polymer Products Inc., Ontario, N.Y., $M_w$: 2×10$^6$ g·mol$^{-1}$) dissolved in xylene (Fisher Scientific, Pittsburgh, Pa.) at 14% and 5% (w/w) were prepared. Plastic coverslips (Fisher Scientific, Pittsburgh, Pa.) were cut to hollow frames and used as substrates. Suspended and aligned polystyrene (PS) nanofibers of varying diameters, spacing and orientation were deposited onto a rotating plastic hollow frame in criss-crossed patterns using the STEP platform at room temperature and 15% relative humidity. Using a custom solvent evaporation-based fusing method, the nodes of the criss-crossed patterned nanofibers were fused to form STEP nanonets with clamped boundary conditions. Scaffolds were placed in 35 mm glass-bottom dishes (MatTek Corp., Ashland, Mass.) and sterilized in 70% ethanol for 10 minutes. Fibers were coated in 2 µg/ml fibronectin (Invitrogen, Carlsbad, Calif.) to promote cell attachment [Dolatshahi-Pirouz, A., et al., ACS Nano 2010; 4(5):2874-82]. C2C12 mouse myoblasts (ATCC, Manassas, Va.) were cultured in DMEM cell culture media (Invitrogen) supplemented with 10% fetal bovine serum and 1% penicillin/streptomycin (HyClone Laboratories, Logan, Utah). Cells were seeded by placing 35 al droplets of 100,000 cells/ml on the scaffolds and 300 µl DMEM around the dish edges to prevent evaporation. After incubating 4 hours for attachment, 2 ml HEPES-buffered RPMI 1640 media (ATCC) was added to the dishes due to its ability to maintain pH longer than DMEM [Puech, P.-H., et al., Ultramicroscopy 2006; 106(8-9):637-44]. Cancer cell blebbing experiments were performed with DBTRG-05MG glioma cells using RPMI 1640 media (ATCC).

Example 2

Force Modeling

Figure 8:
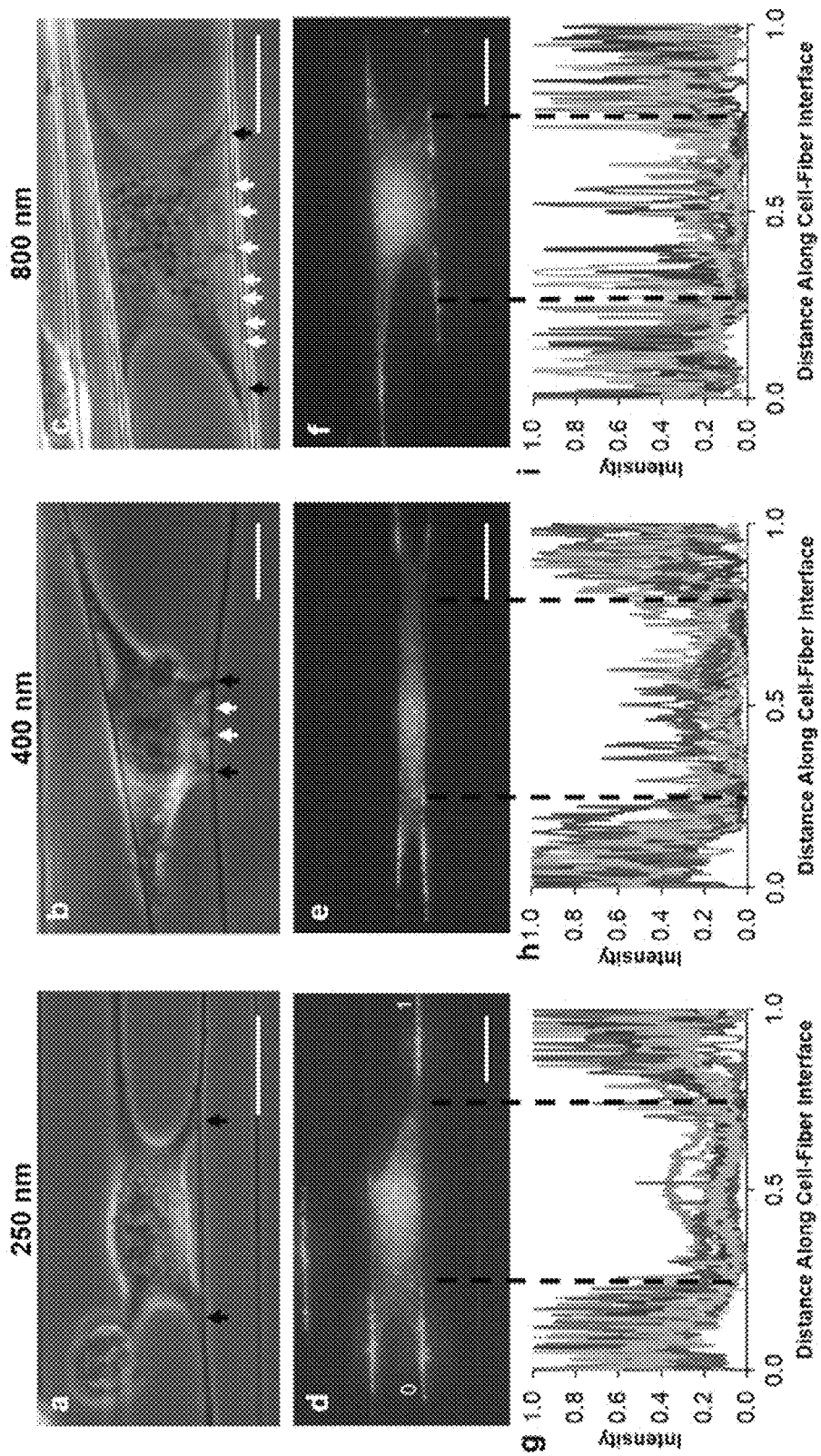
FIG. 8 shows the adhesion cluster distribution along the cell-fiber interface as a function of selected diameters. (a-c) are optical images of cells being pulled on 250, 400, and 800 nm diameter fibers, respectively, with the two primary peripheral clusters (black arrows) shown distinctly from intermediary groups (white arrows), which increase with increasing diameter, (d-f) are fluorescence images showing paxillin signal presence along the cell-fiber axis, (g-i) are corresponding intensity of the paxillin signal with primary cluster zones separated from intermediary zones by black dashed lines. As fiber diameter increases, signal intensity within this region increases as well (n=42). Scale bar is 25 μm.

The nanonets were modeled as a tie rod and the stiffness values were obtained using the deflection equation for a rod [Timoshenko, S., Strength of Materials, Part II Advanced Theory and Problems]. The fibers were modeled as prismatic beams under uniform tension with fixed-fixed boundary conditions. Cells apply forces through focal adhesion clusters, which are shown to be distributed at the poles of cell for cells attached to smaller diameter fibers and distributed along the length of cell-fiber interface for larger diameters (FIG. 8). Thus, force modeling can be developed for both conditions and a simple approximation for smaller diameter fibers includes assuming that a cell applies two point loads on the beam, one on each end of the cell-fiber interface (where the focal adhesions cluster) which both contribute to overall fiber deflection. Therefore, by modifying Timoshenko's single point load model to incorporate both point loads, the experimentally measured deflections $\delta_a$ and $\delta_b$ (FIGS. 9A-E) may be related to their associated loads $P_a$ and $P_b$ as follows [Timoshenko, S., Strength of Materials, Part II Advanced Theory and Problems, pp. 25-43].

After deriving equations for a beam under compressive load 'S', a negative sign is included to convert to a beam under tension. Assuming a hinged tie rod is held under compression and loaded perpendicularly to the fiber axis with a vertical single point load, P, the differential equations describing the deflection curve up to the location of the point load, c, and following the point load are:

$$EI\frac{d^2y}{dx^2} = -Sy - \frac{Pc}{l}x \quad (a)$$

$$EI\frac{d^2y}{dx^2} = -Sy - \frac{P(l-c)}{l}(l-x) \quad (b)$$

We then define:

$$\frac{S}{EI} = \lambda^2$$

The solutions to (a) and (b) are then:

$$y = C_1\cos\lambda x + C_2\sin\lambda x - \frac{Pc}{Sl}x \quad (c)$$

$$y = C_3\cos\lambda x + C_4\sin\lambda x - \frac{P(l-c)}{Sl}(l-x) \quad (d)$$

Boundary conditions are then applied considering there are no fiber deflections at the pinned ends of the strut:
From the boundary condition we know:
In the Eq. (c), x=0, y=0, we have, $$C_1 = 0$$

In the Eq. (d), x=1, y=0, we have, $$C_3 = -C_4 \tan \lambda l$$

The other two integration constants are achieved by recognizing deflection and slope continuity at the point of load application: x=l-c, $y_1=y_2$; $dy_1/dx=dy_2/dx$. From Eqs. (c) and (d), we have $$C_2 \sin\lambda(l-c) = C_4[\sin\lambda(l-c) - \tan pl \cos\lambda(l-c)]$$

$$C_2 \lambda \cos\lambda(l-c) = C_4 \lambda[\cos\lambda(l-c) + \tan\lambda l \sin\lambda(l-c)] + \frac{P}{S}$$

From which $$C_2 = \frac{P\sin\lambda c}{S\lambda\sin\lambda l}$$

$$C_4 = -\frac{P\sin\lambda(l-c)}{S\lambda\tan\lambda l}$$

Substituting the integration constants into (c) gives the equation for fiber position as a result of compressive loading, we obtain the deflection profile, $$y = \begin{cases} \frac{P\sin\lambda c}{S\lambda\sin\lambda l}\sin\lambda x - \frac{Pc}{Sl}x & (0 \leq x \leq l-c) \\ \frac{P\sin\lambda(l-c)}{S\lambda\sin\lambda l}\sin\lambda(l-x) - \frac{P(l-c)}{Sl}(l-x) & (l-c \leq x \leq l) \end{cases}$$

The above equation can easily be modified to describe a fiber under tension by changing the sign of S. Doing so changes $\lambda^2$ to $-\lambda^2$ as well, making $\lambda\sqrt{-1}=\lambda i$. Therefore, by substituting $-S$ and $\lambda i$ in place of S and $\lambda$ in the formulas obtained earlier, the formula for a beam under tension may be obtained. Recalling that:

$$\sin\lambda i = i \sin h\lambda, \cos\lambda i = \cos h p\lambda, \tan\lambda i = \tan h\lambda$$

The left-hand side (0≤x≤l-c) of the tie rod can be solved for:

$$y = -\frac{P\sinh\lambda c}{S\lambda\sinh\lambda l}\sinh\lambda x - \frac{Pc}{Sl}x$$

And the right-hand side (l-c≤x≤l):

$$y = \frac{P\sinh\lambda(l-c)}{S\lambda\sinh\lambda l}\sinh\lambda(l-x) + \frac{P(l-c)}{Sl}(l-x)$$

Having defined the deflection profile under a single point load, the two points load formula (as used to calculate forces on nanonets) may be obtained by superimposing a second load. The deflections at points a and b, $\delta_a$ and $\delta_b$, respectively, are ($P_b$ is at the left side of $P_a$)

$$\delta_a = \left(-\frac{P_a\sinh[\lambda(L-a)]}{S\lambda\sinh[\lambda L]}\sinh[\lambda a] + \frac{P_a(L-a)}{SL}a\right) -$$

$$\frac{P_b\sinh[\lambda(L-b)]}{S\lambda\sinh[\lambda L]}\sinh[\lambda a] + \frac{P_b(L-b)}{SL}a$$

$$\delta_b = -\frac{P_a\sinh[\lambda a]}{S\lambda\sinh[\lambda L]}\sinh\lambda(L-b)] + \frac{P_a(L-b)}{SL}a +$$

$$\left(-\frac{P_b\sinh[\lambda(L-b)]}{S\lambda\sinh[\lambda L]}\sinh[\lambda b] + \frac{P_b(L-b)}{SL}b\right)$$

with the dependent variables defined as follows:

TABLE 1

STEP Nanonet force microscopy model parameters (sample examples)

| Variable | Significance | Value |
|---|---|---|
| L | Segmental length of the fiber (distance between adjacent fixed ends) | Variable; 100-500 (μm) |
| a | Location of point load nearest to fiber-fiber intersection | 0 < a < L (μm) |
| b | Location of other point load | 0 < a < b < L (μm) |
| $\delta_a$ | Fiber deflection at a | Variable (μm) |
| $\delta_b$ | Fiber deflection at b | Variable (μm) |
| $\lambda$ | Shape-dependent mechanics parameter | $\sqrt{S/EI}$ (m$^{-1}$) |
| S | Uniform pre-tensional load | S = π(d$^2$/4) * T (μN) |
| T | Uniform pre-tensional stress, calculated from AFM residual stress measurements | 4.1 MPa for polystyrene polymer |
| d | Fiber diameter | 250, 400 and 800 nm |
| E | Elastic modulus of the polymer (polystyrene) | E = 0.97 (GPa) for polystyrene |
| I | Area moment of inertia | I = $\frac{\pi d^4}{64}$ (m$^4$) |

Example 3

AFM Characterization of Fiber Structural Stiffness

Force Measurements

Cells on suspended nanofibers tend to spread between two parallel fibers if the gap between the two fibers is approximately less than 20 μm [Sheets, K., et al., Acta Biomater. 2013; 9(7):7169-77; Sharma, P., et al., Integr. Biol. 2013; 5:1036-44]. Cells configured in this manner interact exclusively with two suspended fibers and not the underlying substrate, making the resulting isolation of cell-fiber interactions repeatable, convenient, and accessible to external perturbation. To increase the occurrence of this cell shape, large strut-like 1200 nm diameter fibers are spun at an average spacing of 200 μm and smaller diameter fibers are fabricated on top of and orthogonal to the previous layer with shorter inter-fiber spacing (~15 μm) (FIG. 1 a and b). Fiber intersections are then fused together (FIG. 2, ii white dotted circle and iii), ensuring fixed boundary conditions that allow the fibers to bend, and forces applied by cells are then calculated by measuring fiber deflection. Thus, scaffolds simultaneously encourage parallel cell configuration and allow for both IO observation and OI manipulation. In addition to having an elastic modulus (E, units: N/m$^2$), fibers present cells with structural stiffness (k, units: N/m) which accounts for the fiber diameter and position of cell along the suspended length. Three different diameters (250, 400 and 800 nm) were used in this study to obtain a wide range of curvature and structural stiffness values (3-50 nN/μm) as measured by AFM ramp tests [Nain, A. S., et al., IEEE Trans. Nanotechnol. 2006; 5:499-510; Meehan, S., et al., Biophys. J 2014; 107(11):2604-11].

Figure 10:
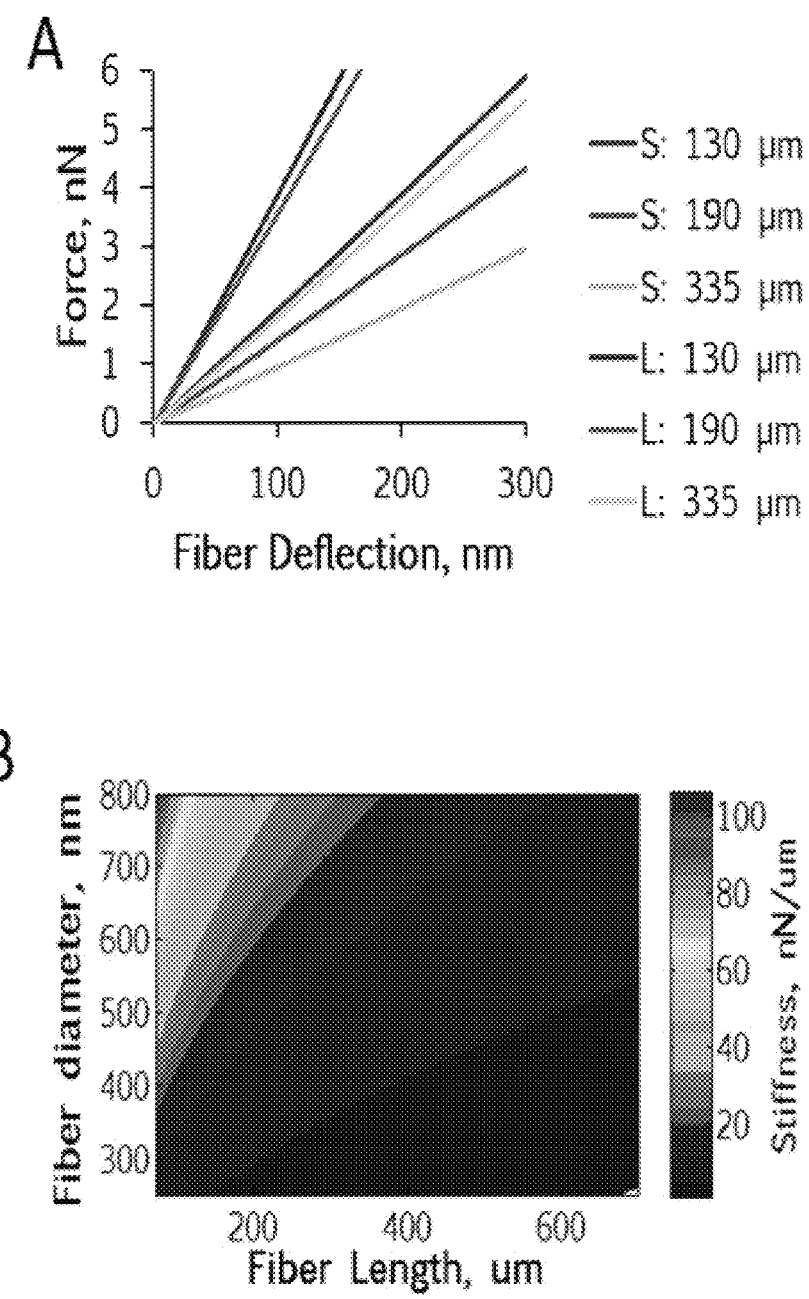
FIG. 10 shows (A) a graph of the slope of the AFM force-deflection curves are converted to stiffness values; the effect of fiber diameter (S: small (~250 nm, red), L: large (~500 nm, blue)) as well as fiber length (dark shading: ~130 μm, medium shading: ~190 μm, and light shading: ~335 μm) are seen by differences in slope and (B) mathematical modeled iso-stiffness lines demonstrating how a short, small diameter fiber can have the same stiffness as a long, large diameter fiber.

The structural stiffness values permit measurable deflection under cell-scale loads while remaining in the elastic limit [Carlisle, C. R., et al., Acta Biomater. 2010; 6:2997-3003; Gestos, A., et al., Polym. Test. 2013; 32:655-64]. Depending on the choice of fiber composition and the use of labels, deflection of 20 nm, or even lower, can be detected and analyzed using the methods described herein. For example, use of fluorescent dyes in the polymeric fibers facilitates analysis of fiber deflection. Fibers must have structural stiffnesses that are soft enough to permit appreciable deformation under single cell-scale loads that can be accurately measured optically while simultaneously remaining stiff enough to prevent plastic deformations [Carlisle, C. R., et al., Acta Biomater. 2010; 6:2997-3003; Gestos, A., et al., Polym. Test. 2013; 32:655-64]. Using AFM with tipless cantilevers, parametric evaluation of fiber properties on structural stiffness and associated modeling showed fiber structural stiffnesses acceptably ranged from ~5-20 nN/μm at the center of the fibers (FIG. 10). Due to the competing contributions of fiber length and diameter, it is possible to arrive at the same structural stiffness with a short, thin diameter fiber and a long, large diameter fiber, as shown by the overlapping red and blue lines in FIG. 10(A). Residual stress measurements achieved through AFM-based fiber breakage show that each fiber, independent of fiber diameter, carries 4.108 MPa residual stress as a result of the STEP spinning process. Therefore, the typically-used fiber diameter of 400 nm is assigned a constant pre-tension value of 0.54 μN, and this value increases for larger diameter fibers. This method is useful in measuring the structural stiffness of the fibers, which are then used in the equation. Other fiber structures can be characterized in this manner.

Example 4

Inside-Out (IO) Fiber Deflections Measure Measurement of Migration Forces

Materials and Methods
Probe Design and Operation

Figure 9A:
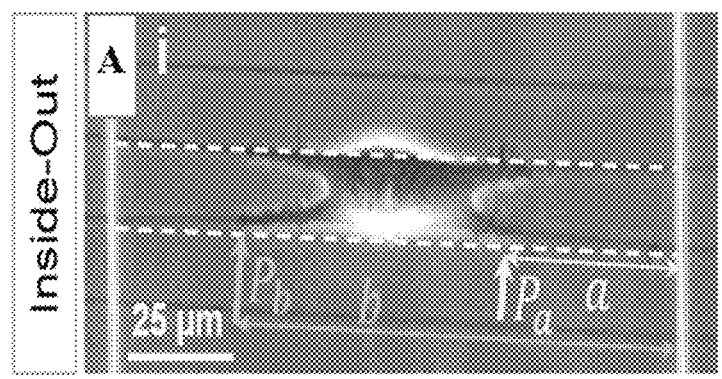
Figure 9A:
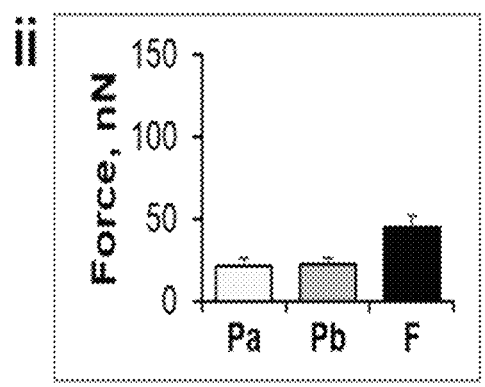
Figure 9B:
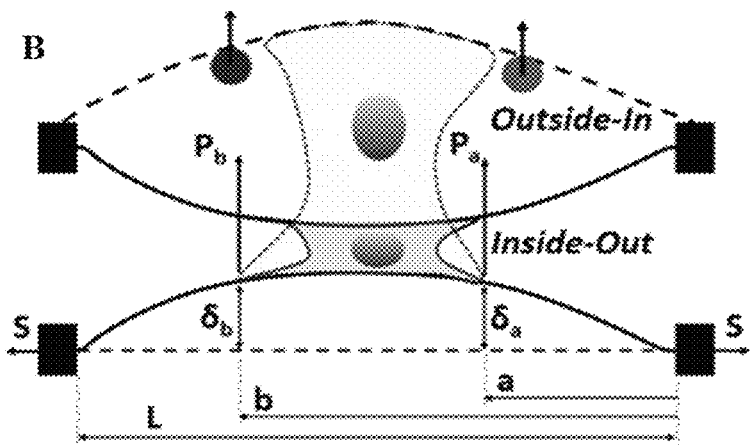
Figure 9E:
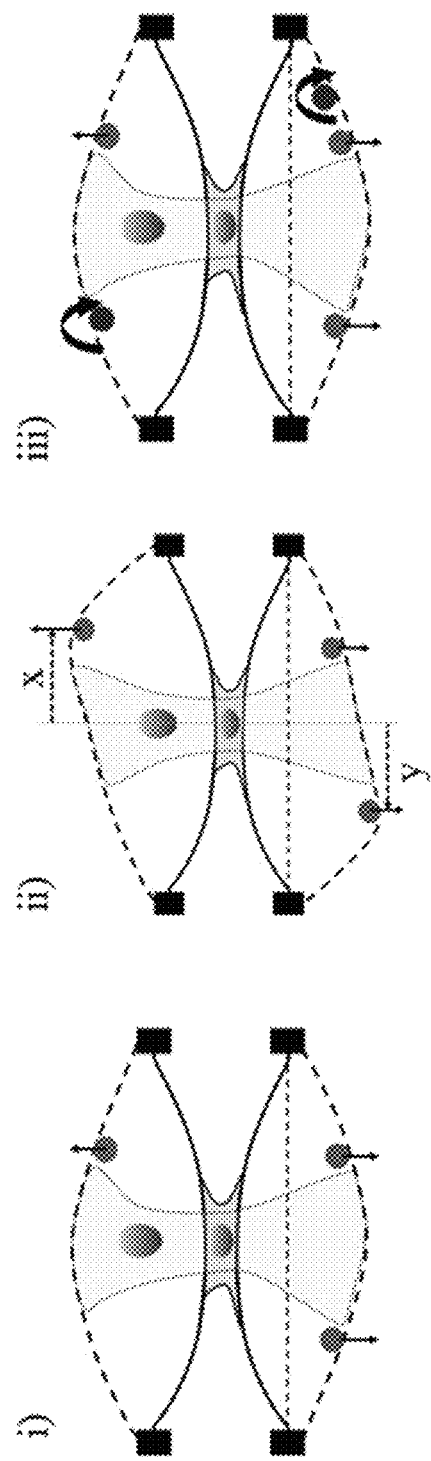
Figure 11:
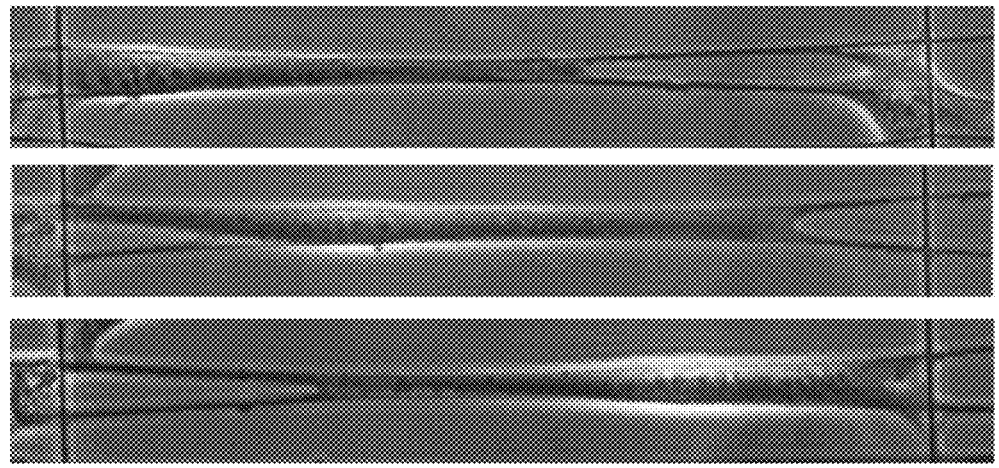
FIG. 11 shows optical images of a cell moving between two parallel fibers of a nanonet causing deflection of the fibers.
Figure 12A:
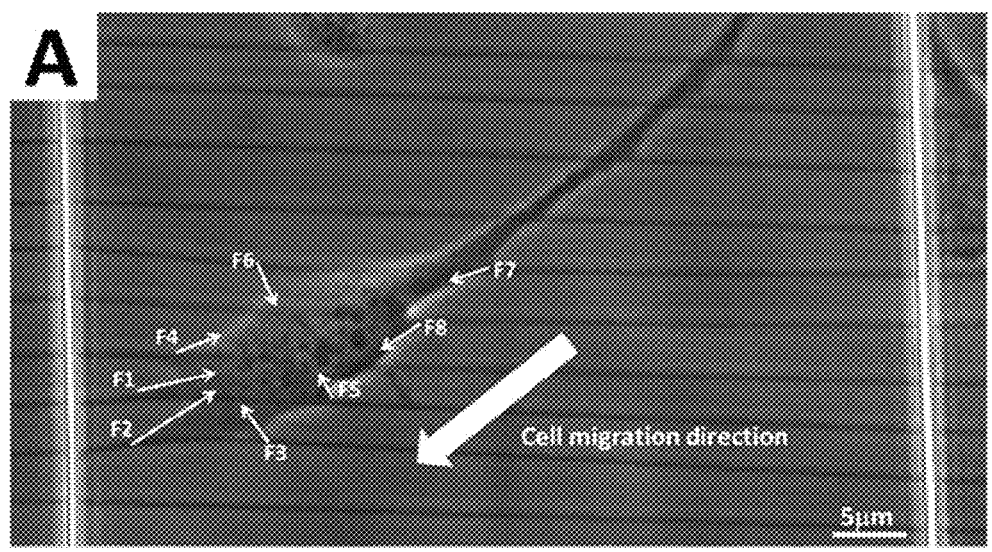
FIGS. 12A-D shows optical images of a cell moving in opposite directions (A and C) across the fibers of a nanonet causing deflection forces of the fibers, and the corresponding plots of force magnitudes (nN) vs. force number (B and D).
Figure 12B:
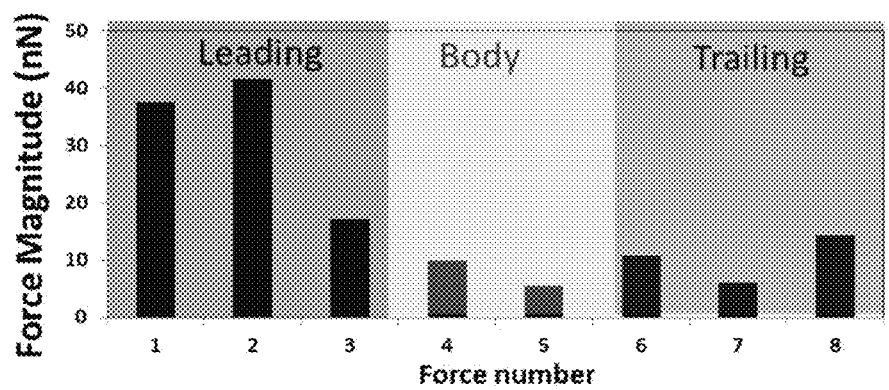
Figure 12C:
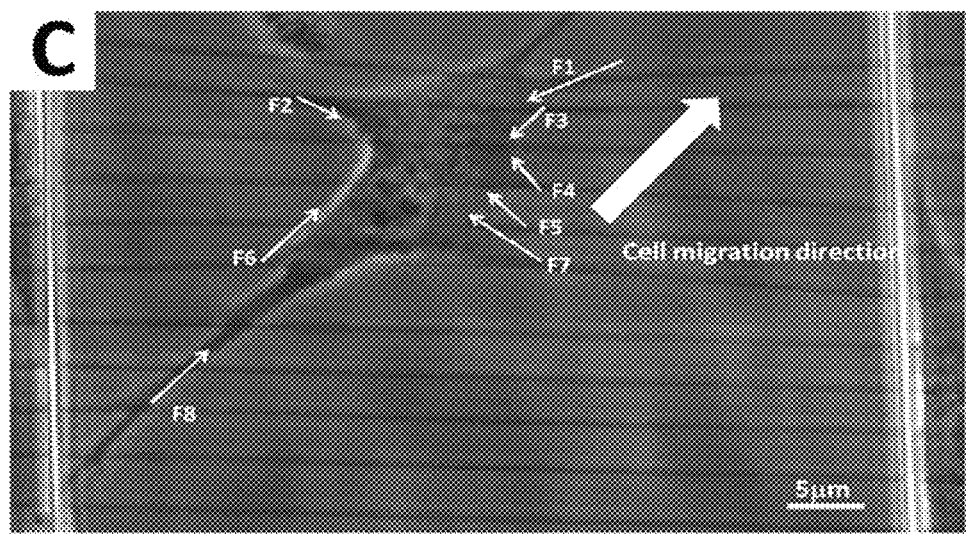
Figure 12D:
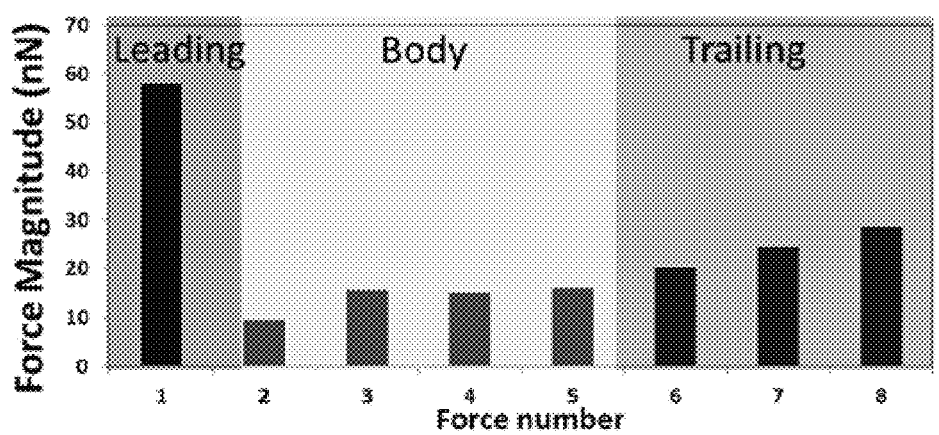
Figure 13:
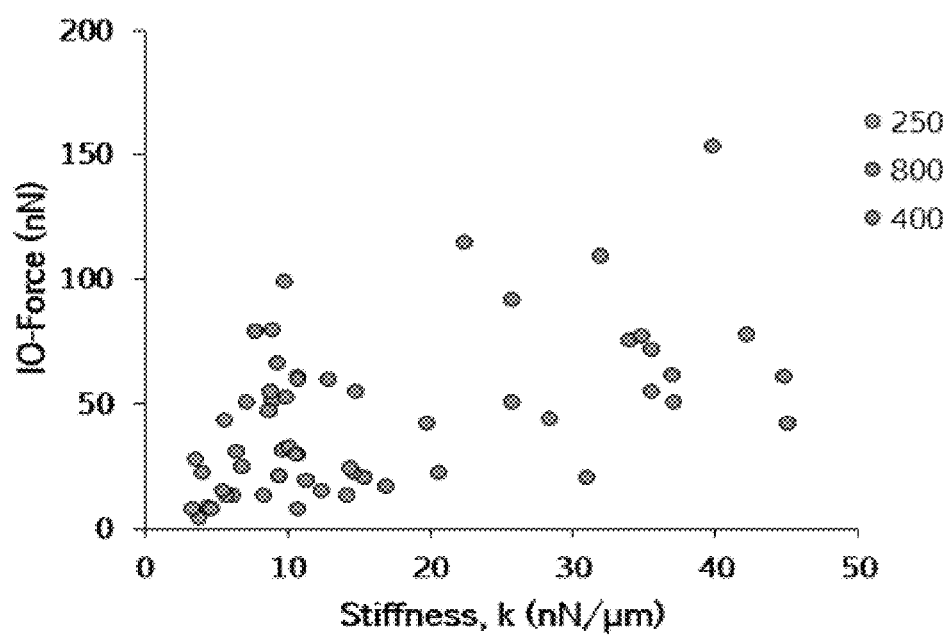
FIG. 13 shows plots of inside-out forces that cells exert on fibers vs. the fibers' structural stiffness at 3 different fiber diameters (250, 400, and 800 nm).

Micropipette probes were pulled to 1 μm diameter tips from 1.0 mm diameter capillary glass rods (Sutter, Novato, Calif.) using the P-1000 Flaming/Brown micropipette puller (Sutter). Using an MP-285 motorized manipulator (Sutter) probes were positioned near parallel-shaped cells and then pre-programmed for strain rate, end-state position, and number of cycles. A strain rate of 3 μm/s was used unless otherwise noted since it was the slowest rate at which cells did not exhibit viscoelastic effects.
Timelapse and SEM Imaging Nanonets were placed in an incubating microscope with a digitally-controlled 3-axis stage (Zeiss AxioObserver Z1). Time-lapse movies were created by capturing still images approximately once per 600 ms. Both 20× and 40× images were captured with a Zeiss AxioCam MRm camera. Data was analyzed using AxioVision® software (Zeiss) and ImageJ® (NIH).
Statistical Analysis Sample populations were tested for statistical significance using student's T-test in JMP 11 software. A p-value ≤0.05 was used (unless otherwise noted) to determine significant differences. Error bars represent standard error unless otherwise noted. Values are reported as average±one standard error.
Results As cells attach and spread between two parallel nanonet segments (FIGS. 9A-E), individual fibers deflect (FIG. 9A(i)). Migration of cells may also occur across several fibers of a nanonet (FIGS. 9A-D). The resulting fiber deflections can be used to calculate forces. FIGS. 9B and 9D show the variation of the force magnitude in function of the location of the deflection with higher force magnitude on the leading edge. In addition, cells, which attach and spread between two parallel nanonet segments, form cell-fiber adhesion clusters in two separate locations at the periphery of the cell [Sheets, K., et al., Acta Biomater. 2013; 9(7): 7169-77]. Accordingly, by comparing with OI deflections, the distributed load as a single load at both cell peripheries on the trailing passive fiber can be approximated. FIGS. 9A-D show locations a and b with associated loads $P_a$ and $P_b$, assigned such that a and its associated load $P_a$ are located nearest to the fixed fiber intersection. Doing so makes location b synonymous with the probe side in OI-single, which makes location a the side of the cell that is opposite from the probe's actuation. 49 C2C12 cells were recorded and their associated IO fiber deflections at a and b and calculated the forces exerted by cells at $P_a$ (21.6±3.9 nN) and $P_b$ (22.3±2.7 nN) (FIG. 9A(ii)). The two point loads can then be represented by an equivalent single point load ($P_{resultant}$) at an intermediate location located at the geometrical center of the cell (45.0±5.4 nN). Comparing $P_a$ and $P_b$, it is seen that forces are essentially equally distributed across the cell. Furthermore, IO forces were also found to be dependent upon fiber structural stiffness, a trend similar to both micropillars of varying pillar stiffness and flat substrates with tunable modulus of elasticity (E, units: $N/m^2$) [Murphy, W. L., et al., Materials as Stem Cell Regulators. 2014; 13; Han, S. J., et al., Biophys. J. 2012; 103:640-648]. FIGS. 11, 12A, and 12C show SEM images of cells moving between two parallel fibers and in opposite directions across the fibers of a nanonet causing deflection forces of the fibers, and the corresponding plots of force magnitudes (nM) vs. force number (12B and 12D). FIG. 13, which shows plots of the inside-out forces that cells exert on fibers vs. fiber structural stiffness, reveals that cell forces increase on stiffer fibers. For instance, cells attached to smaller fibers (250 nm) only exerted an average IO force of 16.0±4.2 nN, whereas those on larger 800 nm fibers exerted 67.9±9.4 nN.

Figure 14A:
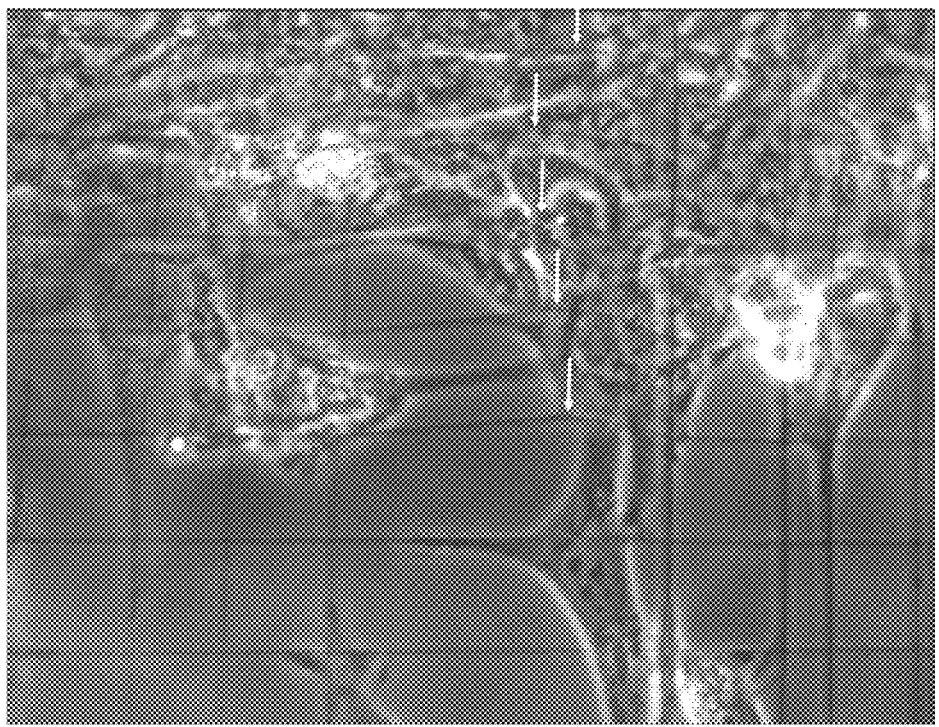
FIGS. 14A-C show optical images of multi-cell migrations observed on nanonets.
Figure 14B:
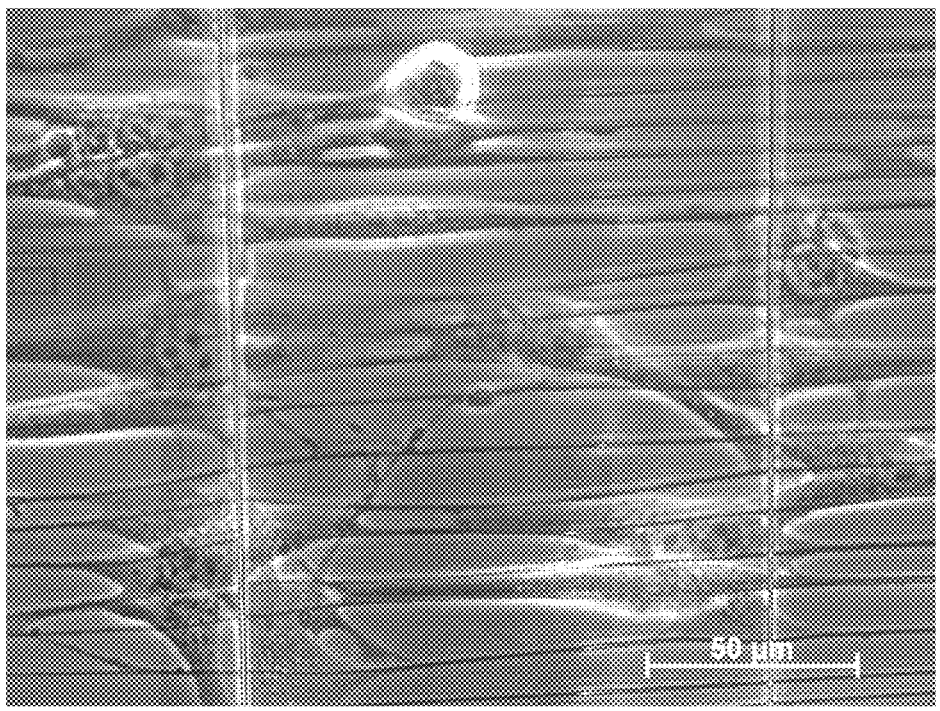
Figure 14C:
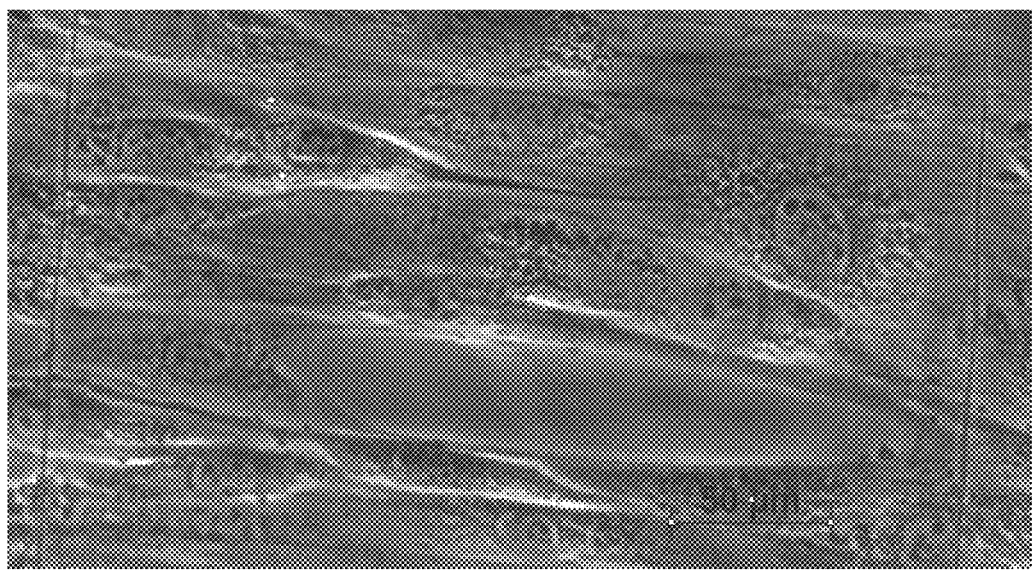

According to another aspect of the methods described herein, multi-cell (collective) migrational forces can also be measured using the corresponding fiber deflections to calculate these forces. FIGS. 14A-C show optical images of multi-cell migrations observed on nanonets. These multi-cell migrational forces can be used for wound healing.

Example 5

Inside-Out (IO) Fiber Deflections Measurement of Protrusion Forces

A suspended fiber platform that enables investigation of protrusion sensitivity to fiber curvature contrasts at high spatiotemporal resolution, while being independent of whole cell body migration. By manipulating the diameter of suspended fibers in orthogonal directions, we constrain cell migration along low curvature-large diameter (2 μm) fibers, while solely allowing cells to sense, initiate, and mature protrusions on orthogonally deposited high curvature-low diameter (~100, 200 and 600 nm) fibers. Using highly aggressive breast and brain cancer cell lines, breast cell line protrusion maturation dynamics were found to be more sensitive to changes in fiber curvature compared to brain.
Materials and Methods
Fiber Manufacturing Polystyrene nanofibers were fabricated using previously reported Spinneret-based Tunable Engineered Parameters (STEP) technique. Using user-defined inputs, the support fiber diameter was made to be 2-3 μm in diameter. Protrusive fibers were formed with diameters of 94.2±70.1 nm (small), 202.1±53.0 nm (medium), and 564.8±231.4 nm (large). Fibers were deposited and suspended on polystyrene frames with 4 mm by 4 mm squares cut out of 6 mm by 6 mm sheets. Fiber samples were then treated with an in-house solvent fusing method which connects crossing fibers at their intersections to create a unified fiber network. Samples were then fixed with vacuum grease to glass-bottom six-well plates (MatTek Corp). Fixed samples were then coated with varying concentrations of fibronectin (2 µg/ml, 4 µg/ml, and 16 µg/ml). Fibers were coated for 3 hours prior to seeding.

Cell Seeding and Culture

MDA-MB-231 (mammary ductal adenocarcinoma) cells were cultured in L-15 medium with 10% FBS and 1% penicillin. DBTRG-05MG (glioblastoma multiforme) cells were cultured in RMPI-1640 medium with 10% FBS, 1% penicillin/streptomycin, 30 mg/L L-proline, 35 mg/L L-cystine, 3.57 g/L HEPES, 15 mg/L hypoxanthine, 1 mg/L adenosine triphosphate, 10 mg/L adenine, and 1 mg/L thymidine. Cultures were maintained in incubator at 5% $CO_2$ and 37° C. Samples were seeded with a seeding density of 300,000 cells per ml where only a fraction would attach to fibers depending on fiber diameter and fibronectin concentration. The majority of cells rested on the glass bottom below the samples for the duration of the experiment. Samples were maintained in well plates with 2 ml per well of their respective growth medium once cell-fiber attachment was observed.

Time-Lapse Microscopy and Analysis

Samples were imaged with Carl Zeiss microscope (AxioObserver Z.1 with mRm camera) equipped with incubator within the glass-bottom six well plates. The incubator was maintained at 5% $CO_2$ and 37° C. Time-lapse videos were taken at a magnification of 40× with a frame imaged every minute for 6 hours. Videos were analyzed by hand using measurement tools on the Carl Zeiss Axiovision software.

Immunostaining and Imaging

Cells were fixed while attached to nanofiber samples using 4% paraformaldehyde. Cells were permeabilized by soaking samples in permeabilization solution (0.1% Triton-X-100 in PBS) for 15 minutes. Samples were then immersed in blocking buffer (5% goat blocking buffer) for 30 minutes. Primary antibodies were diluted in antibody dilution buffer (Triton-X-100 and BSA) at the following dilution ratios: vimentin mouse monoclonal antibody (1:100), α/β-Tubulin antibody (1:100), paxillin rabbit polyclonal antibody (1:250). Secondary antibodies were diluted in antibody dilution buffer and added at the following dilution ratios: Alex Fluor 405 Goat Anti-Mouse (1:100) and Alexa Fluor 488 Goat Anti-Rabbit (1:100). Rhodamine Phalloidin was also diluted in antibody dilution buffer with a dilution ratio of 1:100. All stains were imaged using immunofluorescent microscopy with Carl Zeiss microscope. All stained samples were imaged with a 63× objective lens. Intensity plots were created using ImageJ.

Statistical Analysis

All data was analyzed for statistical significance using GraphPad software. One, two, and three stars on plots represent $p<0.05$, $p<0.01$, and $p<0.001$, respectively. All error bars show standard error.

Results

MDA-MB-231 (breast) and DBTRG-05MG (glioblastoma) metastatic cell lines, which are both highly invasive and display aggressive phenotypes, were examined using the non-electrospinning STEP technique to fabricate fused and suspended nanofiber networks in a two layer system with high control of fiber alignment, diameter, and orientation, with fibers coated with fibronectin which is native to both breast and neural tissue. By testing various diameters and fibronectin concentrations, the platform presented in this study addresses the heterogeneity of the tumor microenvironment and probes its effect on cancer cell protrusive behavior. For the first design, we constructed an evenly spaced grid of fibers, each with a diameter around 2 am, that were fused at their intersections. As the cells migrated along the described fiber networks, they eventually encountered intersections between two crossing fibers of equal diameter. At these locations, cells were observed to form broad and non-fluctuating protrusions along the fiber surfaces without bias in either fiber direction. On this homogenous fiber diameter system, a cell protruding in a new direction was followed by the net migration of the entire cell body. Therefore, this initially designed fiber network failed to show protrusions independent from the migratory direction.

Figure 15A:
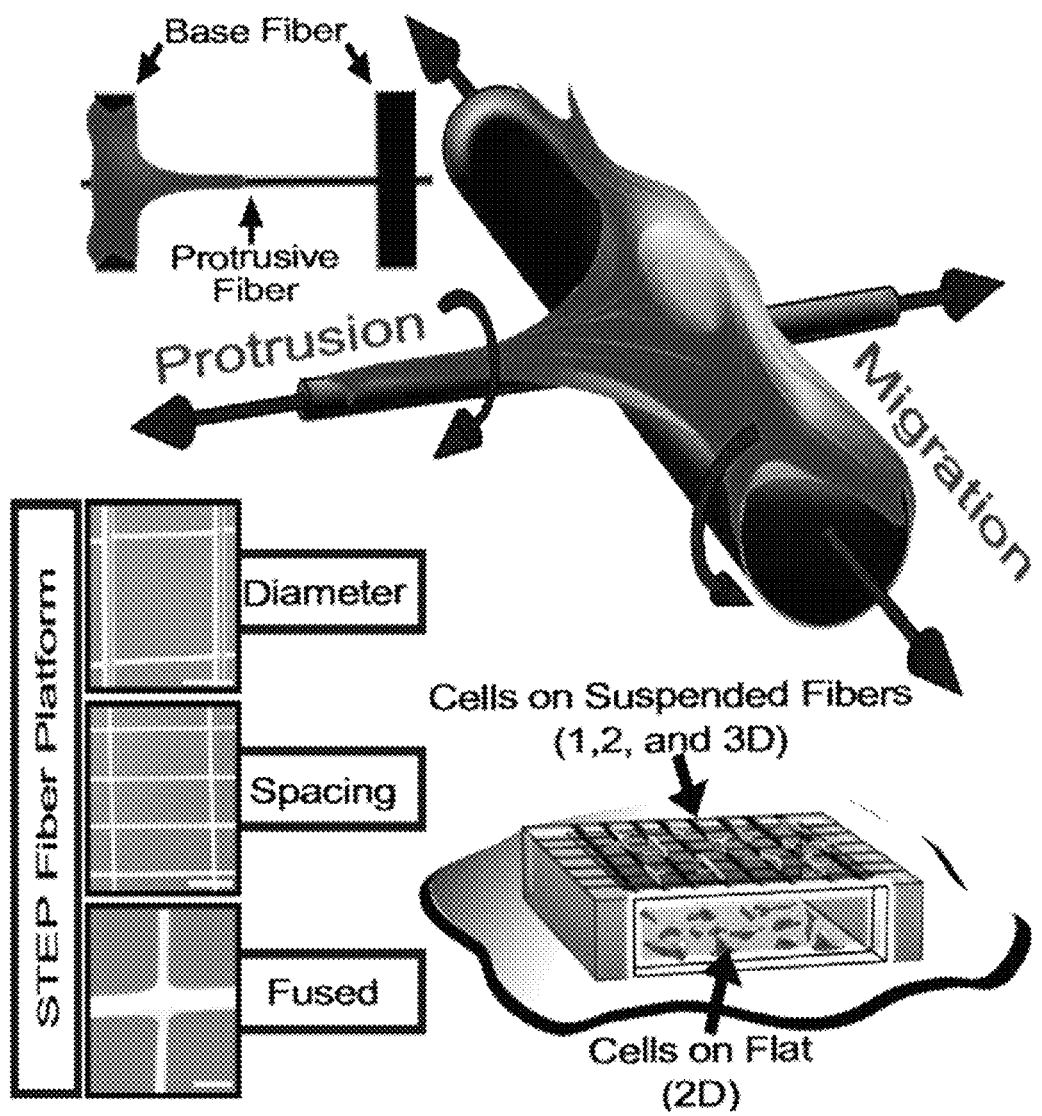
FIGS. 15A-B show a geometric design of aligned suspended nanofiber networks induce protrusions independent from migration. (A) Schematic illustration of the array of suspended fibers allowing cells to interact with three degrees of freedom: cell body alignment along support fibers (1D), protrusion formation and spreading between crossing base and protrusive fibers (2D), and cell conforming and wrapping around the fiber curvature (3D). Cells were observed to migrate exclusively along the larger support fibers while extending protrusions on the perpendicular small diameter protrusive fibers. Fibers were created using the STEP technique which allowed for high control of fiber diameter (10 µm scale bar), spacing and alignment (20 µm scale bar), and the fusion of intersections (2 µm scale bar). (B) SEM images of support fiber with crossing small, medium, and large diameter protrusive fibers (3 µm scale bar).
Figure 15B:
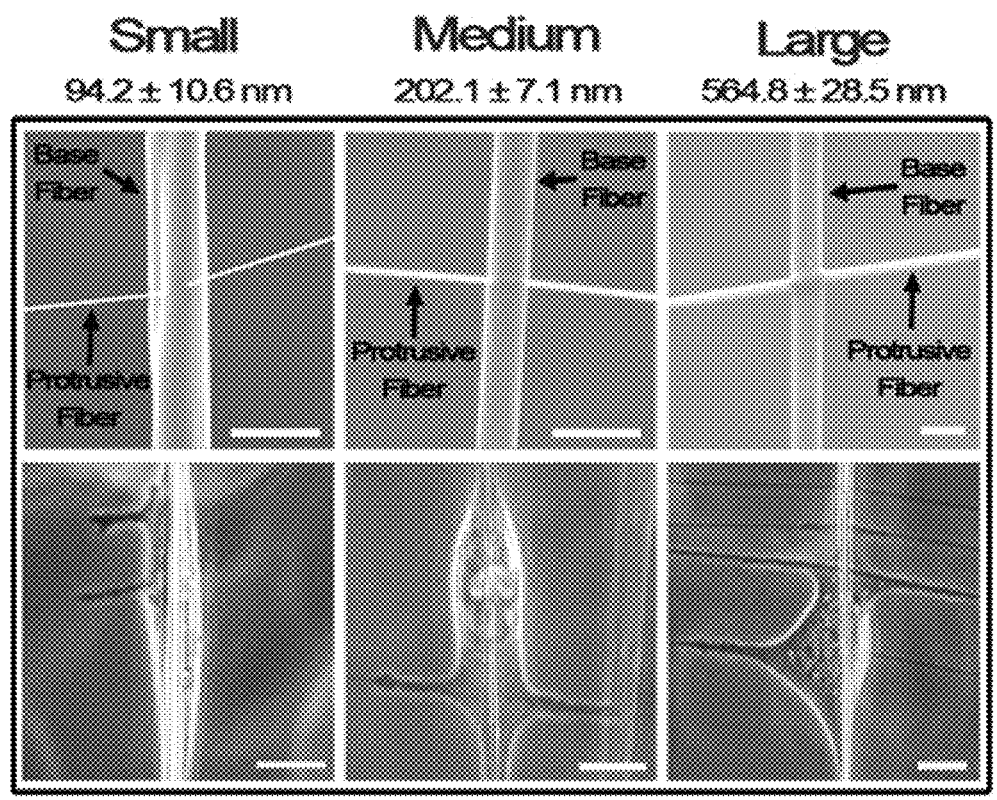

In order to successfully separate the protrusion-migration relationship, the fiber diameter was varied within the same assay to introduce geometric disparity between intersecting fibers. Specifically, by producing a network of fibers with a smaller diameter in one direction than in the other, the cells were provided with a contrast in fiber curvature and contact surface area. In such an arrangement, large diameter fibers (~2 am in diameter), denoted as 'support fibers', served as scaffolding upon which smaller diameter fibers (small: ~100 nm, medium: ~200 nm and large: ~550 nm) were deposited orthogonally and then fused (FIG. 15A). Spacing between support fibers averaged 165±29 am. The smaller 'protrusive fibers' were observed to elicit pseudopodial protrusions that exhibited varying temporal and morphological characteristics correlating with the biophysical environment. The bulk of each cell body was situated on the larger support fiber and the cells migrated along this direction exclusively. Concurrently, protrusions extended onto the smaller diameter protrusive fibers without subsequent migration onto this fiber (FIG. 15B). Protrusions were not preferentially formed on a certain side of the support fibers or at specific locations relative to the cell body and/or nucleus. The protrusions observed on this fiber network were morphologically distinct from those seen on a flat surface and were clearly distinct from the rest of the cell and its migratory path.

Figure 16:
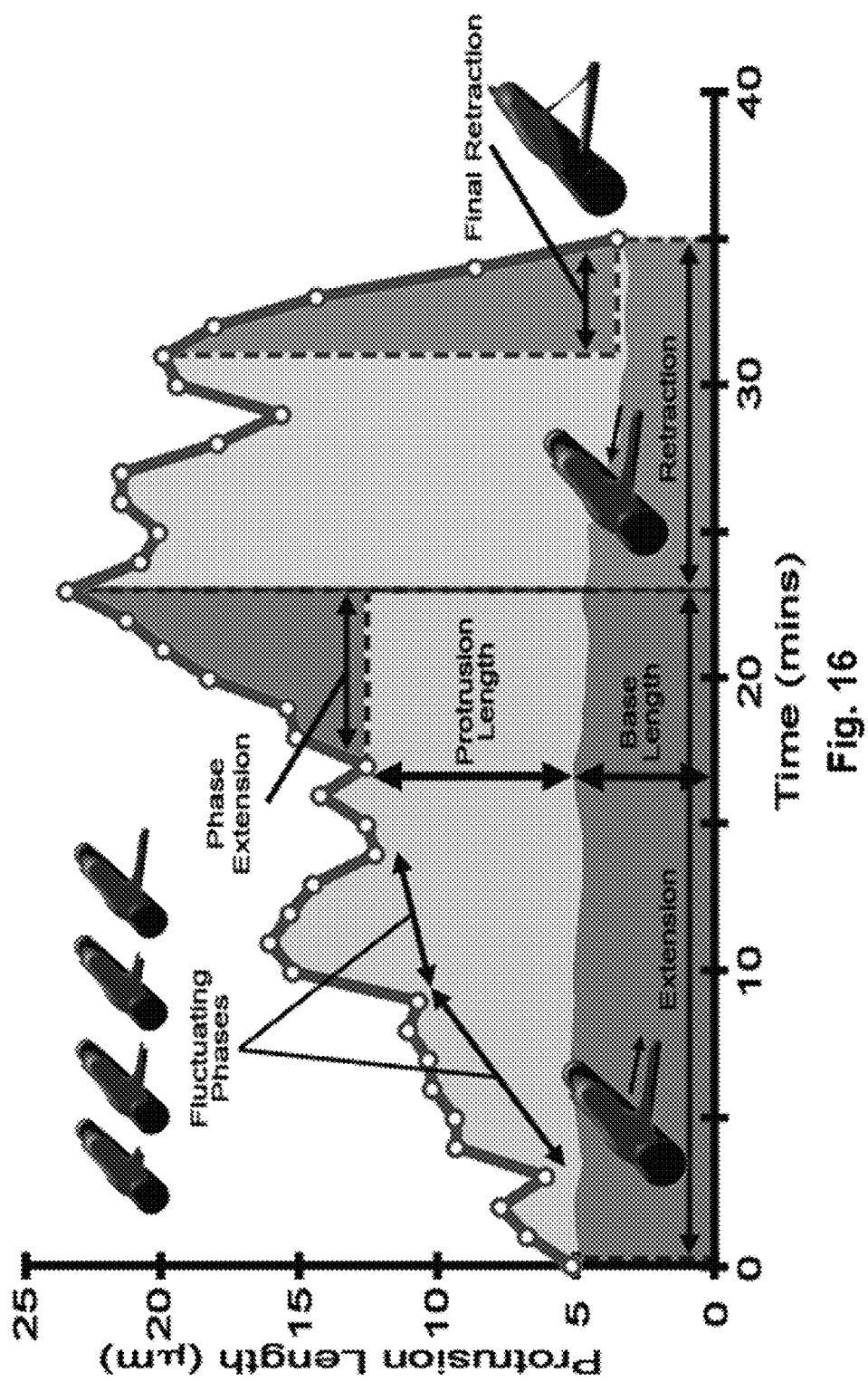
FIG. 16 shows a representative protrusion profile showing protrusion maturation over time in minutes. The profile is segmented into elongation and retraction time periods with additional metrics annotated.
Figure 17:
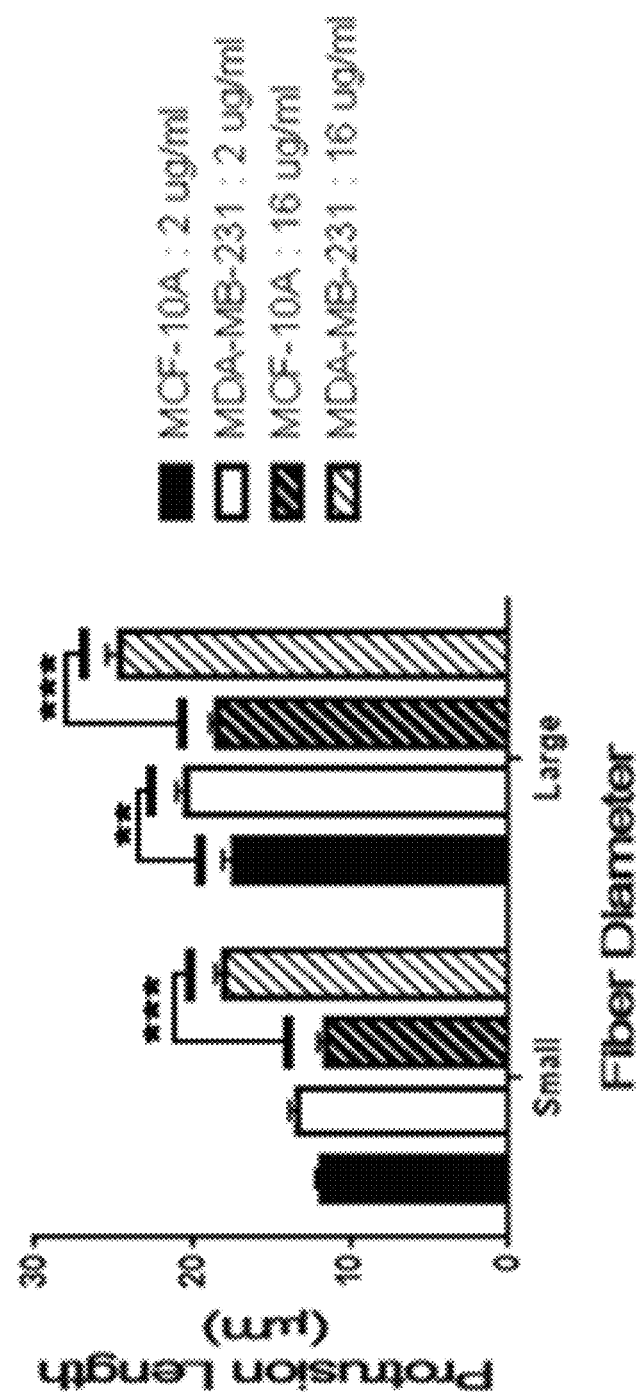
FIG. 17 shows a graph of protrusion length vs. fiber diameter of normal (MCF-10A) and cancerous (MDA-MB-231) breast cells at 2 different fiber coating concentrations of fibronectin (2 and 16 µg/ml).

When interacting with protrusive fibers of varying curvatures, cells were found to modulate their response as evidenced by the differences observed in maximum protrusion length, base length, extension rate, and retraction rate. The maximum length of the protrusion was defined to be the longest distance the protrusion extended away from the main cell body. On the other hand, the base length is defined as the distance the body of the cell moved away from the support fiber onto the protrusive fiber. For both cell types, these metrics were compared between all three protrusive fiber diameters by measuring protrusion features over time (FIG. 16). Also, in order to investigate the role of ligand density and attachment on protrusion dynamics, the protrusions were also studied on varying fiber coating concentrations of fibronectin (2, 4, and 16 µg/ml) (FIGS. 17 and 18).

Figure 18:
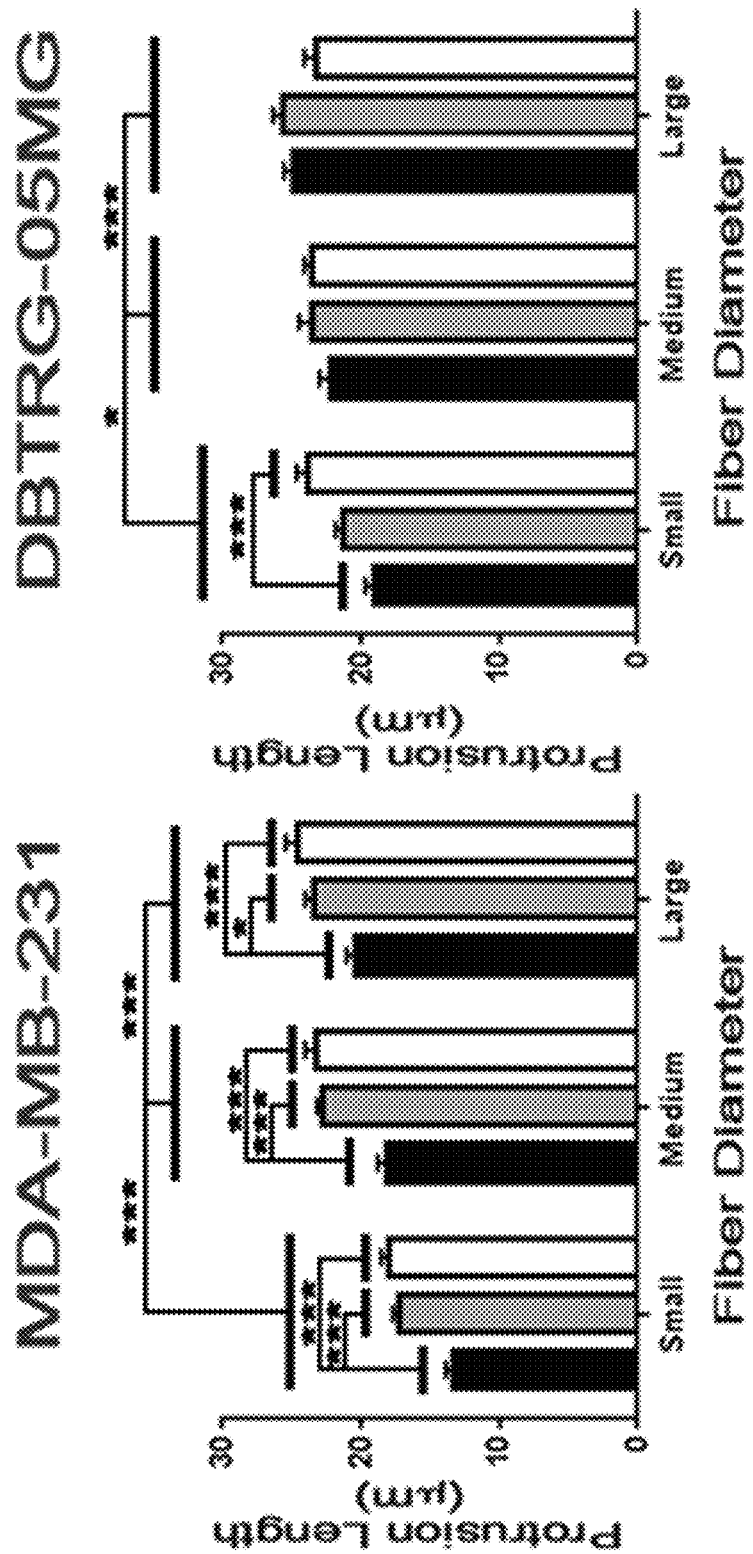
FIG. 18 shows graphs of protrusion length vs. fiber diameter of MDA-MB-231 (left) and DBTRG-05MG (right), illustrating how protrusion length is highly dependent on fiber diameter and fibronectin concentration, however, fiber properties did not show a major influence on the cell body length, extension rate, and retraction rate (n=100 per test category).

For both MDA-MB-231 and DBTRG-05MG cells, larger fiber diameters induced protrusion lengths that were significantly longer than those seen on the small diameter fibers (FIG. 18). Also, an increase of fibronectin resulted in significantly longer protrusion lengths for MDA-MB-231 for all three diameters, however, it only increased the protrusion lengths for DBTRG-05MG on the small diameter fibers. Overall, DBTRG-05MG extended longer protrusions than MDA-MB-231 on large diameter (p<0.01), medium diameter (p<0.05), and small diameter fibers (p<0.001). On average, DBTRG-05MG formed protrusions with lengths that generally ranged between 20 to 25 µm throughout. In comparison, the average protrusion lengths of MDA-MB-231 were more widespread due to a higher dependence on fiber diameter and fibronectin coating. As the concentration of fibronectin was raised from 2 to 16 µg/ml, the corresponding protrusion length averages were: 13 to 18 µm on small diameter, 18 to 23 µm on medium diameter, and 20 to 25 µm on large diameter fibers. The base lengths of the two cell types typically increased with fibronectin concentration but not with fiber diameter. Also common between these cell types, extension rates were generally seen to vary between 2 to 3 am/min while retraction rates were relatively faster and ranged from 4 to 7 am/min.

The analyses of these two types of metastatic cells reveal similar trends in protrusion dynamics with MDA-MB-231 to be more sensitive to increase in fiber curvature and fibronectin concentration compared to DBTRG-05MG. To investigate whether the protrusive dynamics observed is unique to metastatic cells, we compared the protrusions of MDA-MB-231 to those of MCF-10A, which are healthy breast epithelial cells. The comparison study (diameter: small and large, fibronectin concentration: 2 and 16 µg/ml) showed a remarkably higher protrusion length for MDA-MB-231 on both fiber diameters and fibronectin concentrations except for small diameters coated with 2 µg/ml fibronectin. Therefore, an increased protrusion length may be indicative of the metastatic capacity of a cell. However, differences in the base length, extension rate, and retraction rate were not significant, therefore, these parameters might play a smaller role in tumor progression.

This bottom-up assembly of exquisite architecture of suspended nanofibers of contrasting curvatures is capable of eliciting protrusions on high curvature while maintaining migration of single cells on low curvature fibers. Single cells of different lineages modulate their protrusion dynamics in response to mechanistic curvature cues. Highly aggressive MDA-MB-231 put longer protrusions compared to normal non-cancerous counterparts (MCF-10A) (FIG. 17) and comparison between two aggressive cell lines (breast and brain) demonstrates that breast cell lines modulate their protrusion dynamics with increasing curvature and ligand concentration, thus suggesting brain to be more aggressive. Maturation of protrusions was found to occur on lower curvature fibers with more cell body displaced outwards from the support fiber, thus showing propensity of cell to migrate along the protrusive fiber. With increasing eccentricity indicating maturation of protrusions, we demonstrate co-localization of intermediate filament vimentin and microtubules in protrusions. Depending upon the state of the cell, protrusions can be biased signifying the role of protrusions in sensing at the leading edge during migratory state and sensing the entire immediate cell environment in random manner for a stationary cell. In both states, the main protrusions emanating from cell body can branch hierarchically with individual branches demonstrating high degree of coordination. Here, for both cell types, protrusion fragments are able to be deposited away from the cell body on regions of the fiber that the cell has not migrated on. Therefore, cell fragments may be placed wherever cells are able to protrude instead of only where they are capable of migrating. The specific properties of a fiber micro-nanoenvironment, in this case the fiber curvature, can either promote or inhibit the development of protrusions.

Example 6

Figure 19A:
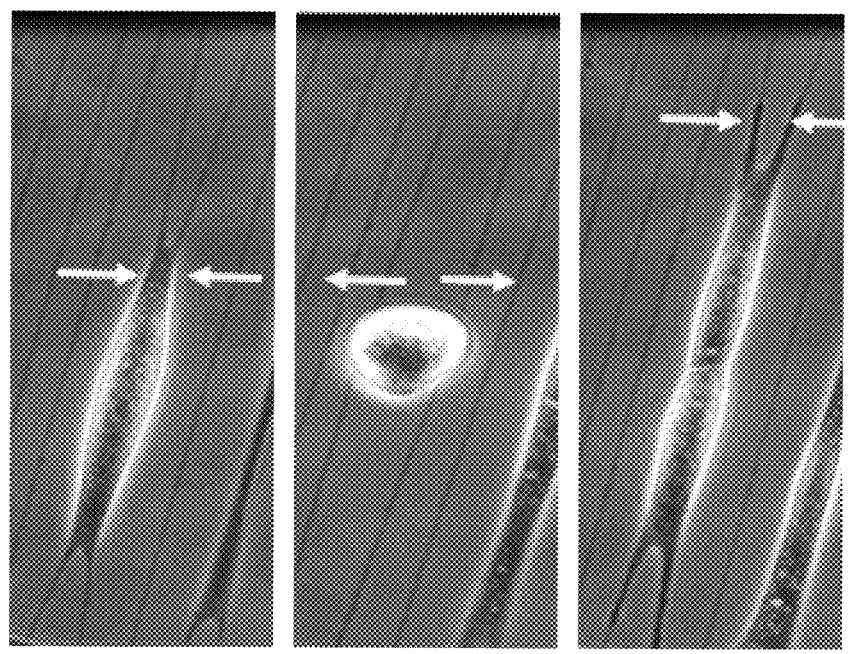
FIGS. 19A-B show an optical image (A) and graph of contracting and expanding forces in function of time (B) corresponding to a cell division on a nanonet.
Figure 19B:
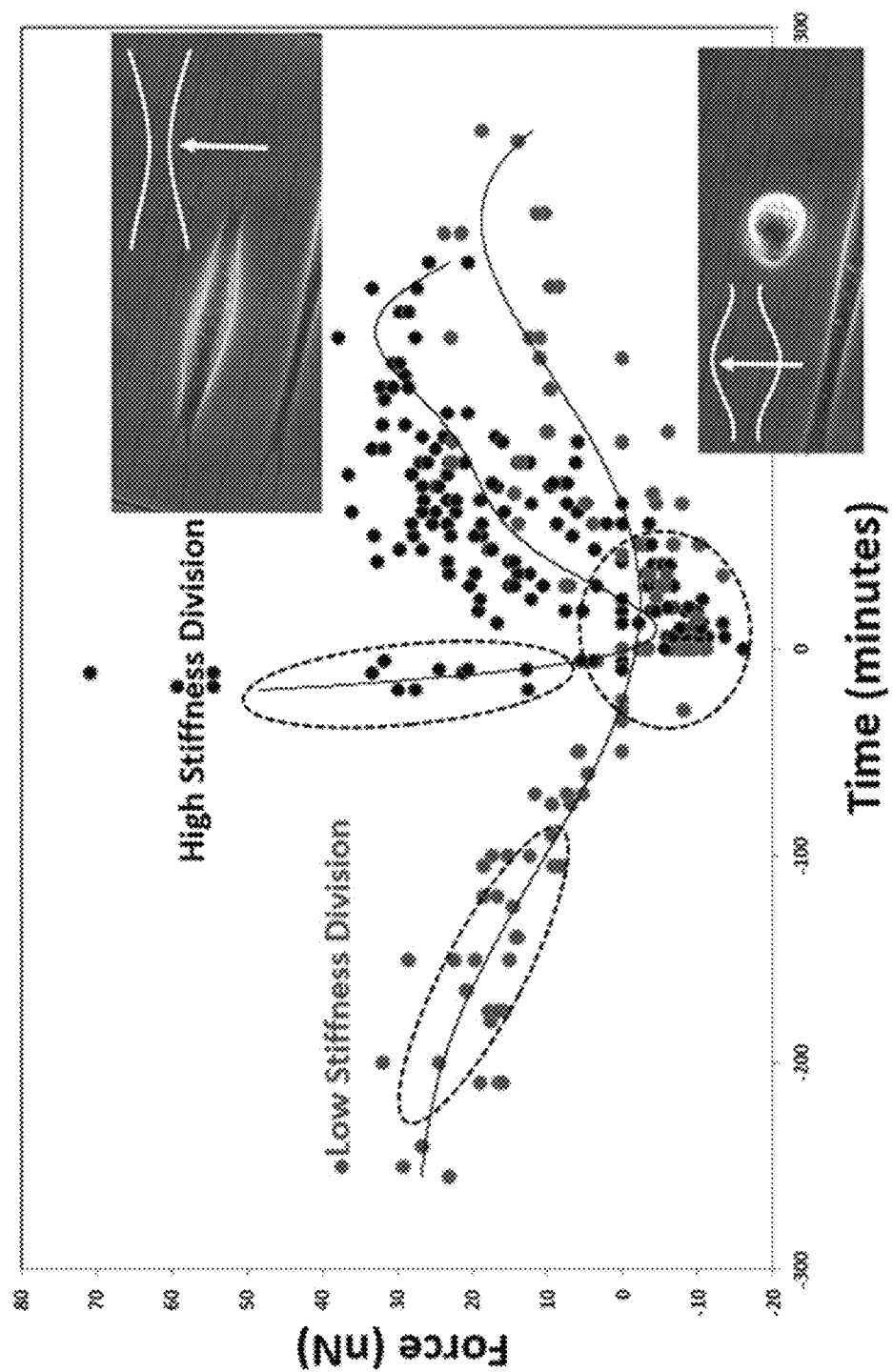
Figure 20A:
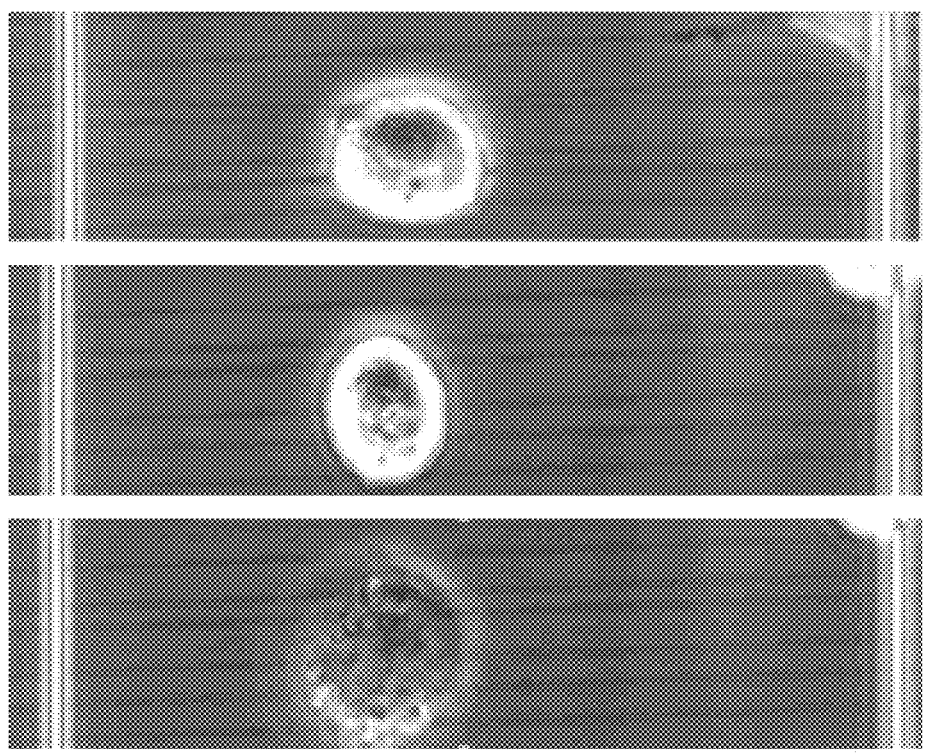
FIGS. 20A-B show an optical image (A) and graph of contracting and expanding forces in function of time (B) corresponding to a cell apoptosis on a nanonet.
Figure 20B:
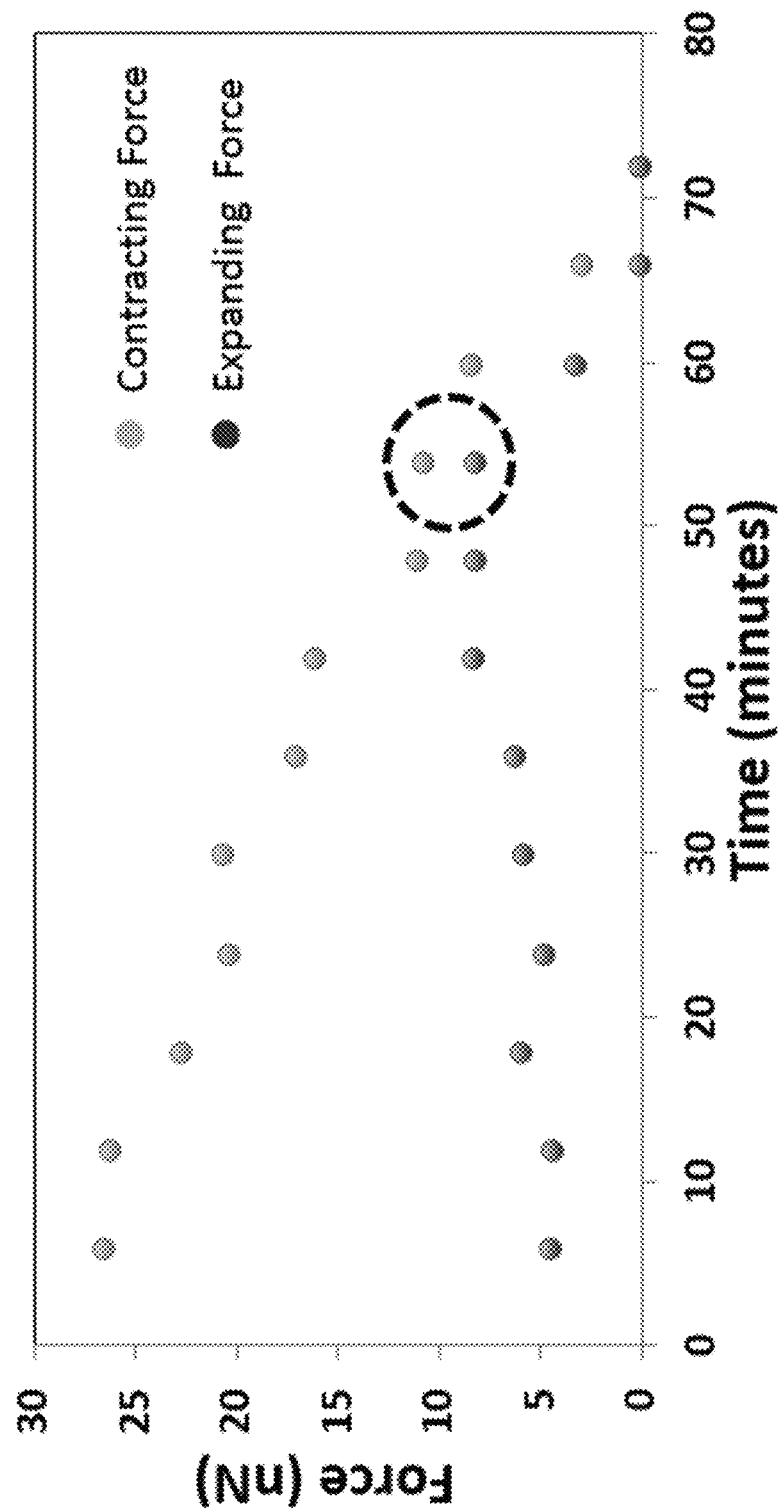

Inside-Out (IO) Fiber Deflections Measurement of Division, Apoptosis, Leader Cell, Cell Aspiration, and Debris Forces FIGS. 19A-B show that cell division can be measured using the nanonet platform technology described herein, for example, by measuring the contracting and expanding forces in the fibers. Similarly, FIGS. 20A-B show that cell apoptosis can be measured using the nanonet platform technology described herein, for example, by measuring the contracting and expanding forces in the fibers. Using high vacuum grease (Dow Corning, Midland, Mich.), the fiber scaffolds were mounted on glass bottom six-well plates (MatTek Corp., Ashland, Mass.) and sterilized with 70% ethanol and ultraviolet rays in a sterile hood for 20 min. The ethanol was aspirated, the substrates were rinsed with phosphate buffered saline ((PBS), Fisher Scientific, Pittsburgh, Pa.) twice, and the fibers were coated with fibronectin from bovine plasma (8 µgml$^{-1}$, Sigma-Aldrich, St. Louis, Mo.) for at least an hour at 37° C. before seeding the cells. Mesenchymal Stem cells (American Type Culture Collection, Manassas, Va.) were cultured in Dulbecco's Modified Eagle Medium (DMEM) supplemented with 10% fetal bovine serum (FBS) and 1% penicillin/streptomycin (HyClone Laboratories, Logan, Utah). Cells were seeded onto the fiber scaffolds via 30 ml droplets at a concentration of 100,000 cells ml$^{-1}$ and incubated at 37° C. and 5% $CO_2$. Cells were then given 2-6 h to attach onto the nanofibers. After 1 hour of seeding, 2 ml of medium was added to each well. For cell division, cells that were observed to be balling up were imaged continuously using optical microscope with incubation capabilities. For apoptosis experiments, cells were starved of $CO_2$, and imaged continuously using optical microscope with incubation capabilities.

Figure 21A:
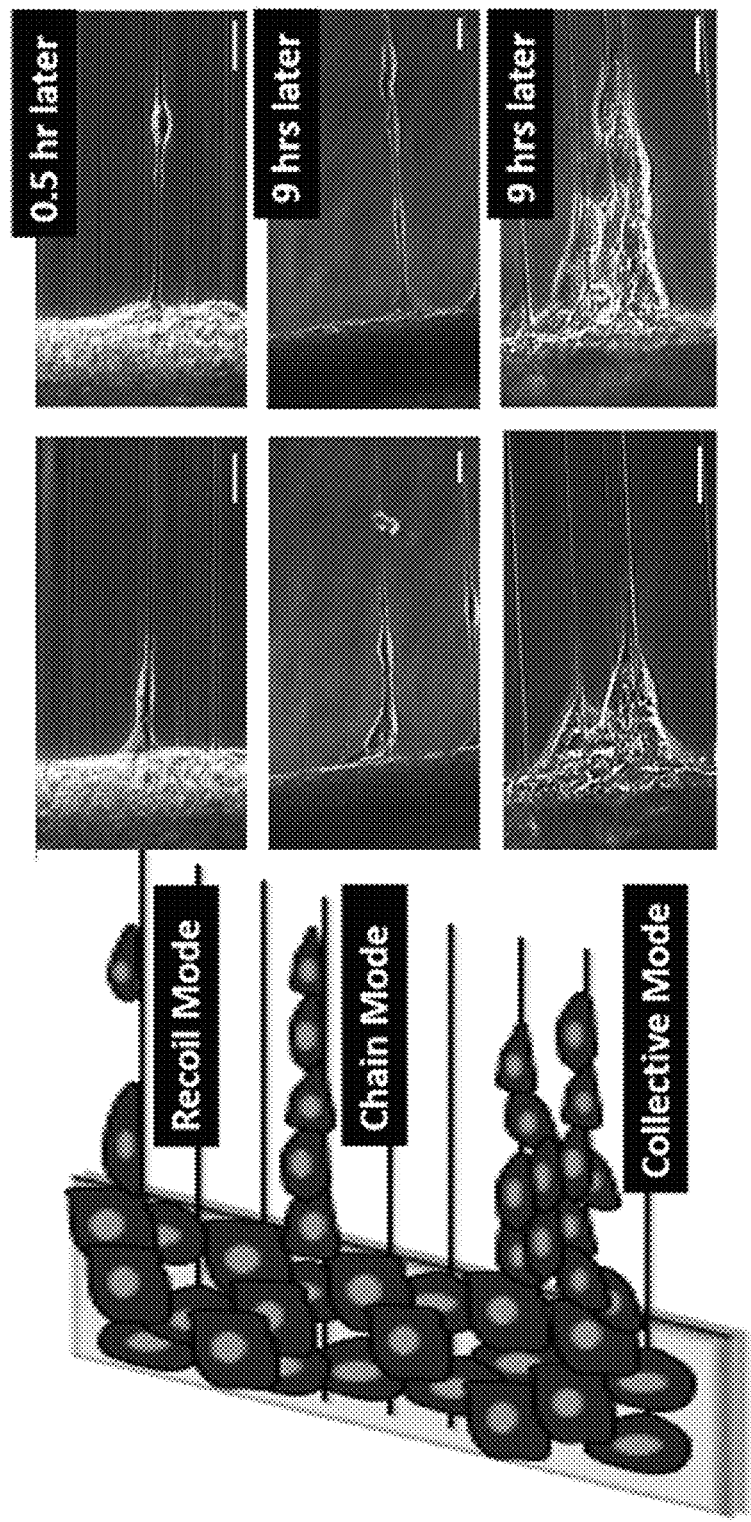
FIGS. 21A-C show a schematic illustration and optical images of NIH3T3 fibroblast cells that are staged on nanonets having the same fiber diameters but having varying fiber spacings.
Figure 21B:
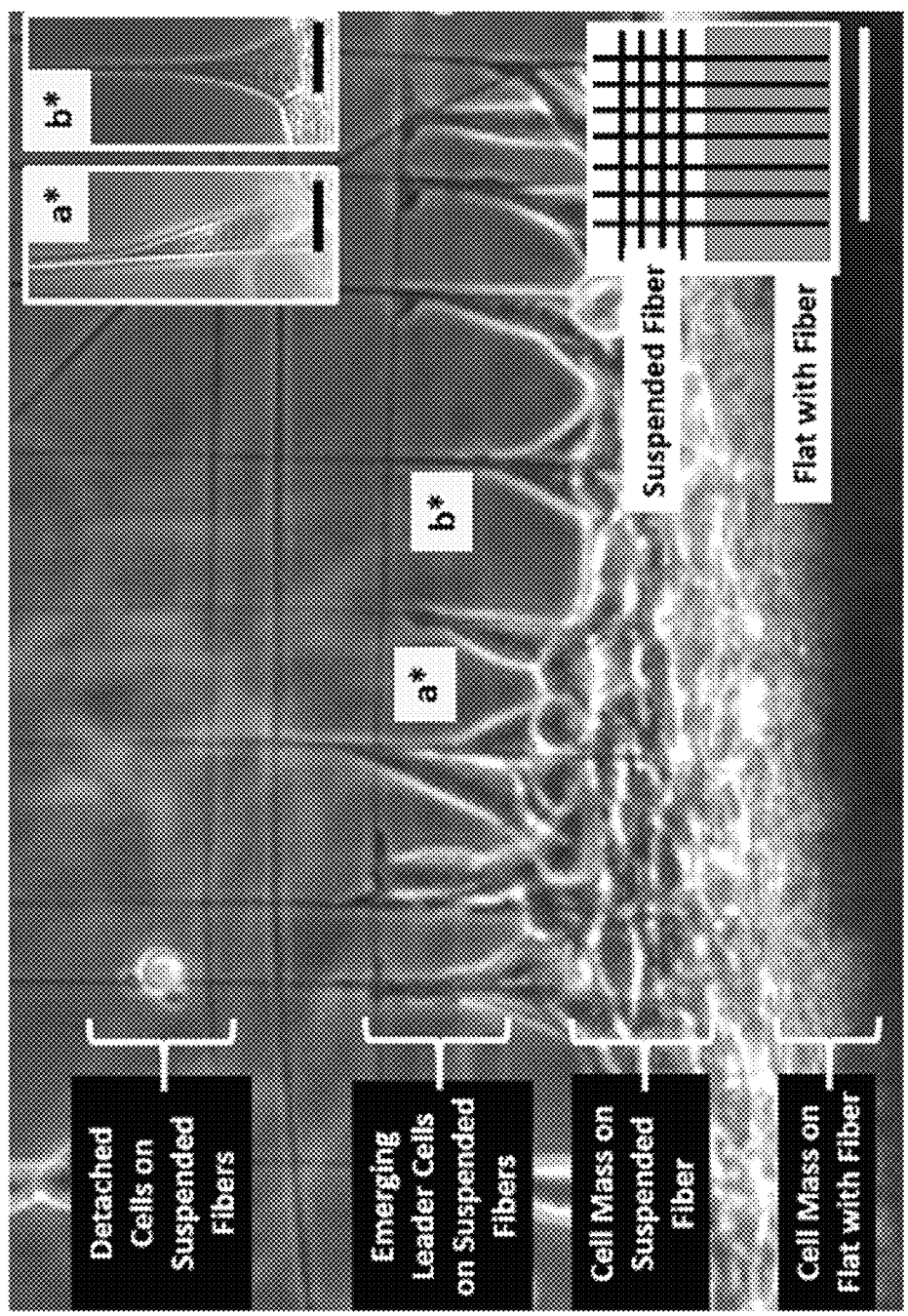
Figure 21C:
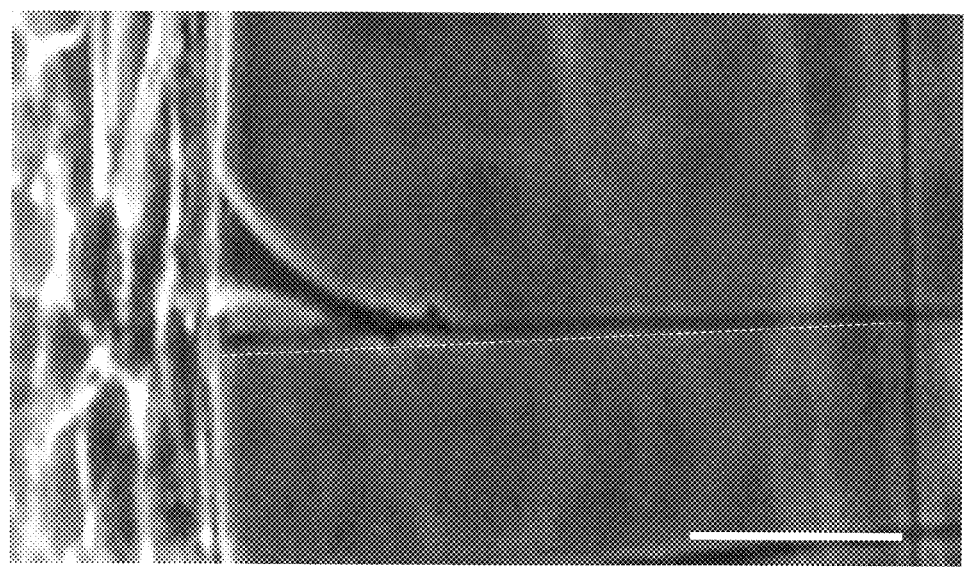

FIGS. 21A-C show NIH3T3 fibroblast cells that are staged on nanonets having the same fiber diameters but having varying fiber spacings. The cancer cells are placed on a rigid structure in contact with the nanonet having varying fiber spacings and are observed to metastasize at different degrees over time. Deflection forces can be measured when leader cells are starting to migrate on the nanonet. As recommended by the American Type Cell Culture (ATCC), these cells were grown in T25 cell culture flasks (Corning Inc., Corning, N.Y.) with Dulbecco's Modified Eagle's Medium (DMEM, HyClone, Logan, Utah) and 10% bovine calf serum (ATCC, Manassas, Va.). The cell culture was maintained at 37° C. and 5% $CO_2$. Before seeding the cells onto the STEP fibers, the cells were suspended in cell media as follows. Media from a T25 flask containing adherent NIH3T3s was aspirated and the adherent cells were rinsed with phosphate buffered saline (PBS, Fischer Scientific, Pittsburgh, Pa.) twice. They were then incubated with 500 µl 0.25% Trypsin (HyClone, Logan, Utah) for five minutes at 37° C. and suspended in fresh cell culture media. Concentrated cell suspension was seeded on two sterile platforms adjacent to the suspended fibers as shown. The cells were allowed to attach overnight at 37° C. and 5% $CO_2$. After cell attachment, 2 ml of cell culture media with 1% penicillin/streptomycin (HyClone, Logan, Utah) was added to the well to facilitate further cell growth. The cell culture media was changed 3 times a week after rinsing the substrates with PBS.

Figure 22A:
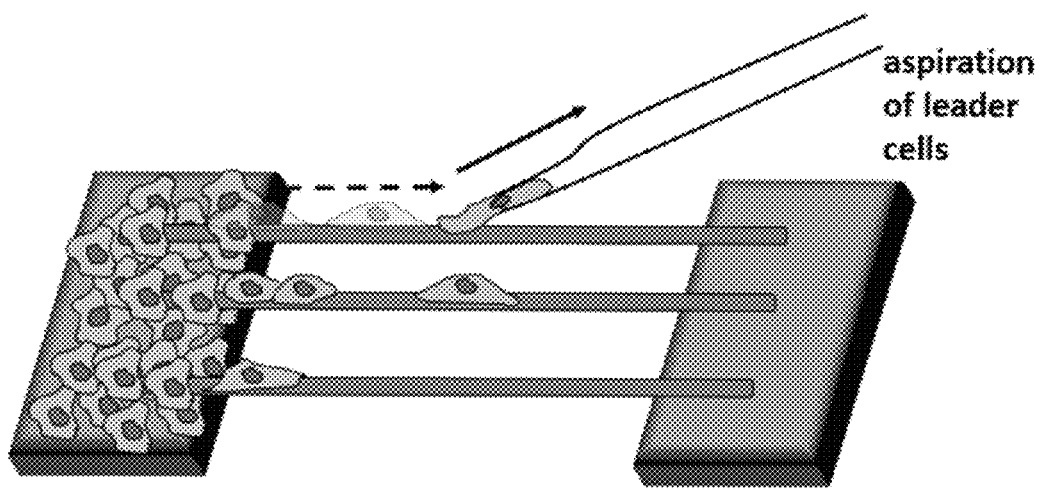
FIGS. 22A-B show schematic illustrations and optical images the cell aspiration via use of sticky probe to pull leader cells such as those of FIGS. 18A-C and 21A-C.
Figure 22B:
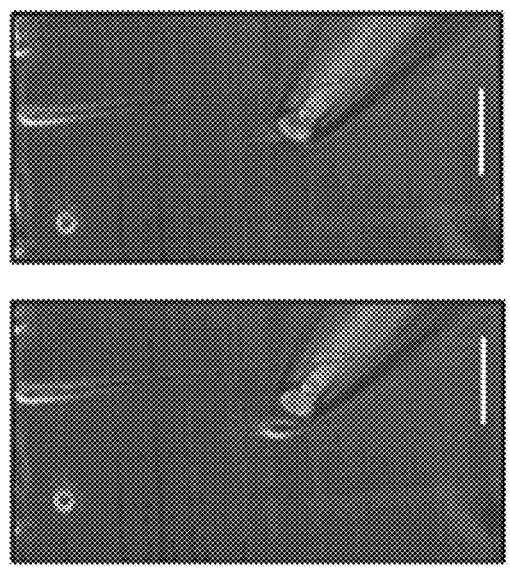
Figure 22B:
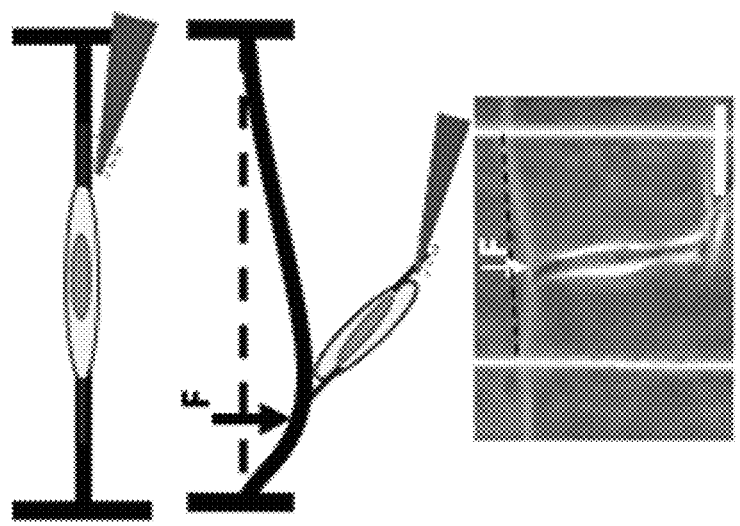

FIGS. 22A-B show the cell aspiration forces via use of sticky probe to pull these leader cells. The forces of attachment can be measured. Various cell adhesion coating compounds may provide different results. A micropipette coated with adhesion protein and computer controlled was brought in contact with the cell attached to fiber and left in contact for variable time. The probe was then retracted, resulting in cell body detaching from the fiber. The measured deflection of the fiber was used to calculate the force of adhesion. Force of adhesion can also be measured by applying perturbation to fibers using an automated probe, till cells detach from one of the fibers.

Figure 23A:
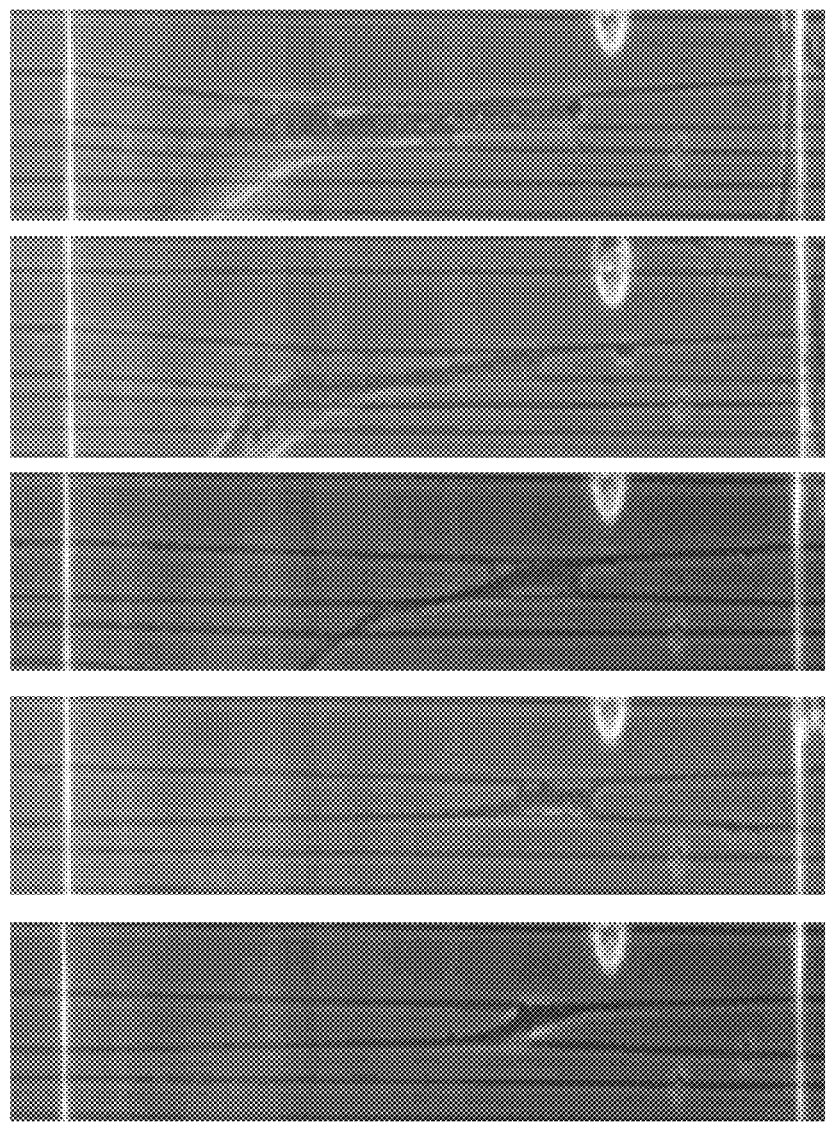
FIGS. 23A-B show optical images (A) of a cell shedding debris and corresponding graph representing the force vs. time characteristic of these debris (B).
Figure 23B:
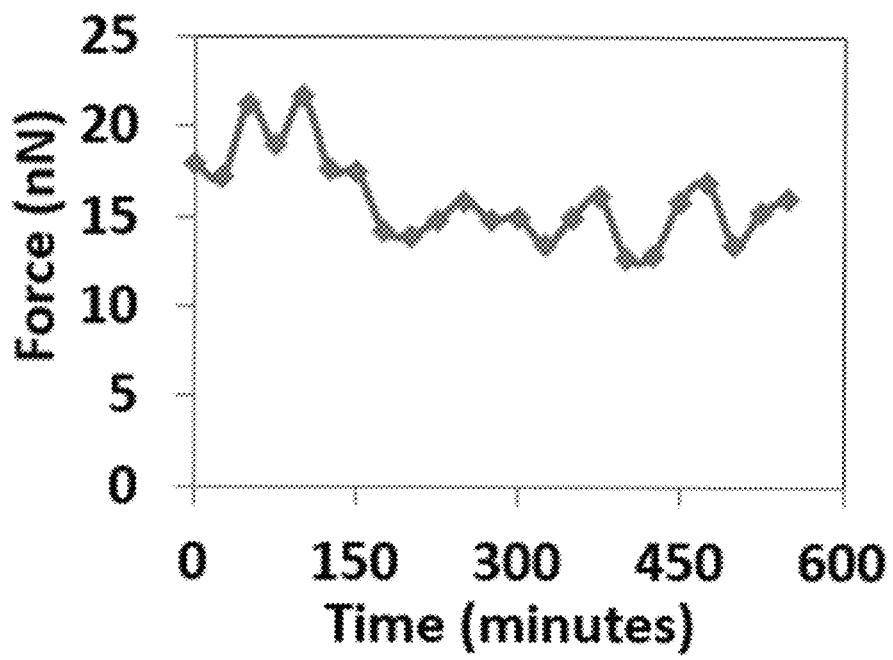

FIGS. 23A-B show a cell shedding off debris and corresponding graph representing the force vs. time characteristic of these debris. Using high vacuum grease (Dow Corning, Midland, Mich.), the fiber scaffolds were mounted on glass bottom six-well plates (MatTek Corp., Ashland, Mass.) and sterilized with 70% ethanol and ultraviolet rays in a sterile hood for 20 min. The ethanol was aspirated, the substrates were rinsed with phosphate buffered saline ((PBS), Fisher Scientific, Pittsburgh, Pa.) twice, and the fibers were coated with fibronectin from bovine plasma (8 μgml$^{-1}$, Sigma-Aldrich, St. Louis, Mo.) for at least an hour at 37° C. before seeding the cells. Mesenchymal Stem cells (American Type Culture Collection, Manassas, Va.) were cultured in Dulbecco's Modified Eagle Medium (DMEM) supplemented with 10% fetal bovine serum (FBS) and 1% penicillin/streptomycin (HyClone Laboratories, Logan, Utah). Cells were seeded onto the fiber scaffolds via 30 ml droplets at a concentration of 100,000 cells ml-1 and incubated at 37° C. and 5% $CO_2$. Cells were then given 2-6 h to attach onto the nanofibers. After 1 hour of seeding, 2 ml of medium was added to each well. Cells that were observed to shed debris were imaged continuously using microscope with incubation capabilities.

Example 7

Outside-In (OI) Perturbation Measures Cell Adhesion Strength

Materials and Methods
Probe Design and Operation

Micropipette probes were pulled to 1 μm diameter tips from 1.0 mm diameter capillary glass rods (Sutter, Novato, Calif.) using the P-1000 Flaming/Brown micropipette puller (Sutter). Using an MP-285 motorized manipulator (Sutter) probes were positioned near parallel-shaped cells and then pre-programmed for strain rate, end-state position, and number of cycles. A strain rate of 3 μm/s was used unless otherwise noted since it was the slowest rate at which cells did not exhibit viscoelastic effects.
Results To measure OI cell adhesion forces, a probe system was designed to perturb single parallel-shaped cells via programmable micromanipulated motions. Two different modes of operation were designed to determine the effect of biased loading on cell adhesion: symmetric dual probes (OI-Dual) positioned on either side of a parallel-shaped cell, actuating the cell symmetrically (FIG. 9C (i)), and a single probe (OI-Single) actuating one side of the cell to induce bias (asymmetric mode) (FIG. 9D (i)). For the dual probe system, two probe tips were placed on either side of a cell in contrast to the single probe (biased) mode. To determine cell adhesion strength, the cell was stretched to failure (detachment from fiber) by pushing the leading active fiber while recording the deflection of trailing passive fiber. The cytoskeletal network experiences increasing force in this configuration as the cell is stretched, and eventually the cell detaches with the passive fiber returning to its original non-deflected state. The maximum force value reached during this test was taken to be the adhesion force of the cell.

OI-Dual manipulation (FIG. 9C (ii)) results in comparatively even force distribution within the cell, with averages of $P_a$=33.4±3.8 nN and $P_b$=29.1±2.5 nN on 250 nm fibers, $P_a$=62.0±5.6 nN and $P_b$=45.8±4.0 nN on 400 nm fibers, and $P_a$=131.5±8.3 nN and $P_b$=111.0±6.6 nN on 800 nm fibers. These forces correspond to fiber deflections averaging 3.2% of their span length, falling within the suggested elastic limit for polystyrene nanofibers [Carlisle, C. R., et al., Acta Biomater. 2010; 6:2997-3003; Gestos, A., et al., Polym. Test. 2013; 32:655-64]. The force-time plot from a dual probe perturbation typically shows a steady rise in force as the cell is stretched while maintaining adhesion integrity followed by a sharp drop as the cell-fiber adhesion fails, representative of the abrupt breaking failure typically observed (FIG. 9C(iii)). The failure locations averaged over all diameters demonstrated cell-fiber failure to occur equally on each side of the cell (a: 29%, b: 29%, both simultaneously: 42% of the time), further suggesting even distribution of forces within the cell.

OI-Single manipulation results in averages of $P_a$=31.4±4.1 nN and $P_b$=27.6±1.7 nN on 250 nm fibers, $P_a$=66.3±5.7 nN and $P_b$=43.3±5.2 nN on 400 nm fibers, and $P_a$=103.5±9.8 nN and $P_b$=115.4±9.9 nN on 800 nm fibers (FIG. 9D (ii)). Biasing the perturbation by using only a single probe results in failure initiation shifting towards b (a: 17%, b: 58%, both simultaneously: 25% of the time). Force-time plots from OI-single tests also steadily rise over time, but instead of dropping sharply as seen in cells perturbed with dual probes, a peeling-type failure mechanism is observed wherein forces are observed to level off before failing (FIG. 9D (iii)). The ability to control single cell force distribution and detachment location may prove valuable in understanding certain cell events, such as leader cell formation in metastasis from primary tumors or single cell injury models. The force of adhesion averaged over all diameters remained similar (dual actuation:126.6±8.7 nN and single actuation: 121.0±8.6 nN), which compare favorably to forces obtained through other OI approaches [Simon, A., et al., Micron 2006; 37:1-13; Ferrell, N., et al., Sensors Actuators A Phys. 2011; 170: 84-89].
Effects of Nanofiber Curvature Attempting to determine if fiber curvature could explain diameter-dependent bias effects, having previously observed cells on smaller diameter fibers to cluster adhesions over a longer distance (presumably due to the reduced available adhesion area per unit fiber length) [Meehan, S., et al., Biophys. J 2014; 107(11):2604-11; Sheets, K., et al., Acta Biomater. 2013; 9(7):7169-77; Gautrot, J. E., et al., Nano Lett. 2014; 14 (7):3945-52], it was hypothesized that curvature-induced adhesion orientation was at least partially responsible for diameter-dependent bias effects. Furthermore, as evidenced by the breaking vs. peeling-type of failure observed, bias may be perturbing focal adhesions differently on fibers of different diameters due to spatial orientation, polarization, and/or structural stiffness effects.

Figure 24A:
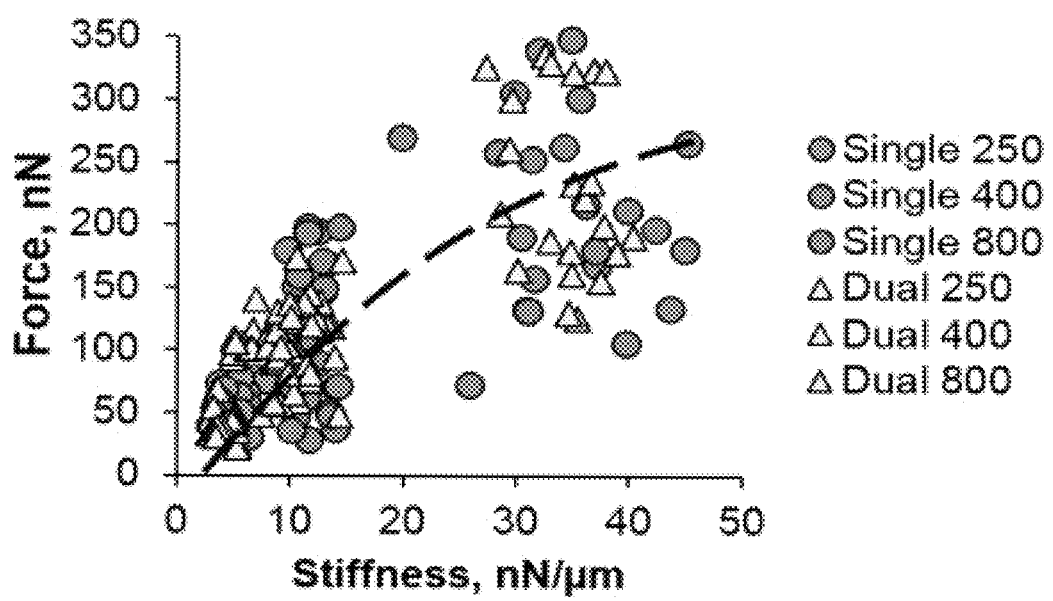
FIGS. 24A-D (A) OI Force as a function of structural stiffness, (B) OI Force as a function of cell spread area, (C) Failure occurrence at locations 'A', 'B' and 'Each' for OI-Dual and OI-Single modes, and (D) Probe angle as a function of diameter and actuation type shows (i) single probe bias creates an average probe angle of 11.5° compared to (ii) dual probe bias of 5.3° (Scale bar 25 µm) (n=188).
Figure 24B:
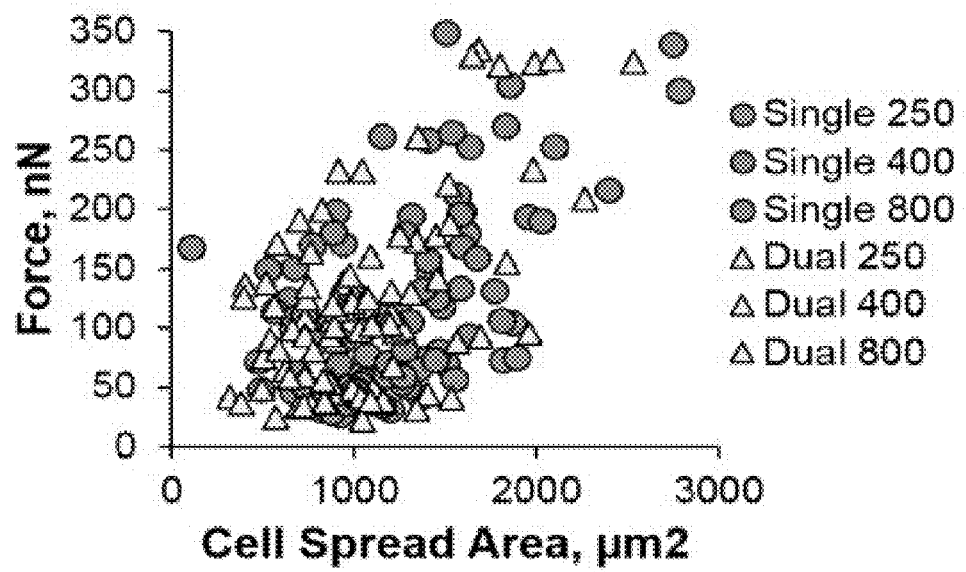
Figure 24C:
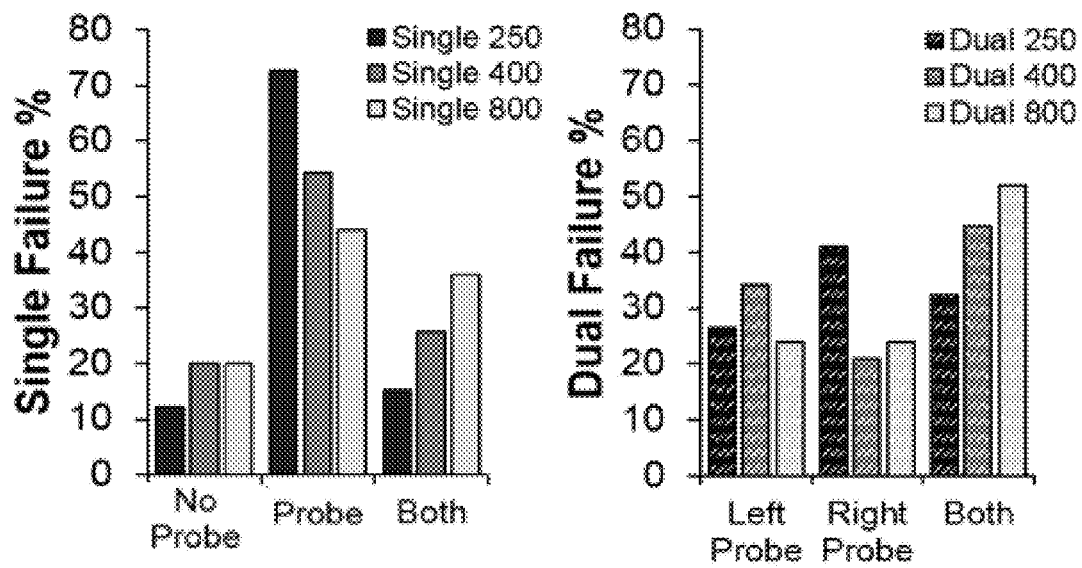
Figure 24D:
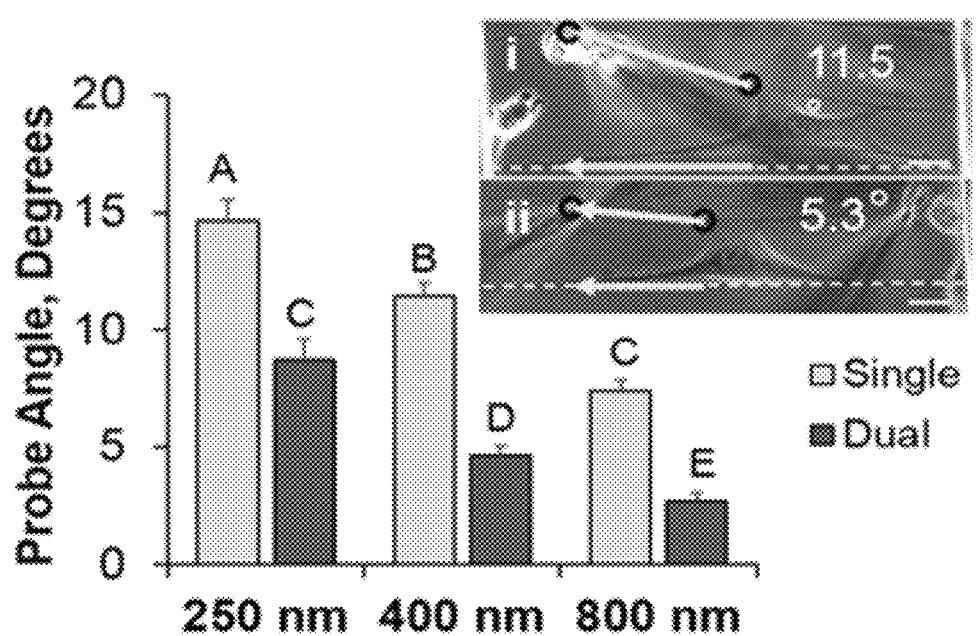

It was found that increasing fiber structural stiffness 'k' values were associated with increased adhesion forces, where a linear trend was seen for lower stiffnesses that saturated after approximately 35 nN/μm (FIG. 24A). Cell spread area was also measured at the time of failure and found to be only weakly correlated with total force, in good agreement with findings from literature (FIG. 24B). Single mode actuation introduced bias, which appeared to affect forces differently on different diameter fibers. Although not statistically significant, bias slightly decreased forces on small fibers (250 nm), did not affect forces on medium fibers (400 nm), and slightly decreased forces on large fibers (800 nm) (Supporting Material). However, the average detachment forces for all diameters ($F_{average\ Dual}/F_{average\ Single}$) remained close to unity (250 nm: 1.06, 400 nm: 0.98 and 800 nm: 1.12), thus suggesting that probe based bias ultimately dictates location of the initiation of failure (FIG. 24C). Probe perturbation also created an angle between the leading active and trailing passive fiber. To quantify this angle, a line was drawn between the probe and cell-fiber interface on the actuated fiber (arrow connecting circles) and compared to the original position of the trailing fiber serving as reference (arrow overlaying white dashed lines) (FIG. 24D(i,ii)). Averaged over all diameters tested, OI-dual manipulation resulted in an angle of 5.3°, whereas the single probe created an angle of 11.5° between the actuated and passive fibers prior to cell failure (FIG. 24D). These angles were largest for the 250 nm diameter fibers and smallest for the 800 nm fibers, thereby further suggesting FAC organization at the poles.

To investigate the role of bias further, nanonets having different diameters (400 and 800 nm), to which cells could attach to simultaneously, were made. Both the OI-Dual and OI-Single modes were used to determine if diameter-dependent bias effects observed previously on constant diameter fibers would be conserved when the cell attached to mismatched diameters.

Figure 25:
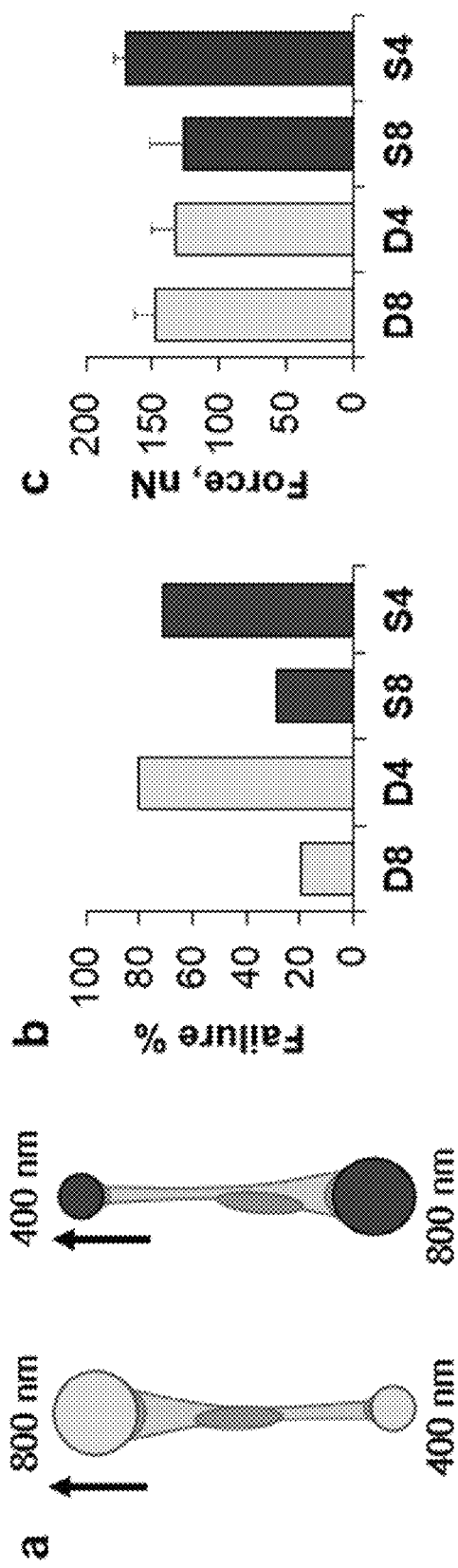
FIG. 25 shows (a) a sketch of mismatch diameter orientations, as well as data showing (b) failure occurrence, and (c) forces at failure for each case (D8=dual 800 nm; D4=dual 400 nm; S8=single 800 nm; S4=single 400 nm) (n=51).

In both the OI-Dual (light shading) and OI-Single (dark shading) modes, cells failed more often on the smaller diameter fiber (D4 and S4) compared to the large diameter fiber (D8 and S8) (FIG. 25b), while forces of adhesion were found to remain similar for each location of failure (FIG. 25c), thus, further supporting our findings on the role of fiber curvature on focal adhesion clustering and its implications in cell's ability to modulate force response to external perturbation.

Platform Applications:
Cell-Cell Junction Behavior on Nanonets

Figure 26A:
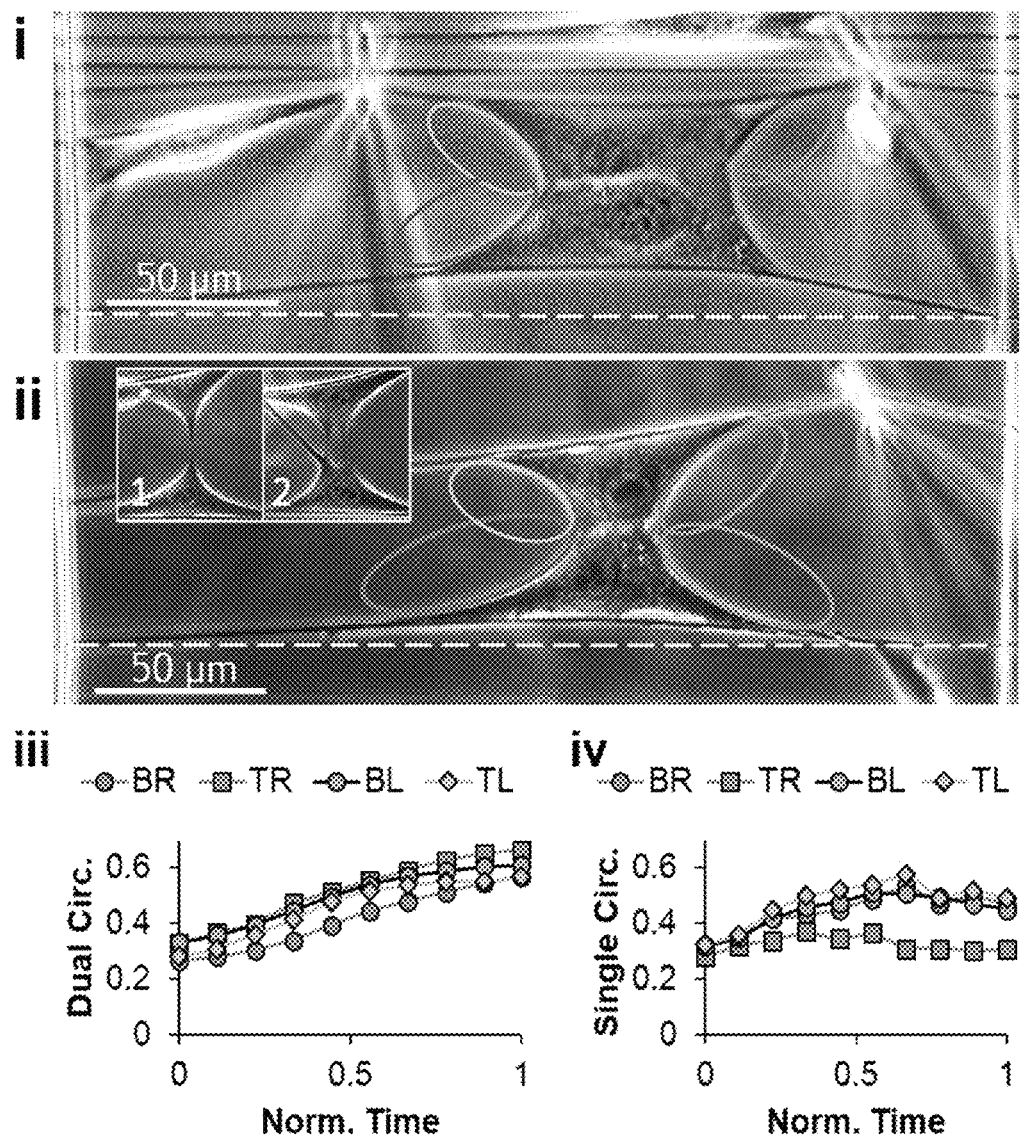
FIG. 26A-B shows cell-cell junction tests are performed with (i) the dual probe and (ii) the single probe and show the effect of bias via circularity measurements, wherein (iii) dual probe causes steady increase in circularity on all four edges of the cell (top left (TL), top right (TR), bottom left (BL), bottom right (BR)), while (iv) single probe causes circularity reduction at the edge closest to the probe (n=37), Forces (v) are higher when failing on fibers (F) compared to cell-cell junctions (J) for both systems (n=52), (vi) Spacing of the filaments spanning the cell-cell junction (inset 1 and 2 of (ii)) correlates with number of filaments seen (n=11), and (vii) Forces decrease when the junction width decreases more rapidly (n=23).

In their native environment, cell-cell junctions allow cells to adhere to one another to maintain proper tissue functionality. Cell-ECM contacts occur through integrins while cell-cell junctions are anchored by cadherins [Leerberg, J. M., et al., Protoplasma 2013; 250:817-29]. Physical cues which drive cell-ECM adhesion growth are typically reported to be similar for cell-cell contacts; for instance, enhanced contractility due to increased substrate stiffness causes stronger cell-cell adhesion [Liu, Z., et al., Proc. Natl. Acad. Sci. U.S.A 2010; 107:9944-9; Cavey, M., et al., Cold Spring Harb. Perspect. Biol. 2009; 1:a002998]. In the case of muscle tissue, cell-cell junctions allow faster passage of calcium waves which are used to coordinate contraction, and are precursors to cell-cell fusion and differentiation into myotubes [Chun, J. T., et al., Intracellular Calcium Waves, 2nd ed., Elsevier Inc., 2013; Ku, S. H., et al., Biomaterials 2012; 33:6098-104]. In contrast to other systems exploring cell-cell adhesion on micropillars or using an AFM cantilever [Liu, Z., et al., Proc. Natl. Acad. Sci. U.S.A 2010; 107:9944-9; Shen, Y., et al., Biochem. Biophys. Res. Commun. 2011; 409:160-5], the nanonet probe system allows simultaneous investigation of cell-cell junctions and cell-ECM contacts (FIG. 26).

Cell-cell pairs formed spread morphologies similar to those of single cells except with a fusion plane running parallel to the fiber axis. When actuated with the OI-Dual system, cells were pulled evenly on both sides. This was confirmed by circularity analysis of the curvatures between the cell-cell junction and the cell-fiber adhesions located at the top left (TL), top right (TR), bottom left (BL), and bottom right (BR) of the cell-cell pair (FIG. 26A (i)). Cell configuration was initially slightly elongated (low circularity) but became more circular throughout the stretch, and did so evenly on each side (FIG. 26A (iii)). On the other hand, OI-Single actuation (FIG. 26A (ii)) induced uneven cell stretching as evidenced by saturation and eventual decrease in the top right circularity (closest to the probe) (FIG. 26A (iv)).

Figure 26B:
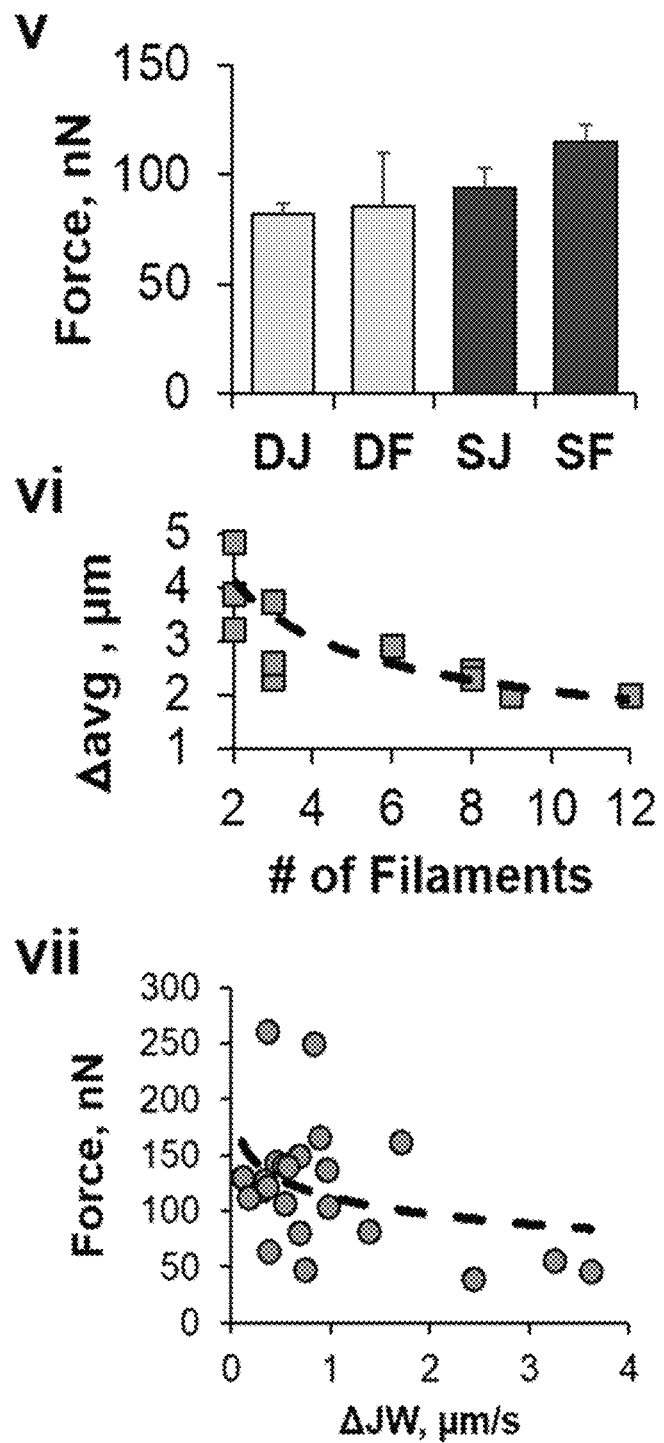

While failure occurred more often at the cell-cell junction for both actuation modes (65% of the time for single and 90% of the time for dual) in agreement with other recent studies, bias again did not significantly affect total force at detachment (FIG. 26B (v)). During failure, long filamentous structures were seen spanning the gap of the junction as it failed (FIG. 26A (ii), inserts 1 and 2). Several groups have shown the formation of these structures, which are composed primarily of actin surrounded by the plasma membrane, during junction formation but have not described its behavior during junction failure [Cavey, M., et al., Cold Spring Harb. Perspect. Biol. 2009; 1:a002998; Hoelzle, M. K., et al., Mol. Biol. Cell 2012; 23:310-23; Brevier, J., et al., Phys. Biol. 2008; 5:016005]. It was noted that as the number of filaments spanning the gap between the two cells increased, the average distance between each filament decreased (FIG. 26B (vi)). A single filament could often be seen holding the entire cell-cell junction together before failure. We speculate that this behavior may arise from the distribution and clustering of cadherin throughout the junction [Chu, Y.-S., et al., J. Cell Biol. 2004; 167:1183-94; Ratheesh, A., et al., Nat. Rev. Mol. Cell Biol. 2012; 13:673-9]. Lastly, the cell-cell junction width often narrowed during the pull (initial width=18.2±6.2 am, width immediately before failure=7.6±5.6 am). Perturbing at the same strain rate, the rate at which this process occurred appears to correlate with the force required to break the junction, with faster decreases in cell-cell junction width ($\Delta JW$) associating with reduced forces (FIG. 26B (vii)).

Force Response to Cyclic Perturbation and Cytoskeletal Drugs

Having characterized the effects of probe bias, we next asked whether probe actuation itself influenced cell forces over time. If subjected to cyclic stretch at sub-failure amplitudes, we hypothesized that the cell would weaken over time and exhibit decreased force with each successive stretch. This idea was based on studies performed on flat substrates, wherein cells are seeded on thin elastic films and a uniaxial or biaxial stretch on the order of 10-15% amplitude is applied to the entire film at 0.1-1 Hz [Hoffman, L. M., et al., Mol. Biol. Cell 2012; 23:1846-59; Huang, L., et al., 2010; 38:1728-40].

Figure 27A:
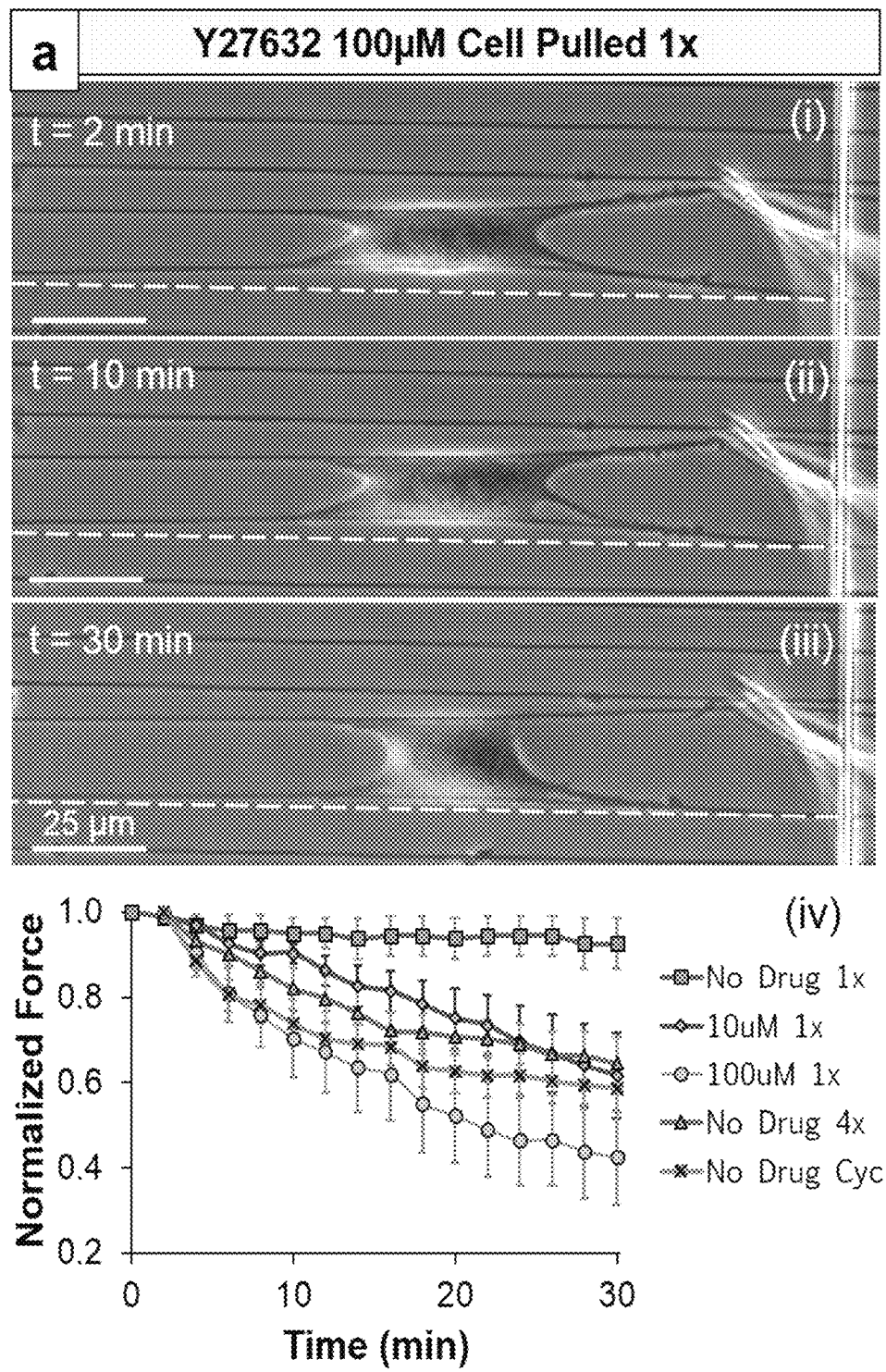
FIGS. 27A-B depict (a) timelapse images (i-iii) of the effect of cycle frequency and drug administration on cell force, (iv) increasing cycle frequency decreases cell force (1×=7% force reduction, 4×=37%, Continuous=41%), showing that increasing drug concentration while cycling at 1× also decreases force (10 µM=38%, 100 µM=57%). Despite force magnitude reduction being similar, ROCK inhibition does not appear to reach steady state within 30-minutes. Error bars represent standard error (n=6 for each case). (b) Reduction of cancer cell blebbing through probe-induced stretch, as shown by (i-iii) timelapse images and (iv) force evolution upon onset of transition (n=11).

Using a constant strain rate of 2 am/s, the probe stretched cells to a sub-failure magnitude and then returned to its original resting position. This process was repeated every two minutes for a 30-minute duration. The effect of stretching frequency was also examined: in addition to only stretching the cell once per two minute window (1×), cells were stretched four times (4×) as well as continuously (FIG. 27A (a)). It was found that when the cell was stretched a single time (1×) and then allowed to rest the remainder of the two minutes, force was not significantly reduced (decrease of 7%). However, if the cell was either cycled four times (4×) in that same two minute window (1 minute of perturbation (once every 15 seconds), 1 minute of rest) or continuously perturbed, force significantly decreased (4×=37% reduction, continuous=41%).

To further evaluate the nanonet probe system for efficacy as a drug testing platform at high magnifications and temporal resolutions, we subjected cells to varying concentrations of the rho kinase (ROCK)-inhibitor Y27632 and monitored its force evolution over the same 30-minute period. In uninhibited cells, ROCK pathway activation leads to increased cytoskeletal tension through f-actin stress fiber formation and focal adhesion development, thereby allowing cells to generate contractile forces [Amano, M., et al., Cytoskeleton (Hoboken) 2010; 67:545-54; Jaalouk, D. E., et al., Nat. Rev. Mol. Cell Biol. 2009; 10:63-73]. Y27632 competes with ATP for binding sites on ROCK, preventing this pathway's initiation and resulting in decreased cytoskeletal tension [Ishizaki, T., et al., Mol. Pharmacol. 2000; 57:976-83; Matthews, B. D., et al., J. Cell Sci. 2006; 119:508-18]. Y27632 was added at either normal (10 µM) [Lam, R. H. W., et al., Integr. Biol. (Camb) 2012; 4:1289-98; Engler, A. J., et al., Cell 2006; 126:677-689] or oversaturated (100 µM) [McGraw, K. L., et al., PLoS One 2012; 7:e34477] concentrations at the start of experimentation to quantify ROCK-inhibited force evolution. Cells treated with 10 µM Y27632 cycled at 1× (38% reduction) followed similar trends to the cyclically-perturbed control cells, and cells treated with 100 µM Y27632 cycled at 1× experienced a further reduction in force (57%). However, despite showing relatively similar reductions in force, cyclically-perturbed cells appeared to reach a steady-state force value whereas ROCK-inhibited cells did not.

Cancer Cell Blebbing Reduction with Probe Stretching

One of the identified hallmarks of cancer is the evasion of apoptosis [Hanahan, D., et al., Cell 2011; 144:646-74]. Glioma cells have been observed to exhibit reversible membrane blebbing, a phenomenon in which increased hydrostatic pressure drives cytoplasm through local ruptures in the actin cortex [Ridley, A. J. Cell 2011; 145:1012-22]. It has recently been reported that blebbing cells exist in a state of simultaneous hyper-contractility and reduced actin polymerization, but when corrected through the use of various cytoskeletal drugs, these same cells can revert back to pseudopodial/lamellipodial protrusions [Bergert, M., et al., Proc. Natl. Acad. Sci. U.S.A 2012; 109:14434-9]. Blebbing has been shown to cease when the cell takes on a spread area greater than 1400 µm$^2$ [Sharma, P., et al., Integr. Biol. 2013; 5:1036-44]. Taken together, these works suggest that blebbing can be reduced in the absence of drugs via prolonged sub-failure stretch.

Figure 27B:
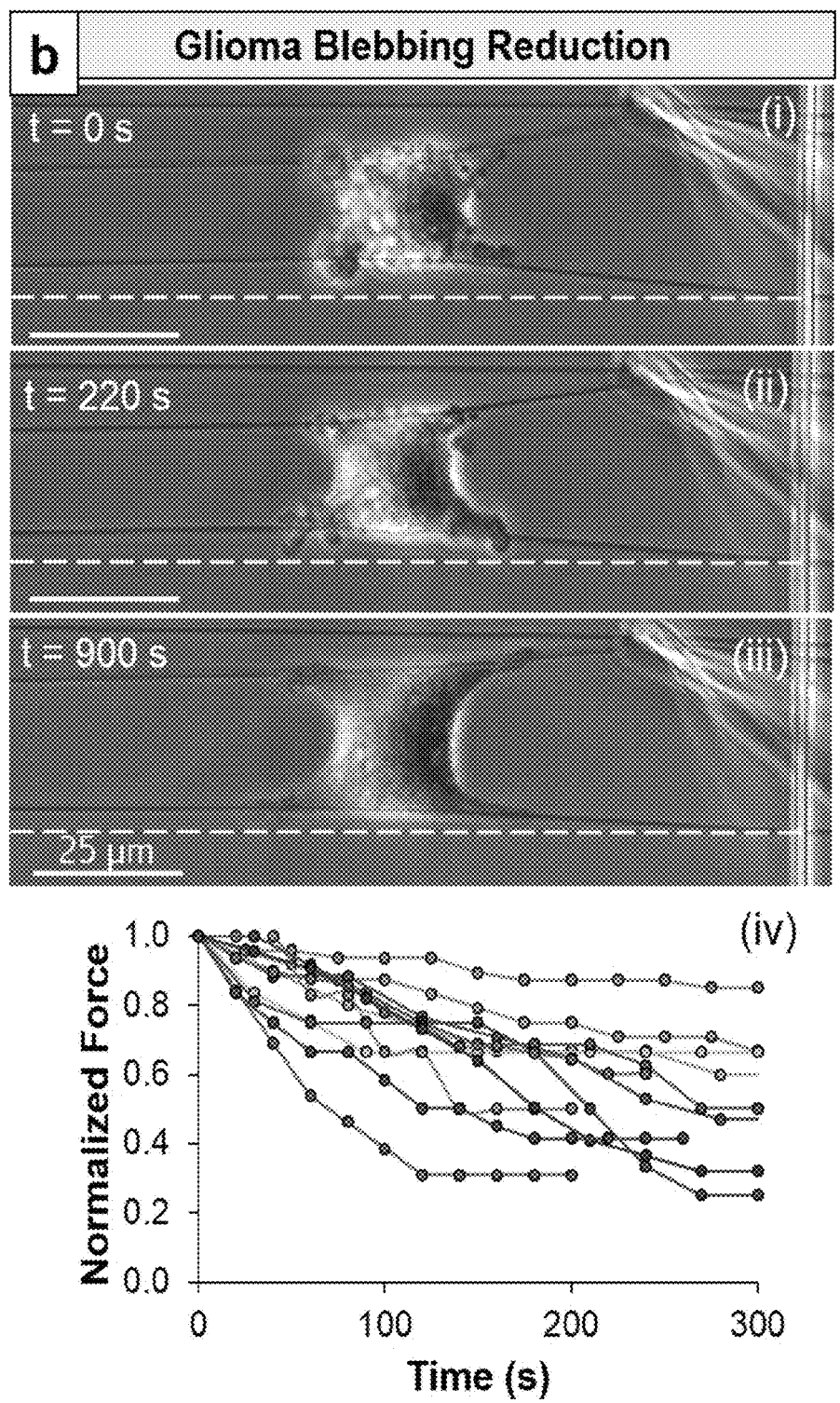

Thus, a step strain was applied to single blebbing Denver Brain Tumor Research Group (DBTRG-05MG) cells and held constant while cells transitioned from blebbing to lamellipodia (FIG. 27B (b)). Onset of transition, evidenced by the first observed force decrease, required approximately 5-10 minutes to take place. Upon initializing transition, blebbing ceased and lamellipodia were observed after another 200-400 seconds. This transition was marked by decreased cell contractility wherein the average force reduced by approximately 20 nN (40% of blebbing force, n=11).

The suspended nanofiber-based force measurement system (Nanonet Force Microscopy (NFM)) is thus capable of capturing single-cell IO contractile forces (avg. 45.0±5.4 nN) and OI adhesion forces in the absence (symmetric avg. 126.6±8.7 nN) and presence of bias (asymmetric avg. 121.0+8.6 nN). By using a single probe, bias increases failure probability on the side of the cell nearest the probe by over 30%, changing forces in a diameter-dependent manner. The origin of bias is confirmed by locating paxillin clusters on fibers of different diameters, which show greater inter-cluster scattering on larger fibers. This phenomenon is thought to be responsible for alterations to single cell adhesion force as shown by novel diameter mismatch studies. Cyclic loading, cell-cell adhesion, and cancer cell blebbing reversal phenomenon further emphasize the uniqueness and power of the platform. Nanonet force scaffolds use suspended and aligned nanofibers to investigate single-cell mechanics on ECM-like substrates and represent the first fiber-based substrate able to capture both IO and OI modes. These new tools in understanding mechanical interactions between cells and nanofibers will allow us to postulate questions regarding onset, progression, and eventual treatment of disease at the single-cell level. Knowledge gained from these experiments will enable implementation of substrate design considerations for finer control over physiological processes that are driven by mechanical cell-fiber interactions. In the future we anticipate combining these tools with chemical stimuli to develop in vitro platforms that measure cell response to comprehensive physiochemical cues.

Example 8

Viscoelastic Strain Rate Phenomena

Figure 28:
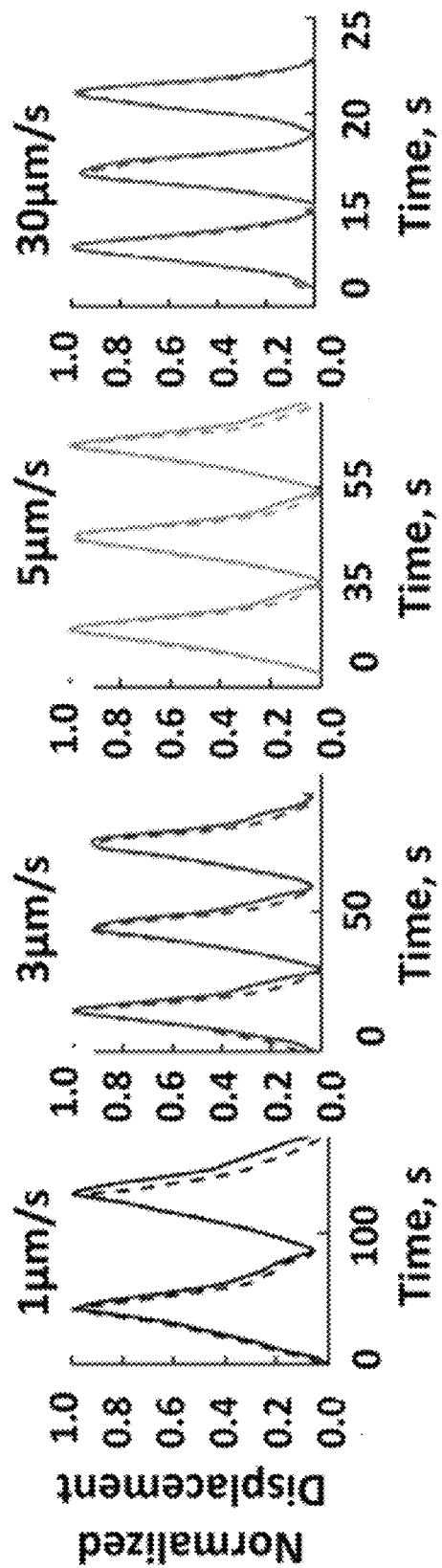
FIG. 28 shows the cycle viscoelasticity as a function of strain rate. Data shows that probe lag effects are dramatic at low strain rates compared to high strain rates.
Figure 29A:
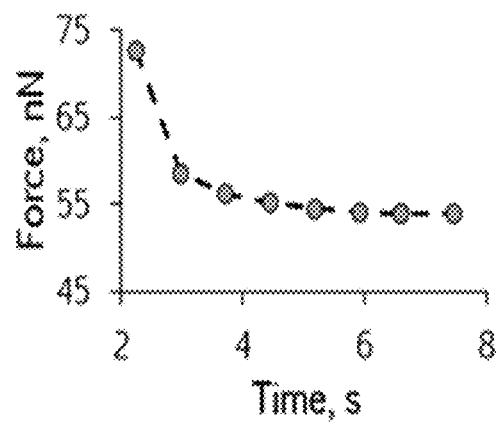
FIG. 29A-F show a stress relaxation test and associated SLS modeling. Representative single cell data for: A) Force reduction over time, B) cell elongation after step-strain is applied and held constant, and C) relaxation velocity during the test, D) Schematic of the 3-element SLS model, E) SLS parametric modeling showing dependence on $k_1$ (blue), $k_2$ (red), and $\eta$ (green) with shaded regions representing standard deviation, F) Cytoskeleton knockdown drugs nocodazole (microtubules) and blebbistatin (myosin) cause shift in major contribution from $k_2$ to $\eta$ (N=25).
Figure 29B:
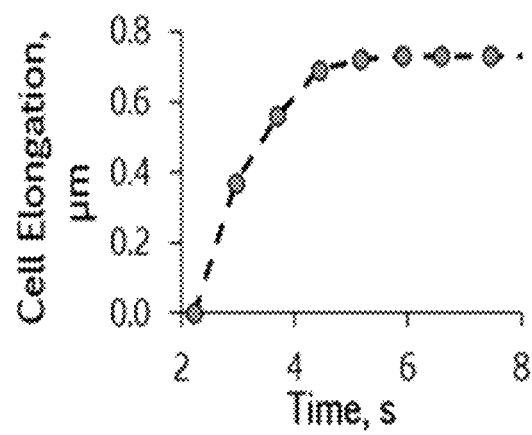
Figure 29C:
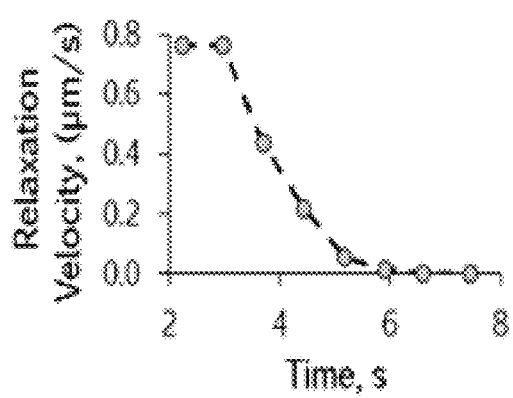
Figure 29D:
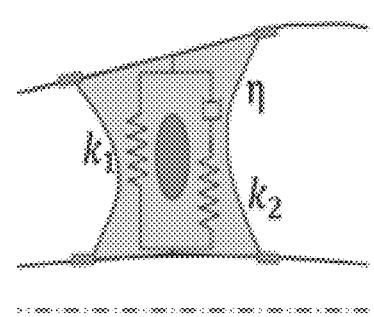
Figure 29E:
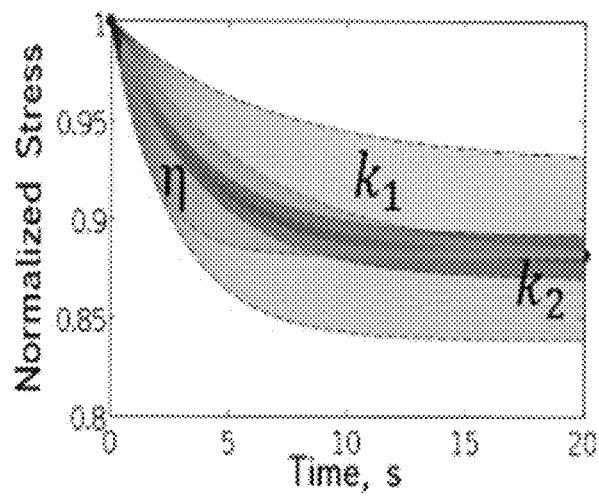
Figure 29F:
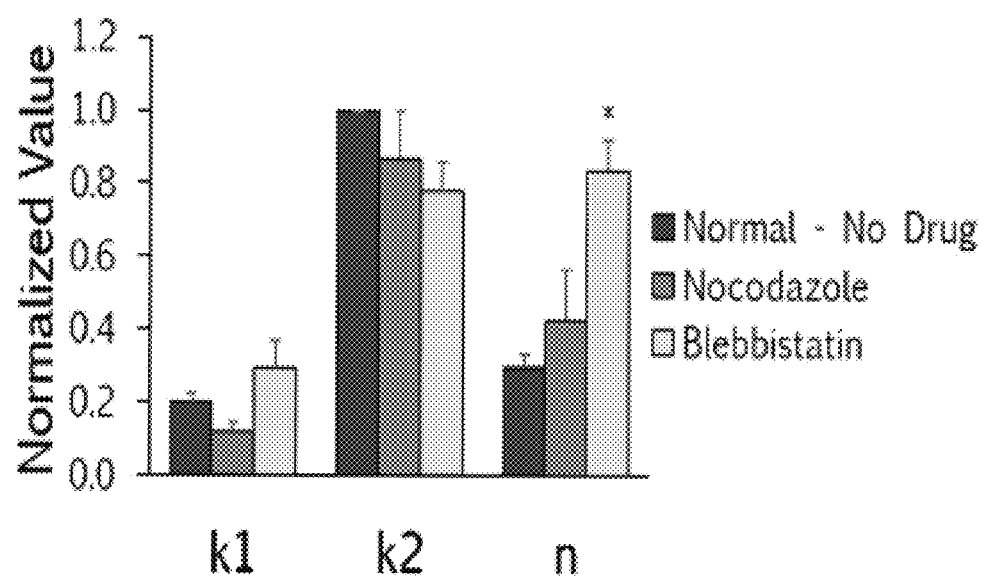

The first test to determine the extent of cellular viscoelasticity on STEP fibers was to perform a phase evaluation at various strain rates. Cells were cyclically stretched and both fiber and probe displacement were tracked for strain rates ranging from 1-30 µm/s. Plotting the displacements together reveals that viscoelastic effects appear at low strain rates and diminish at high rates (FIG. 28). The probe and passive fiber are in-phase during active pull (positive slope). Probe lag, as demonstrated by the solid lines following after the dashed lines, is observed when the probe returns to zero deflection (negative slope) for low strain rate cases. This is indicative of viscoelastic behavior: a purely elastic interaction would yield in-phase displacements throughout testing, yet instead an out-of-phase phenomenon is observed during relaxation. This behavior may originate either from the cell losing elasticity (becoming softer) when the active component is removed during relaxation, or from the release of tension built up in the fiber during active pull. In either case, probe lag effects are significantly diminished upon reaching the 3-5 µm/s strain rate threshold, and are not visible at rates higher than those (FIG. 28). This suggests that cells pulled near the threshold strain rate should behave 'purely elastically' on STEP fibers, and any strain rate effects would plateau near these values.

Example 9

Stress Relaxation Tests

As cells experience forces, interactions between cytosol and cytoskeletal structures within their semi-permeable membrane elicit strain-rate dependent responses, but identifying physiological mechanisms for this behavior has proven difficult [Janmey, P. A., et al., J. Biol. Chem. 1994; 269:32503-13; Darling, E. M., et al., Biophys. J. 2007; 92:1784-91]. Since viscoelasticity can alter the measured force at different strain rates, it is nonetheless an important parameter to qualitatively describe even without complete knowledge of the contribution of individual cellular components [Ketene, A. N., et al., Integr. Biol. (Camb). 2012; 540-9]. Viscoelastic response is quantified through the classic stress relaxation test [Nagayama, K., et al., Med. Eng.

Phys. 2007; 29:620-8; Darling, E. M., et al., Biophys. J. 2007; 92:1784-91]. In this approach, the cell undergoes an instantaneous step strain which is held constant while the cell relaxes. By tracking the rate at which this relaxation occurs, data can be fitted into viscoelastic models to establish baseline expected mechanical performance. Here, we use the standard linear solid (SLS) model which is composed of a spring ($k_1$) in parallel with a spring and damper that are in series ($k_2$ and $\eta$). When a step strain is applied, the force relaxation is described by [Leipzig, N. D., et al., Biomech. 2005; 38:77-85]:

$$F = \left(\frac{F_0}{k_1 + k_2}\right)k_2 + k_1 e^{-\frac{k_1 t}{\eta}}$$

Where $F_0$ is the initial force observed upon instantaneous strain and t is time. The advantage of fitting data to such models is that one can distinguish rate-dependent mechanical response of the cell from rate-independent ones, yet difficulty has historically emanated from drawing biological significance from these three parameters [Wen, Q., et al., Curr. Opin. Solid State Mater. Sci. 2011; 15:177-82; Mofrad, M. R. K. Annu. Rev. Fluid Mech. 2009; 41:433-53]. Moreo et al used an SLS model to describe mechanosensory response to varying substrate stiffnesses [Moreo, P., et al., Acta Biomater. 2008; 4:613-21]. In this model, three cytoskeletal elements were assumed to play a significant role in cell mechanics: microtubules, actin, and acto-myosin contractions. From the concept of tensegrity, microtubules are assumed to be compressional elements with actin primarily the tensile element [Ingber, D. E., et al., Opposing Views on Tensegrity as a Structural Framework. 2012; 1663-1678; Ingber, D. E., et al., Rep. Prog. Phys. 2014; 77:046603]. Therefore, microtubule-based disruptions would be rate-independent and suitable for the $k_1$ assignment. Likewise, since actin is bundled to the acto-myosin contraction and exhibits strain stiffening [Wen, Q., et al., Curr. Opin. Solid State Mater. Sci. 2011; 15:177-82], it is assigned to $k_2$ since it is in series with the viscous component $\eta$. Lastly, pairing acto-myosin contraction with the cell viscosity parameter $\eta$ may be an oversimplification but would capture viscous-like active cell adjustments to external forces [Yoshinaga, N., et al., Phys. Biol. 2012; 9:046004].

Stress relaxation tests were performed by applying an instantaneous step displacement of 16±6 μm at 100 am/s and data was fitted to the SLS model (FIG. 29). Cells that experience a step strain exhibit viscoelasticity and require several seconds to fully relax. FIG. 29B shows elongation of the cell throughout the test. FIG. 29C shows that peak membrane velocities during these tests were found to be on the order of 1 μm/s, which may partially explain why the system exhibits probe lag near this strain rate. The three-element SLS model was used to fit relaxation data as shown by the dashed line in FIG. 29E. Cells relaxed to 85-95% of their original force value, with the major contribution stemming from $k_1$ (shown in blue in FIG. 29E). The predicted assignment of microtubules, actin, and acto-myosin contractility to the three elements in the SLS model by Moreo et al. presents a testable case with the use of selective knockout agents. Microtubules were therefore depolymerized with 10 μM nocodazole administration [Ezratty, E. J., et al., Nat Cell Biol 2005; 7:581-590]. The acto-myosin contractile element of the cell was disrupted with 50 μM blebbistatin, which interferes with myosin-II [Fournier, M. F., et al., J. Cell Biol. 2010; 188:287-97]. Lastly, actin can be depolymerized with cytochalasin D, but doing so would interfere with the acto-myosin component as well so this agent was not used [Schliwa, M. J. Cell Biol. 1982; 92:79-91]. Normalized values for $k_1$, $k_2$, and $\eta$ plotted in FIG. 29F show shifting in the relative contributions from $k_2$ to $\eta$ for both drug cases, suggesting the correlation of these parameters to biological components is either an oversimplification or that the SLS model is unable to capture this dependency.

The present invention further includes the subject matter of the following clauses.

Clause 1: A method of measuring a cell force comprising: providing one or more cells on a nanofiber grid suspended in an aqueous medium or a hydrogel, wherein the nanofiber grid comprises a plurality of high aspect ratio fibers having diameters of between about 10 nm and 10 μm, wherein the fibers are formed into a crossed pattern having one or more intersections, and wherein the fibers are fused at the intersections of the crossed pattern, wherein at least one cell is in contact with a first fiber; measuring deflection of the first fiber in contact with the at least one cell; and calculating from the deflection of the first fiber a force applied to the fiber by the at least one cell.

Clause 2: The method of clause 1, wherein the cell contacts a plurality of fibers and the deflection of more than one fiber is measured, and forces acting on the more than one fiber for which deflection is measured are calculated.

Clause 3: The method of any of clauses 1-2, in which the high aspect ratio fibers are polymeric.

Clause 4: The method of any of clauses 1-3, wherein the polymer is or more of a polystyrene, a polyester, a polyurethane, a polyacrylamide, a poly(methyl methacrylate), a polylactic acid, a poly(glycolic acid), a poly(lactic-co-glycolic acid), a polyaniline, a polypyrrole, fibrinogen, collagen, and mixtures and/or copolymers thereof, and/or includes carbon nanotubes, carbon black, or metallic nanoparticles.

Clause 5: The method of any of clauses 1-4, in which the polymeric high aspect ratio fibers are prepared by determining an entanglement concentration (Ce) for a first polymer solution comprising a first polymer and a first good solvent for the first polymer; feeding the first polymer solution comprising the first polymer having a concentration of at least Ce in the first good solvent for the first polymer through a spinneret to produce an extruded droplet of polymer solution at a tip of the spinneret; contacting the extruded droplet of polymer solution with a target at a contact point; moving the contact point away from the spinneret, thereby pulling a high aspect ratio polymeric fiber from the extruded droplet of polymer solution at the tip of the spinneret; and further pulling the fiber from the extruded droplet of polymer solution at the tip of the spinneret and feeding the first polymer solution through the spinneret into the extruded droplet of polymer solution at the tip of the spinneret at a rate sufficient to compensate for an amount of the first polymer solution used to produce the fiber, thereby producing a bead-free, high aspect ratio polymeric fiber.

Clause 6: The method of any of clauses 1-5, in which the nanofiber grid comprises a plurality of spaced-apart support fibers having a diameter ranging from 1 μm to 100 μm, spanning a frame, and a plurality of crossing fibers, crossing the support fibers, having a diameter of from 50 nm to 1 μm, and spaced-apart at a distance of between 10 μm and 100 μm.

Clause 7: The method of clause 6, in which the nanofiber grid comprises a frame, wherein the support fibers and the crossing fibers span the frame.

Clause 8: The method of any of clauses 6-7, in which the crossing fibers form an angle with the support fibers of from 10° to 90°.

Clause 9: The method of any of clauses 6-8, in which the support fibers are perpendicular to the crossing fibers.

Clause 10: The method of any of clauses 1-9, wherein the high aspect ratio fibers formed into a crossed pattern having two different directions, wherein the high aspect ratio polymeric fibers have different diameters in each direction of the crossed pattern.

Clause 11: The method of any of clauses 1-10, in which the first fiber deflects at least 20 nm with an applied force ranging from 10 pico-Newtons to 100 micro-Newtons, applied normal to the first fiber.

Clause 12: The method of any of clauses 1-11, wherein the cell is attached to a second fiber, and the method further comprises, prior to measuring the deflection of the at least one fiber, moving a second fiber attached to the cell using a first probe placed at a point on the second fiber adjacent to the cell on a first side of the cell between the cell and a first intersection adjacent to the cell.

Clause 13: The method of clause 12, further comprising moving the second fiber using the first probe, and a second probe at a point on the second fiber adjacent to the cell on a second side of the cell opposite the first side between the cell and a second intersection adjacent to the cell.

Clause 14: The method of clause 13, wherein the force applied to the cell on the first side is different to the force applied to the cell on the second side.

Clause 15: The method of any of clauses 12-14, further comprising moving the first fiber with a probe placed at a point on the first fiber adjacent to the cell on a side of the cell opposite a point on the first fiber at which the deflection of the fiber is measured between the cell and a second intersection adjacent to the cell.

Clause 16: The method of any of clauses 12-15, in which deflection of the first fiber is indicative of cell-cell junction strength, cytoskeletal structure, cell integrity, cell stress and/or strain values, and/or cell drug response of the cell on the first fiber.

Clause 17: The method of any of clauses 12-16, wherein the second fiber is moved until the cell begins to detach or detaches from the first fiber and/or the second fiber, and determining the force applied to the first fiber by the cell at the time the cell begins to detach and/or detaches from the first fiber and/or the second fiber.

Clause 18: The method of any of clauses 1-17, in which one or more fibers of the nanofiber grid comprise a cell adhesion-promoting composition.

Clause 19: The method of clause 18, wherein the cell adhesion-promoting composition is one or more of: collagen, vitronectin, laminin, fibronectin, fibrinogen, poly(ornithine), poly(lysine), and a cell-adhesion promoting peptide.

Clause 20: The method of any of clauses 1-19, in which the first fiber comprises a label.

Clause 21: The method of clause 20, in which the label is selected from the group consisting of a fluorescent dye, and a quantum dot.

Clause 22: The method of any of clauses 1-21, in which deflection of the first fiber is measured by obtaining an image of the first fiber using a digital imaging device, transmitting the image of the first fiber to a computer, determining by use of a computer-implemented process the displacement of the first fiber by the cell, calculating from the displacement a force that is used to displace the first fiber to the extent depicted in the image, and producing an output indicating the force that is used to displace the first fiber to the extent depicted in the image.

Clause 23: The method of any of clauses 1-22, further comprising adding one or more active agents or samples to the aqueous medium and determining deflection of the first fiber either at one or more time points prior to or after addition of the active agent to the aqueous medium, or compared to a cell deposited on a second nanofiber grid in aqueous medium in a second vessel without addition of the active agent, or without addition of the same amount of active agent or sample.

Clause 24: The method of any of clauses 1-23, further comprising aspirating the cell, wherein aspirating the cell comprises pulling the cell on the first fiber, and optionally detaching the cell from the first fiber, and wherein the deflection of the first fiber is measured during aspiration of the cell.

Clause 25: The method of any of clauses 1-24, in which deflection of the first fiber and one or more additional fibers is measured to identify contraction forces and expansion forces of the cell during apoptosis.

Clause 26: The method of any of clauses 1-25, in which deflection of the first fiber is indicative of the action of cell protrusions, cell migration, cell division, cell apoptosis, action of a leader cell, cell aspiration, cell debris, and/or cell drug response on the first fiber.

Clause 27: A method of staging cancer cells from a patient biopsy, comprising depositing cells in cell culture medium or a hydrogel on or adjacent to a nanofiber grid having a frame and plurality of high aspect ratio polymeric fibers having diameters of between about 10 nm and 10 μm, extending from the frame, to form an initial cell mass, culturing the cells, and determining an extent of migration of cells from the initial cell mass along the polymeric fibers, wherein the greater the extension of leader cells from the initial cell mass onto the fibers is indicative of a more aggressive cancer. The detachment of cell mass onto fibers can be in single or collective groups of cells.

Clause 28: A nanofiber grid, comprising: a frame; a plurality of spaced-apart support fibers having a thickness ranging from 1 μm to 100 μm, spanning the frame; and a plurality of crossing fibers spanning the frame and crossing the support fibers, having a thickness of from 50 nm to 1 μm, and spaced-apart at a distance of between 10 μm and 100 μm, wherein the support fibers and the crossing fibers intersect at intersections and are fused together at the intersections.

Clause 29: The nanofiber grid of clause 28, wherein the support fibers are parallel to each other, the crossing fibers are parallel to each other, and/or the support fibers and crossing fibers are perpendicular to each other.

Clause 30: A method of making a nanofiber grid comprising: depositing a plurality of spaced-apart support fibers having a thickness ranging from 1 μm to 100 μm across the frame; depositing a plurality of crossing fibers having a thickness of from 50 nm to 1 μm, and spaced-apart at a distance of between 10 μm and 100 μm across the frame and crossing the support fibers; and fusing the crossing fibers to the support fibers at points of intersection of the crossing fibers and support fibers to produce a nanofiber grid.

Clause 31: The method of clause 30, wherein the crossing fibers are fused to the support fibers by exposure to a solvent, a solvent vapor, a cross-linker, heating, laser annealing, or exposure to electromagnetic radiation.

Clause 32: A system for converting fiber deflection data into data of a high aspect ratio fiber in a crossed, fused nanofiber grid (e.g., as described anywhere herein, for example as in clauses 1-29), the fiber being in contact with at least one cell in an aqueous medium, comprising: an imaging device; and a computer connected to the imaging device comprising a processor and executable instructions for converting the deflection data of the fiber to the force on the fiber from an image of the fiber and the at least one cell on the crossed, fused scaffold, the executable instructions comprising: i. obtaining an image of an entire surface of the scaffold and the at least one cell from the imaging device; ii. producing from the image, using a computer-implemented method, a plurality of profiles of the positions of the fiber in contact with the cell; iii. calculating the deflection forces of the fiber using the profiles of the positions of the fiber in contact with the cell; iv. converting the deflection of the fiber into the forces acting on the fiber using a deflection equation for a beam (e.g., beam mechanics); and v. producing an output from converting step iv.

Whereas particular embodiments of this invention have been described above for purposes of illustration, it will be evident to those skilled in the art that numerous variations of the details of the present invention may be made without departing from the invention as defined in the appended claims.

5. The method of claim 3, in which the polymeric high aspect ratio fibers are prepared by determining an entanglement concentration (Ce) for a first polymer solution comprising a first polymer and a first good solvent for the first polymer; feeding the first polymer solution comprising the first polymer having a concentration of at least Ce in the first good solvent for the first polymer through a spinneret to produce an extruded droplet of polymer solution at a tip of the spinneret; contacting the extruded droplet of polymer solution with a target at a contact point; moving the contact point away from the spinneret, thereby pulling a high aspect ratio polymeric fiber from the extruded droplet of polymer solution at the tip of the spinneret; and further pulling the fiber from the extruded droplet of polymer solution at the tip of the spinneret and feeding the first polymer solution through the spinneret into the extruded droplet of polymer solution at the tip of the spinneret at a rate sufficient to compensate for an amount of the first polymer solution used to produce the fiber, thereby producing a bead-free, high aspect ratio polymeric fiber.

6. The method of claim 1, in which the nanofiber grid comprises a plurality of spaced-apart support fibers having a diameter ranging from 1 µm to 100 µm, spanning a frame,

We claim:
1. A method of measuring a cell force comprising:
  a. providing one or more cells on a nanofiber grid suspended in an aqueous medium or a hydrogel, wherein the nanofiber grid comprises a plurality of high aspect ratio fibers having diameters of between about 10 nm and 10 µm, wherein the fibers are formed into a crossed pattern having one or more intersections, and wherein the fibers are fused at the intersections of the crossed pattern, wherein at least one cell is in contact with a first fiber;
  b. measuring deflection of the first fiber in contact with the at least one cell; and
  c. calculating from the deflection of the first fiber a force applied to the fiber by the at least one cell.
2. The method of claim 1, wherein the cell contacts a plurality of fibers and the deflection of more than one fiber is measured, and forces acting on the more than one fiber for which deflection is measured are calculated.
3. The method of claim 1, in which the high aspect ratio fibers are polymeric.
4. The method of claim 3, wherein the polymer is one or more of a polystyrene, a polyester, a polyurethane, a polyacrylamide, a poly(methyl methacrylate), a polylactic acid, a poly(glycolic acid), a poly(lactic-co-glycolic acid), a polyaniline, a polypyrrole, fibrinogen, collagen, and mixtures and copolymers thereof, and/or includes carbon nanotubes, carbon black, or metallic nanoparticles.

and a plurality of crossing fibers, crossing the support fibers, having a diameter of from 50 nm to 1 µm, and spaced-apart at a distance of between 10 µm and 100 µm.

7. The method of claim 6, wherein the support fibers and the crossing fibers span the frame.

8. The method of claim 6, in which the crossing fibers form an angle with the support fibers of from 10° to 90°.

9. The method of claim 6, in which the support fibers are perpendicular to the crossing fibers.

10. The method of claim 1, wherein the high aspect ratio fibers formed into a crossed pattern having two different directions, wherein the high aspect ratio polymeric fibers have different diameters in each direction of the crossed pattern.

11. The method of claim 1, in which the first fiber deflects at least 20 nm with an applied force ranging from 10 pico-Newtons to 100 micro-Newtons, applied normal to the first fiber.

12. The method of claim 1, wherein the cell is attached to a second fiber, and the method further comprises, prior to measuring the deflection of the at least one fiber, moving a second fiber attached to the cell using a first probe placed at a point on the second fiber adjacent to the cell on a first side of the cell between the cell and a first intersection adjacent to the cell.

13. The method of claim 12, further comprising moving the second fiber using the first probe, and a second probe at a point on the second fiber adjacent to the cell on a second side of the cell opposite the first side between the cell and a second intersection adjacent to the cell.

14. The method of claim 13, wherein the force applied to the cell on the first side is different to the force applied to the cell on the second side.

15. The method of claim 12, further comprising moving the first fiber with a probe placed at a point on the first fiber adjacent to the cell on a side of the cell opposite a point on the first fiber at which the deflection of the fiber is measured between the cell and a second intersection adjacent to the cell.

16. The method of claim 12, in which deflection of the first fiber is indicative of cell-cell junction strength, cytoskeletal structure, cell integrity, cell stress and/or strain values, and/or drug response of the cell.

17. The method of claim 12, wherein the second fiber is moved until the cell begins to detach or detaches from the first fiber and/or the second fiber, and determining the force applied to the first fiber by the cell at the time the cell begins to detach and/or detaches from the first fiber and/or the second fiber.

18. The method of claim 1, in which one or more fibers of the nanofiber grid comprise a cell adhesion-promoting composition.

19. The method of claim 18, wherein the cell adhesion-promoting composition is one or more of: collagen, vitronectin, laminin, fibronectin, fibrinogen, poly(ornithine), poly(lysine), and a cell-adhesion promoting peptide.

20. The method of claim 1, in which the first fiber comprises a label.

21. The method of claim 20, in which the label is selected from the group consisting of a fluorescent dye, and a quantum dot.

22. The method of claim 1, in which deflection of the first fiber is measured by obtaining an image of the first fiber using a digital imaging device, transmitting the image of the first fiber to a computer, determining by use of a computer-implemented process the displacement of the first fiber by the cell, calculating from the displacement a force that is used to displace the first fiber to the extent depicted in the image, and producing an output indicating the force that is used to displace the first fiber to the extent depicted in the image.

23. The method of claim 1, further comprising adding one or more active agents to the aqueous medium or hydrogel and determining deflection of the first fiber either at one or more time points prior to or after addition of the active agent(s) to the aqueous medium, or compared to a cell deposited on a second nanofiber grid in aqueous medium in a second vessel without the addition of the active agent(s), or with the addition of a different amount of the active agent(s).

24. The method of claim 1, further comprising aspirating the cell, wherein aspirating the cell comprises pulling the cell on the first fiber, and optionally detaching the cell from the first fiber, and wherein the deflection of the first fiber is measured during aspiration of the cell.

25. The method of claim 1, in which deflection of the first fiber and one or more additional fibers is measured to identify contraction forces and expansion forces of the cell during apoptosis.

26. The method of claim 1, in which deflection of the first fiber is indicative of the action of cell attachment dynamics, cell protrusions, cell migration, cell division, cell apoptosis, action of a leader cell, cell aspiration, cell debris, and/or cell drug response.

27. The method of claim 6, wherein the support fibers are parallel to each other, the crossing fibers are parallel to each other, and/or the support fibers and crossing fibers are perpendicular to each other.

28. The method of claim 26, further comprising staging cancer cells from a patient biopsy, comprising:
   d. depositing cells in cell culture medium or a hydrogel on or adjacent to the nanofiber grid, having the frame and plurality of high aspect ratio polymeric fibers having diameters of between about 10 nm and 10 µm, extending from the frame, to form an initial cell mass;
   e. culturing the cells; and
   f. determining an extent of migration of cells from the initial cell mass along the polymeric fibers,
   wherein the greater the extension of leader cells from the initial cell mass onto the fibers is, the greater the indication of a cancerous phenotype, and wherein the detachment of cell mass onto fibers can be in single or collective groups of cells.

29. The method of claim 1, further comprising preparing the nanofiber grid by:
   a. depositing a plurality of spaced-apart support fibers having a thickness ranging from 1 µm to 100 µm across the frame;
   b. depositing a plurality of crossing fibers having a thickness of from 50 nm to 1 µm, and spaced-apart at a distance of between 10 µm and 100 µm across the frame and crossing the support fibers; and
   c. fusing the crossing fibers to the support fibers at points of intersection of the crossing fibers and support fibers to produce a nanofiber grid.

30. The method of claim 29, wherein the crossing fibers are fused to the support fibers at the points of intersection by exposure to a solvent, a solvent vapor, or a cross-linker, or by heating or laser annealing, or by exposure to electromagnetic radiation.

31. The method of claim 7, wherein deflection data produced by measuring the deflection of the first fiber is converted into data of the high aspect ratio fiber in the crossed, fused nanofiber grid, the fiber being in contact with the at least one cell in the aqueous medium, wherein the deflection data is sent to:
   a. an imaging device; and
   b. wherein a computer is connected to the imaging device comprising a processor and executable instructions for converting the deflection data of the fiber to the force on the fiber from an image of the fiber and the at least one cell on the crossed, fused scaffold, the executable instructions comprising:
      i. obtaining an image of an entire surface of the scaffold and the at least one cell from the imaging device;
      ii. producing from the image, using a computer-implemented method, a plurality of profiles of the positions of the fiber in contact with the cell;
      iii. calculating the deflection forces of the fiber using the profiles of the positions of the fiber in contact with the cell;
      iv. converting the deflection of the fiber into the forces acting on the fiber using a deflection equation for a beam; and
      v. producing an output from converting step iv.

* * * * *